US006166302A

United States Patent [19]
Merlo et al.

[11] Patent Number: 6,166,302
[45] Date of Patent: Dec. 26, 2000

[54] **MODIFIED *BACILLUS THURINGIENSIS* GENE FOR LEPIDOPTERAN CONTROL IN PLANTS**

[75] Inventors: Donald J. Merlo; Otto Folkerts, both of Carmel, Ind.

[73] Assignee: Dow AgroSciences LLC, Indianapolis, Ind.

[21] Appl. No.: 08/729,601

[22] Filed: Oct. 11, 1996

Related U.S. Application Data

[60] Provisional application No. 60/005,405, Oct. 13, 1995.

[51] Int. Cl.⁷ .............................. A01H 5/00; A01H 5/10; C12N 15/32; C12N 15/82
[52] U.S. Cl. .................................. 800/320.1; 435/320.1; 435/419; 435/468; 536/23.71; 800/279; 800/302
[58] Field of Search ....................... 536/23.71; 435/172.3, 435/320.1, 419, 418, 69.1; 800/205, 250, DIG. 56

[56] References Cited

U.S. PATENT DOCUMENTS

| | | | |
|---|---|---|---|
| 4,764,372 | 8/1988 | Hermstadt et al. | 424/93 |
| 4,771,131 | 9/1988 | Hermstadt et al. | 536/27 |
| 4,797,276 | 1/1989 | Hermtadt et al. | 424/84 |
| 4,889,918 | 12/1989 | Krieg et al. | 530/350 |
| 4,945,050 | 7/1990 | Sanford et al. | 435/172.1 |
| 4,948,734 | 8/1990 | Edwards et al. | 435/252.5 |
| 4,973,676 | 11/1990 | Krieg et al. | 536/22 |
| 5,034,322 | 7/1991 | Rogers et al. | 435/172.3 |
| 5,036,006 | 7/1991 | Sanford et al. | 435/170.1 |
| 5,055,294 | 10/1991 | Gilroy | 424/93 |
| 5,141,131 | 8/1992 | Miller, Jr. et al. | 222/54 |
| 5,186,934 | 2/1993 | Narva et al. | 124/93 |
| 5,187,091 | 2/1993 | Donovan et al. | 435/240.4 |
| 5,231,019 | 7/1993 | Paszkowski et al. | 435/172.3 |
| 5,262,159 | 11/1993 | Payne et al. | 424/93 |
| 5,286,485 | 2/1994 | Uyeda et al. | 424/93 |
| 5,286,486 | 2/1994 | Payne et al. | 424/93 |
| 5,380,831 | 1/1995 | Adang et al. | 536/23.71 |
| 5,625,136 | 4/1997 | Koziel et al. | 800/205 |

FOREIGN PATENT DOCUMENTS

| | | |
|---|---|---|
| B-30297/89 | 10/1989 | Australia . |
| 131620 | 1/1985 | European Pat. Off. . |
| 131623 | 1/1985 | European Pat. Off. . |
| 142924 | 5/1985 | European Pat. Off. . |
| 192319 | 8/1986 | European Pat. Off. . |
| 193259 | 9/1986 | European Pat. Off. . |
| 202470 | 11/1986 | European Pat. Off. . |
| 204590 | 12/1986 | European Pat. Off. . |
| 206613 | 12/1986 | European Pat. Off. . |
| 209370 | 1/1987 | European Pat. Off. . |
| 213818 | 3/1987 | European Pat. Off. . |
| 289479 | 11/1988 | European Pat. Off. . |
| 290395 | 11/1988 | European Pat. Off. . |
| 292435 | 11/1988 | European Pat. Off. . |
| 318143 | 5/1989 | European Pat. Off. . |
| 325400 | 7/1989 | European Pat. Off. . |
| 340197 | 11/1989 | European Pat. Off. . |
| 358557 | 3/1990 | European Pat. Off. . |
| 359472 | 3/1990 | European Pat. Off. . |
| 385962 | 9/1990 | European Pat. Off. . |
| 401979 | 12/1990 | European Pat. Off. . |
| 431829 | 6/1991 | European Pat. Off. . |
| 433945 | 6/1991 | European Pat. Off. . |
| 451878 | 10/1991 | European Pat. Off. . |
| 501650 | 9/1992 | European Pat. Off. . |
| 582541 | 2/1994 | European Pat. Off. . |
| WO 83/01176 | 4/1983 | WIPO . |
| WO 84/02919 | 8/1984 | WIPO . |
| WO 86/01536 | 3/1986 | WIPO . |
| WO 87/06614 | 11/1987 | WIPO . |
| WO 89/04868 | 6/1989 | WIPO . |
| WO 90/09445 | 8/1990 | WIPO . |
| WO 91/16432 | 10/1991 | WIPO . |
| WO 91/16433 | 10/1991 | WIPO . |
| WO 91/16434 | 10/1991 | WIPO . |
| WO 92/09696 | 6/1992 | WIPO . |
| WO 92/12250 | 7/1992 | WIPO . |
| WO 93/04587 | 3/1993 | WIPO . |
| WO 93/07278 | 4/1993 | WIPO . |
| WO 93/21335 | 10/1993 | WIPO . |

OTHER PUBLICATIONS

Callis et al. "Introns increase gene expression in cultured maize cells." Genes Dev. 1:1183–1200, 1987.

*Primary Examiner*—Douglas W. Robinson
*Assistant Examiner*—Amy J. Nelson
*Attorney, Agent, or Firm*—Fitch, Even, Tabin & Flannery

[57] ABSTRACT

Synthetic DNA sequences which are optimized for expression in plants, particularly maize, and which encode a *Bacillus thuringiensis* protein that is toxic to specific insects are provided, along with methods for the engineering of any synthetic insecticidal gene in maize.

10 Claims, 8 Drawing Sheets

SEQUENCE LISTING (1) GENERAL INFORMATION:

(iii) NUMBER OF SEQUENCES: 84

(2) INFORMATION FOR SEQ ID NO:1:

(i) SEQUENCE CHARACTERISTICS:
      (A) LENGTH: 1854 base pairs
      (B) TYPE: nucleic acid
      (C) STRANDEDNESS: unknown
      (D) TOPOLOGY: unknown (ii) MOLECULE TYPE: DNA (genomic)

(ix) FEATURE:
      (A) NAME/KEY: CDS
      (B) LOCATION: 1..1854

(xi) SEQUENCE DESCRIPTION: SEQ ID NO:1:

```
ATG GAC AAC AAC CCA AAC ATC AAC GAG TGC ATC CCT TAC AAC TGC TTG   48
Met Asp Asn Asn Pro Asn Ile Asn Glu Cys Ile Pro Tyr Asn Cys Leu
 1               5                  10                  15

AGC AAC CCT GAG GTG GAG GTG CTT GGT GGT GAG CGC ATT GAG ACC GGC   96
Ser Asn Pro Glu Val Glu Val Leu Gly Gly Glu Arg Ile Glu Thr Gly
             20                  25                  30

TAC ACC CCA ATC GAC ATC TCT CTG AGC CTG ACC CAA TTC CTG CTG TCT  144
Tyr Thr Pro Ile Asp Ile Ser Leu Ser Leu Thr Gln Phe Leu Leu Ser
         35                  40                  45

GAG TTC GTG CCA GGT GCT GGC TTC GTG CTT GGT CTG GTC GAC ATC ATC  192
Glu Phe Val Pro Gly Ala Gly Phe Val Leu Gly Leu Val Asp Ile Ile
     50                  55                  60

TGG GGC ATC TTC GGC CCA AGC CAA TGG GAC GCT TTC CTT GTG CAA ATC  240
Trp Gly Ile Phe Gly Pro Ser Gln Trp Asp Ala Phe Leu Val Gln Ile
 65                  70                  75                  80

GAG CAG CTC ATC AAC CAA CGC ATT GAG GAG TTC GCT CGC AAC CAA GCC  288
Glu Gln Leu Ile Asn Gln Arg Ile Glu Glu Phe Ala Arg Asn Gln Ala
                 85                  90                  95

ATC TCC AGG CTT GAG GGC TTG AGC AAC CTG TAC CAA ATC TAC GCT GAG  336
Ile Ser Arg Leu Glu Gly Leu Ser Asn Leu Tyr Gln Ile Tyr Ala Glu
            100                 105                 110

AGC TTG AGG GAG TGG GAG GCT GAC CCA ACC AAC CCA GCC TTG AGG GAG  384
Ser Phe Arg Glu Trp Glu Ala Asp Pro Thr Asn Pro Ala Leu Arg Glu
        115                 120                 125

GAG ATG CGC ATC CAA TTC AAC GAC ATG AAC TCT GCT CTG ACC ACG GCC  432
Glu Met Arg Ile Gln Phe Asn Asp Met Asn Ser Ala Leu Thr Thr Ala
    130                 135                 140

ATC CCT CTG TTC GCT GTG CAG AAC TAC CAA GTG CCT CTT CTG AGC GTC  480
Ile Pro Leu Phe Ala Val Gln Asn Tyr Gln Val Pro Leu Leu Ser Val
145                 150                 155                 160

TAC GTG CAA GCT GCC AAC TTG CAC CTG TCT GTG TTG AGG GAC GTG TCT  528
Tyr Val Gln Ala Ala Asn Leu His Leu Ser Val Leu Arg Asp Val Ser
                165                 170                 175

GTG TTC GGT CAA CGC TGG GGC TTC GAT GCT GCC ACC ATC AAC TCT CGC  576
Val Phe Gly Gln Arg Trp Gly Phe Asp Ala Ala Thr Ile Asn Ser Arg
            180                 185                 190

TAC AAC GAC CTG ACC AGG CTG ATT GGC AAC TAC ACG GAC TAC GCT GTG  624
Tyr Asn Asp Leu Thr Arg Leu Ile Gly Asn Tyr Thr Asp Tyr Ala Val
        195                 200                 205

CGC TGG TAC AAC ACG GGC CTC GAG AGG GTG TGG GGT CCA GAC TCC AGG  672
Arg Trp Tyr Asn Thr Gly Leu Glu Arg Val Trp Gly Pro Asp Ser Arg
    210                 215                 220
```

```
GAC TGG GTG CGT TAC AAC CAA TTC CGC AGG GAG CTG ACC CTG ACG GTG  720
Asp Trp Val Arg Tyr Asn Gln Phe Arg Arg Glu Leu Thr Leu Thr Val
225                 230                 235                 240

CTT GAC ATT GTG GCT CTG TTC CCA AAC TAC GAC TCC CGT CGC TAC CCA  768
Leu Asp Ile Val Ala Leu Phe Pro Asn Tyr Asp Ser Arg Arg Tyr Pro
                245                 250                 255

ATC CGC ACG GTG TCT CAG CTG ACT AGG GAG ATT TAC ACC ACC CCA GTT  816
Ile Arg Thr Val Ser Gln Leu Thr Arg Glu Ile Tyr Thr Thr Pro Val
            260                 265                 270

TTG GAG AAC TTC GAT GGC TCC TTC AGG GGC TCT GCT CAA GGC ATT GAG  864
Leu Glu Asn Phe Asp Gly Ser Phe Arg Gly Ser Ala Gln Gly Ile Glu
        275                 280                 285

CGC AGC ATT CGC TCT CCT CAC CTG ATG GAC ATT CTT AAC AGC ATC ACT  912
Arg Ser Ile Arg Ser Pro His Leu Met Asp Ile Leu Asn Ser Ile Thr
290                 295                 300

ATC TAC ACG GAC GCT CAC CGC GGC TAC TAC TAC TGG TCT GGC CAC CAA  960
Ile Tyr Thr Asp Ala His Arg Gly Tyr Tyr Tyr Trp Ser Gly His Gln
305                 310                 315                 320

ATC ATG GCT TCC CCA GTT GGT TTC TCT GGC CCA GAG TTC ACC TTC CCT 1008
Ile Met Ala Ser Pro Val Gly Phe Ser Gly Pro Glu Phe Thr Phe Pro
                325                 330                 335

TTG TAC GGT ACG ATG GGC AAC GCT GCT CCA CAA CAG CGC ATT GTG GCT 1056
Leu Tyr Gly Thr Met Gly Asn Ala Ala Pro Gln Gln Arg Ile Val Ala
            340                 345                 350

CAA CTG GGC CAA GGT GTG TAC CGC ACC CTT TCC AGC ACC TTG TAC CGC 1104
Gln Leu Gly Gln Gly Val Tyr Arg Thr Leu Ser Ser Thr Leu Tyr Arg
        355                 360                 365

CGC CCA TTC AAC ATT GGC ATC AAC AAC CAA CAG CTT TCT GTG CTT GAT 1152
Arg Pro Phe Asn Ile Gly Ile Asn Asn Gln Gln Leu Ser Val Leu Asp
370                 375                 380

GGC ACT GAG TTC GCT TAC GGC ACC TCT AGC AAC TTG CCA AGC GCT GTG 1200
Gly Thr Glu Phe Ala Tyr Gly Thr Ser Ser Asn Leu Pro Ser Ala Val
385                 390                 395                 400

TAC CGC AAG TCT GGT ACC GTG GAC AGC TTG GAC GAG ATC CCT CCA CAG 1248
Tyr Arg Lys Ser Gly Thr Val Asp Ser Leu Asp Glu Ile Pro Pro Gln
                405                 410                 415

AAC AAC AAC GTG CCA CCT CGC CAA GGC TTC TCT CAC CGC TTG AGC CAC 1296
Asn Asn Asn Val Pro Pro Arg Gln Gly Phe Ser His Arg Leu Ser His
            420                 425                 430

GTT TCC ATG TTC CGT TCG GGC TTC AGC AAC AGC TCT GTG AGC ATT ATC 1344
Val Ser Met Phe Arg Ser Gly Phe Ser Asn Ser Ser Val Ser Ile Ile
        435                 440                 445

AGG GCC CCA ATG TTC TCC TGG ATT CAC CGT TCT GCT GAG TTC AAC AAC 1392
Arg Ala Pro Met Phe Ser Trp Ile His Arg Ser Ala Glu Phe Asn Asn
450                 455                 460

ATC ATT GCC TCT GAC AGC ATC ACT CAA ATC CCT GCT GTT AAG GGC AAC 1440
Ile Ile Ala Ser Asp Ser Ile Thr Gln Ile Pro Ala Val Lys Gly Asn
465                 470                 475                 480

TTC CTT TTC AAC GGC TCG GTC ATC TCG GGT CCA GGT TTC ACG GGT GGT 1488
Phe Leu Phe Asn Gly Ser Val Ile Ser Gly Pro Gly Phe Thr Gly Gly
                485                 490                 495

GAC CTT GTG CGC TTG AAC AGC TCG GGT AAC AAC ATC CAG AAC AGG GGT 1536
Asp Leu Val Arg Leu Asn Ser Ser Gly Asn Asn Ile Gln Asn Arg Gly
            500                 505                 510

TAC ATC GAG GTG CCA ATC CAC TTC CCA TCC ACC AGC ACC CGC TAC AGG 1584
Tyr Ile Glu Val Pro Ile His Phe Pro Ser Thr Ser Thr Arg Tyr Arg
        515                 520                 525

GTC AGG GTC AGG TAC GCT TCT GTG ACC CCA ATC CAC TTG AAC GTG AAC 1632
Val Arg Val Arg Tyr Ala Ser Val Thr Pro Ile His Leu Asn Val Asn
```

```
              530                 535                 540
TGG GGC AAC AGC TCC ATC TTC AGC AAC ACG GTG CCA GCC ACG GCC ACC 1680
Trp Gly Asn Ser Ser Ile Phe Ser Asn Thr Val Pro Ala Thr Ala Thr
545                 550                 555                 560

AGC CTT GAC AAC CTG CAG TCC TCG GAC TTC GGC TAC TTC GAA TCG GCC 1728
Ser Leu Asp Asn Leu Gln Ser Ser Asp Phe Gly Tyr Phe Glu Ser Ala
                565                 570                 575

AAC GCT TTC ACC AGC TCT CTT GGC AAC ATC GTG GGT GTG CGC AAC TTC 1776
Asn Ala Phe Thr Ser Ser Leu Gly Asn Ile Val Gly Val Arg Asn Phe
            580                 585                 590

TCT GGC ACG GCT GGT GTC ATC ATC GAC CGC TTC GAA TTC ATC CCA GTG 1824
Ser Gly Thr Ala Gly Val Ile Ile Asp Arg Phe Glu Phe Ile Pro Val
        595                 600                 605

ACG GCT ACC CTG GAG GCT GAG CCA CCA TAG                          1854
Thr Ala Thr Leu Glu Ala Glu Pro Pro
610                 615
```

(2) INFORMATION FOR SEQ ID NO:2:

(i) SEQUENCE CHARACTERISTICS:
        (A) LENGTH: 617 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
             100                 105                 110

Ser Phe Arg Glu Trp Glu Ala Asp Pro Thr Asn Pro Ala Leu Arg Glu
         115                 120                 125

Glu Met Arg Ile Gln Phe Asn Asp Met Asn Ser Ala Leu Thr Thr Ala
     130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                 165                 170                 175

Val Phe Gly Gln Arg Trp Gly Phe Asp Ala Ala Thr Ile Asn Ser Arg
             180                 185                 190

Tyr Asn Asp Leu Thr Arg Leu Ile Gly Asn Tyr Thr Asp Tyr Ala Val
         195                 200                 205

Arg Trp Tyr Asn Thr Gly Leu Glu Arg Val Trp Gly Pro Asp Ser Arg
     210                 215                 220

Asp Trp Val Arg Tyr Asn Gln Phe Arg Arg Glu Leu Thr Leu Thr Val
225                 230                 235                 240
```

```
Leu Asp Ile Val Ala Leu Phe Pro Asn Tyr Asp Ser Arg Arg Tyr Pro
                    245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
        450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
            595                 600                 605

Thr Ala Thr Leu Glu Ala Glu Pro Pro
            610                 615

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: unknown
```

(D) TOPOLOGY: unknown (ii) MOLECULE TYPE: DNA (genomic)

(xi) SEQUENCE DESCRIPTION: SEQ ID NO:3:

GGGGACTCTA GAGGATCCGG ATCCGTGACC ATGG                                  34

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

GGGGACTCTA GAGGATCCAG                                                  20

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

GACGGATCTG                                                             10

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:6:

GGGGACTCTA GAGGATCCAG                                                  20

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

GGGGACTCTA GAG                                                         13

(2) INFORMATION FOR SEQ ID NO:8:

(i) SEQUENCE CHARACTERISTICS:
        (A) LENGTH: 13 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:8:

CCGTCGACCA TGG                                                    13

(2) INFORMATION FOR SEQ ID NO:9:

(i) SEQUENCE CHARACTERISTICS:
        (A) LENGTH: 81 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:9:

CGAGCAGCTC ATCAACCAAC GCATTGAGGA GTTCGCTCGC AACCAAGCCA TCTCCAGGCT   60

TGAGGGCTTG AGCAACCTGT A                                            81

(2) INFORMATION FOR SEQ ID NO:10:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:10:

CAAGGCTAGG TTGGTTAGGT CAGCCTCCCA CTCCCTGAAG CTCTCAGCGT AGATTTGGTA   60

CAGGTTGCTC AAGCCCTC                                                78

(2) INFORMATION FOR SEQ ID NO:11:

(i) SEQUENCE CHARACTERISTICS:
        (A) LENGTH: 68 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:11:

CTTCGGCCCA AGCCAATGGG ACGCTTTCCT TGTGCAAATC GAGCAGCTCA TCAACCAACG   60

CATTGAGG                                                           68

(2) INFORMATION FOR SEQ ID NO:12:

(i) SEQUENCE CHARACTERISTICS:
        (A) LENGTH: 73 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:12:

GGCCGTGGTC AGAGCAGAGT TCATGTCGTT GAATTGGATG CGCATCTCCT CCCTCAAGGC   60

TAGGTTGGTT AGG                                                     73

(2) INFORMATION FOR SEQ ID NO:13:

(i) SEQUENCE CHARACTERISTICS:
        (A) LENGTH: 78 base pairs
        (B) TYPE: nucleic acid
        (C) STRANDEDNESS: unknown (D) TOPOLOGY: unknown (ii) MOLECULE TYPE: DNA (genomic)

(xi) SEQUENCE DESCRIPTION: SEQ ID NO:13:

TTCGT GCCAGGTGCT GGCTTCGTGC TTGGTCTAGT CGACATCATC TGGGGCATCT        60

TCGGCCCAAG CCAATGGG                                                 78

(2) INFORMATION FOR SEQ ID NO:14:

(i) SEQUENCE CHARACTERISTICS:
            (A) LENGTH: 79 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:14:

TGCACGTAGA CGCTCAGAAG AGGCACTTAG TAGTTCTGCA CAGCGAACAG AGGGATGGCC    60

GTGGTCAGAG CAGAGTTCA                                                79

(2) INFORMATION FOR SEQ ID NO:15:

(i) SEQUENCE CHARACTERISTICS:
            (A) LENGTH: 68 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:15:

ACACCCCAAT CGACATCTCT CTGAGCCTGA CCCAATTCCT GCTGTCTGAG TTCGTGCCAG    60

GTGCTGGC                                                            68

(2) INFORMATION FOR SEQ ID NO:16:

(i) SEQUENCE CHARACTERISTICS:
            (A) LENGTH: 87 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:16:

CGAAGCCCCA GCGTTGACCG AACACAGACA CGTCCCTCAA CACAGACAGG TGCAAGTTAG    60

CAGCTTGCAC GTAGACGCTC AGAAGAG                                       87

(2) INFORMATION FOR SEQ ID NO:17:

(i) SEQUENCE CHARACTERISTICS:
            (A) LENGTH: 61 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:17:

GAGGTGGAGG TGCTTGGTGG TCAGCGCATT GAGACCGGCT ACACCCCAAT CGACATCTCT    60

C                                                                   61

(2) INFORMATION FOR SEQ ID NO:18:

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:18:

CAGCCTGGTC AGGTCGTTGT AGCGAGAGTT GATGGTGGCA GCATCGAAGC CCCAGCGTTG 60

ACCG 64

(2) INFORMATION FOR SEQ ID NO:19:

(i) SEQUENCE CHARACTERISTICS:
        (A) LENGTH: 76 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:19:

CCATAGACAA CCCAAACATC AACGAGTGCA TCCCTTACAA CTGCTTGAGC AACCCTGAGG 60

TAGAGGTGCT TGGTGG 76

(2) INFORMATION FOR SEQ ID NO:20:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:20:

CCTCTCGAGG CCCGTGTTGT ACCAGCGCAC AGCGTAGTCC GTGTAGTTGC CAATCAGCCT 60

GGTCAGGTCG TTGTAGCG 78

(2) INFORMATION FOR SEQ ID NO:21:

(i) SEQUENCE CHARACTERISTICS:
        (A) LENGTH: 75 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:21:

CGCTCTCCTC ACCTGATGGA CATTCTTAAC AGCATCACTA TCTACACGGA CGCTCACCGC 60

GGCTACTACT ACTAG 75

(2) INFORMATION FOR SEQ ID NO:22:

(i) SEQUENCE CHARACTERISTICS:
        (A) LENGTH: 75 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:22:

```
   GAACTCTAGG CCAGAGAAAC CAACTAGGGA AGCCATGATT TGGTGGCCAG ACCAGTAGTA        60

GTAGCCGCGG TGAGC                                                        75

(2) INFORMATION FOR SEQ ID NO:23:

(i) SEQUENCE CHARACTERISTICS:
       (A) LENGTH: 78 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO:23:

TTGGAGAACT TCGATGGCTC CTTCAGGGGC TCTGCTCAAG GCATTGAGCG CAGCATTCGC        60

TCTCCTCACC TGATGGAC                                                     78

(2) INFORMATION FOR SEQ ID NO:24:

(i) SEQUENCE CHARACTERISTICS:
       (A) LENGTH: 82 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO:24:

GTTGAGCCAC AATGCGCTGT TGTGGAGCAG CGTTGCCCAT CGTACCGTAC AAAGGGAAGG        60

TGAACTCTGG GCCAGAGAAA CC                                                82

(2) INFORMATION FOR SEQ ID NO:25:

(i) SEQUENCE CHARACTERISTICS:
       (A) LENGTH: 83 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO:25:

CCCGTCGCTA CCCAATCCGC ACGGTGTCTC AGCTGACTAG GGAGATTTAC ACCAACCCAG        60

TTTTAGAGAA CTTCGATGGC TCC                                               83

(2) INFORMATION FOR SEQ ID NO:26:

(i) SEQUENCE CHARACTERISTICS:
       (A) LENGTH: 78 base pairs
       (B) TYPE: nucleic acid
       (C) STRANDEDNESS: unknown
       (D) TOPOLOGY: unknown (ii) MOLECULE TYPE: DNA (genomic)

(xi) SEQUENCE DESCRIPTION: SEQ ID NO:26:

GTTGAATAGG CGGCGGTACA AGGTGCTGGA AAGGGTGCGG TACACACCTT GGCCCAGTTG        60

AGCCACAATG CGCTGTTG                                                     78

(2) INFORMATION FOR SEQ ID NO:27:

(i) SEQUENCE CHARACTERISTICS:
       (A) LENGTH: 79 base pairs
       (B) TYPE: nucleic acid
```

(C) STRANDEDNESS: unknown
        (D) TOPOLOGY: unknown (ii) MOLECULE TYPE: DNA (genomic)

(xi) SEQUENCE DESCRIPTION: SEQ ID NO:27:

CCGCAGGGAG CTGACCCTGA CGGTGCTTGA CATTGTGGCT CTGTTCCCAA ACTACGACTC 60

CCGTCGCTAC CCAATCCGC                                              79

(2) INFORMATION FOR SEQ ID NO:28:

(i) SEQUENCE CHARACTERISTICS:
        (A) LENGTH: 75 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:28:

AAGCGAACTC AGTGCCATCA AGCACAGAAA GCTGTTGGTT GTTGATGCCA ATGTTGAATG 60

GGCGGCGGTA CAAGG                                                  75

(2) INFORMATION FOR SEQ ID NO:29:

(i) SEQUENCE CHARACTERISTICS:
        (A) LENGTH: 75 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:29:

GGCCTCGAGA GGGTGTAGGG TCCAGACTCC AGGGACTAGG TGCGTTACAA CCAATTCCGC 60

AGGGAGCTGA CCCTG                                                  75

(2) INFORMATION FOR SEQ ID NO:30:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:30:

GTCCACGGTA CCAGACTTGC GGTACACAGC GCTTAGCAAG TTGCTAGAGG TGCCGTAAGC 60

GAACTCAGTG CCATCAAG                                               78

(2) INFORMATION FOR SEQ ID NO:31:

(i) SEQUENCE CHARACTERISTICS:
        (A) LENGTH: 81 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:31:

GTCATCTCGG GTCCAGGTTT CACGGGTGGT GACCTTGTGC GCTTGAACAG CTCGGGTAAC 60

AACATCCAGA ACAGGGGTTA C                                           81

(2) INFORMATION FOR SEQ ID NO:32:

(i) SEQUENCE CHARACTERISTICS:
        (A) LENGTH: 79 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:32:

ACCTGACCCT GACCCTGTAG CGGGTGCTAG TAGATGGGAA GTGGATTGGC ACCTCGATGT  60

AACCCCTGTT CTGGATGTT                                              79

(2) INFORMATION FOR SEQ ID NO:33:

(i) SEQUENCE CHARACTERISTICS:
        (A) LENGTH: 81 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:33:

GCCTCTGACA GCATCACTCA AATCCCTGCT GTTAAGGGCA ACTTCCTTTT CAACGGCTCG  60

GTCATCTCGG GTCCAGGTTT C                                           81

(2) INFORMATION FOR SEQ ID NO:34:

(i) SEQUENCE CHARACTERISTICS:
        (A) LENGTH: 84 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:34:

GTTGCTGAAG ATGGAGCTGT TGCCCCAGTT CACGTTCAAG TGGATTAGGG TGGTCACAGA  60

AGCGTACCTG ACCCTGACCC TGTA                                        84

(2) INFORMATION FOR SEQ ID NO:35:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:35:

ATCAGGGCCC CAATGTTCTC CTAGATTCAC CGTTCTGCTG AGTTCAACAA CATCATTGCC  60

TCTGACAGCA TCACTCAA                                               78

(2) INFORMATION FOR SEQ ID NO:36:

(i) SEQUENCE CHARACTERISTICS:
        (A) LENGTH: 82 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:36:

CGAAGTAGCC GAAGTCCGAG GACTGCAGGT TGTCAAGGCT AGTAGCCGTA GCTGGCACCG 60

TGTTGCTGAA GATAGAGCTG TT                                          82

(2) INFORMATION FOR SEQ ID NO:37:

(i) SEQUENCE CHARACTERISTICS:
        (A) LENGTH: 78 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:37:

CACCGCTTGA GCCACGTTTC CATGTTCCGT TCGGGCTTCA GCAACAGCTC TGTGAGCATT 60

ATCAGGGCCC CAATGTTC                                               78

(2) INFORMATION FOR SEQ ID NO:38:

(i) SEQUENCE CHARACTERISTICS:
        (A) LENGTH: 69 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:38:

GCGCACACCC ACGATGTTGC CAAGAGAGCT GGTGAAAGCG TTGGCCGATT CGAAGTAGCC 60

GAAGTCCGA                                                         69

(2) INFORMATION FOR SEQ ID NO:39:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:39:

CCACAGAACA CAACGTGCC ACCTCGCCAA GGCTTCTCTC ACCGCTTGAG CCACGTTTCC 60

(2) INFORMATION FOR SEQ ID NO:40:

(i) SEQUENCE CHARACTERISTICS:
        (A) LENGTH: 71 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:40:

GGGATGAATT CGAAGCGGTC GATGATGACA CCAGCCGTGC CAGAGAAGTT GCGCACACCC 60

ACGATGTTGC C                                                      71

(2) INFORMATION FOR SEQ ID NO:41:

(i) SEQUENCE CHARACTERISTICS:
        (A) LENGTH: 60 base pairs
        (B) TYPE: nucleic acid
        (C) STRANDEDNESS: unknown (D) TOPOLOGY: unknown (ii) MOLECULE TYPE: DNA (genomic)

(xi) SEQUENCE DESCRIPTION: SEQ ID NO:41:

CGCAAGTCTG GTACCGTGGA CAGCTTGGAC GAGATCCCTC CACAGAACAA CAACGTGCCA 60

(2) INFORMATION FOR SEQ ID NO:42:

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:42:

CTCTAGATCC CTATGGTGGC TCAGCCTCCA GGGTAGCCGT CACTGGGATG AATTCGAAGC 60

GGTC                                                               64

(2) INFORMATION FOR SEQ ID NO:43:

(i) SEQUENCE CHARACTERISTICS:
        (A) LENGTH: 1030 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:43:

AAGCTTGCAT GCCTGCAGAT CTGCATGGGT GGAGACTTTT CAACAAAGGG TAATATCCGG 60

AAACCTCCTC GGATTCCATT GCCCAGCTAT CTGTCACTTT ATTGTGAAGA TAGTGGAAA 120

GGAAGGTGGC TCCTACAAAT GCCATCATTG CGATAAAGGA AAGGCCATCG TTGAAGATG 180

CTCTGCCGAC AGTGGTCCCA AGATGGACC CCCACCCACG AGGAGCATCG TGGAAAAAG 240

AGACGTTCCA ACCACGTCTT CAAAGCAAGT GGATTGATGT GATCATCGAT GGAGACTTT 300

CAACAAAGGG TAATATCCGG AAACCTCCTC GGATTCCATT GCCCAGCTAT CTGTCACTT 360

ATTGTGAAGA TAGTGGAAAA GGAAGGTGGC TCCTACAAAT GCCATCATTG CGATAAAGG 420

AAGGCCATCG TTGAAGATGC CTCTGCCGAC AGTGGTCCCA AGATGGACC CCCACCCAC 480

AGGAGCATCG TGGAAAAAGA AGACGTTCCA ACCACGTCTT CAAAGCAAGT GGATTGATG 540

GATATCTCCA CTGACGTAAG GGATGACGCA CAATCCCACT ATCCTTCGCA AGACCCTTC 600

TCTATATAAG GAAGTTCATT TCATTTGGAG AGAACACGGG GGACTCTAGA GGATCCAGC 660

GAAGGCTCGA CAAGGCAGTC CACGGAGGAG CTGATATTTG GTGGACAAGC TGTGGATAG 720

AGCAACCCTA TCCCTAATAT ACCAGCACCA CCAAGTCAGG GCAATCCCCA GATCAAGTG 780

AAAGGTCCGC CTTGTTTCTC CTCTGTCTCT TGATCTGACT AATCTTGGTT TATGATTCG 840

TGAGTAATTT TGGGGAAAGC TCCTTTGCTG CTCCACACAT GTCCATTCGA ATTTTACCG 900

GTTTAGCAAG GGCGAAAAGT TTGCATCTTG ATGATTTAGC TTGACTATGC GATTGCTTT 960

CTGGACCCGT GCAGCTGCGC TCGGATCTGG GGCCATTTGT TCCAGGCACG GGATAAGC 1020

TCAGCCATGG                                                        1030

(2) INFORMATION FOR SEQ ID NO:44:

(i) SEQUENCE CHARACTERISTICS:
        (A) LENGTH: 380 base pairs (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:44:

GGATCCAGCT GAAGGCTCGA CAAGGCAGTC CACGGAGGAG CTGATATTTG GTGGACAAGC    60

TGTGGATAGG AGCAACCCTA TCCCTAATAT ACCAGCACCA CCAAGTCAGG GCAATCCCC   120

GATCAAGTGC AAAGGTCCGC CTTGTTTCTC CTCTGTCTCT TGATCTGACT AATCTTGGT   180

TATGATTCGT TGAGTAATTT TGGGGAAAGC TCCTTTGCTG CTCCACACAT GTCCATTCG   240

ATTTTACCGT GTTTAGCAAG GGCGAAAAGT TTGCATCTTG ATGATTTAGC TTGACTATG   300

GATTGCTTTC CTGGACCCGT GCAGCTGCGC TCGGATCTGG GGCCATTTGT TCCAGGCAC   360

GGATAAGCAT TCAGCCATGG                                              380

(2) INFORMATION FOR SEQ ID NO:45:

(i) SEQUENCE CHARACTERISTICS:
            (A) LENGTH: 167 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:45:

GGATCCAGCT GAAGGCTCGA CAAGGCAGTC CACGGAGGAG CTGATATTTG GTGGACAAGC    60

TGTGGATAGG AGCAACCCTA TCCCTAATAT ACCAGCACCA CCAAGTCAGG GCAATCCCG   120

GATCTCGGGC CATTTGTTCC AGGCACGGGA TAAGCATTCA GCCATGG                167

(2) INFORMATION FOR SEQ ID NO:46:

(i) SEQUENCE CHARACTERISTICS:
            (A) LENGTH: 1196 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:46:

AAGCTTGCAT GCCTGCAGAT CTGCATGGGT GGAGACTTTT CAACAAAGGG TAATATCCGG    60

AAACCTCCTC GGATTCCATT GCCCAGCTAT CTGTCACTTT ATTGTGAAGA TAGTGGAAA   120

GGAAGGTGGC TCCTACAAAT GCCATCATTG CGATAAAGGA AAGGCCATCG TTGAAGATG   180

CTCTGCCGAC AGTGGTCCCA AGATGGACC CCCACCCACG AGGAGCATCG TGGAAAAAG    240

AGACGTTCCA ACCACGTCTT CAAAGCAAGT GGATTGATGT GATCATCGAT GGAGACTTT   300

CAACAAAGGG TAATATCCGG AAACCTCCTC GGATTCCATT GCCCAGCTAT CTGTCACTT   360

ATTGTGAAGA TAGTGGAAAA GGAAGGTGGC TCCTACAAAT GCCATCATTG CGATAAAGG   420

AAGGCCATCG TTGAAGATGC CTCTGCCGAC AGTGGTCCCA AGATGGACC CCCACCCAC    480

AGGAGCATCG TGGAAAAAGA AGACGTTCCA ACCACGTCTT CAAAGCAAGT GGATTGATG   540

GATATCTCCA CTGACGTAAG GGATGACGCA CAATCCCACT ATCCTTCGCA AGACCCTTC   600

TCTATATAAG GAAGTTCATT TCATTTGGAG AGAACACGGG GGACTCTAGA GGATCCAGC   660

GAAGGCTCGA CAAGGCAGTC CACGGAGGAG CTGATATTTG GTGGACAAGC TGTGGATAG   720

AGCAACCCTA TCCCTAATAT ACCAGCACCA CCAAGTCAGG GCAATCCCCA GATCACCCC   780

```
GCAGATTCGA AGAAGGTACA GTACACACAC ATGTATATAT GTATGATGTA TCCCTTCGA 840

CGAAGGCATG CCTTGGTATA ATCACTGAGT AGTCATTTTA TTACTTTGTT TTGACAAGT 900

AGTAGTTCAT CCATTTGTCC CATTTTTTCA GCTTGGAAGT TTGGTTGCAC TGGCACTTG 960

TCTAATAACT GAGTAGTCAT TTTATTACGT TGTTTCGACA AGTCAGTAGC TCATCCAT 1020

GTCCCATTTT TTCAGCTAGG AAGTTTGGTT GCACTGGCCT TGGACTAATA ACTGATTA 1080

CATTTTATTA CATTGTTTCG ACAAGTCAGT AGCTCATCCA TCTGTCCCAT TTTTCAGC 1140

GGAAGTTCGG ATCTGGGGCC ATTTGTTCCA GGCACGGGAT AAGCATTCAG CCATGG    1196
```

(2) INFORMATION FOR SEQ ID NO:47:

(i) SEQUENCE CHARACTERISTICS:
        (A) LENGTH: 219 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:47:

```
TGATCAAGTG CAAAGGTCCG CCTTGTTTCT CCTCTGTCTC TTGATCTGAC TAATCTTGGT  60

TTATGATTCG TTGAGTAATT TTGGGGAAAG CTCCTTTGCT GCTCCACACA TGTCCATTC  120

AATTTTACCG TGTTTAGCAA GGGCGAAAAG TTTGCATCTT GATGATTTAG CTTGACTAT  180

CGATTGCTTT CCTGGACCCG TGCAGCTGCG CTCGGATCC                        219
```

(2) INFORMATION FOR SEQ ID NO:48:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:48:

```
CAGATCTGCA GATCTGCATG GGCGATG                                      27
```

(2) INFORMATION FOR SEQ ID NO:49:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:49:

```
GGGGACTCTA GAGGATCCCC GGGTGGTCAG TCCCTT                            36
```

(2) INFORMATION FOR SEQ ID NO:50:

(i) SEQUENCE CHARACTERISTICS:
        (A) LENGTH: 10 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:50:

```
       GAATTTCCCC                                                            10

(2) INFORMATION FOR SEQ ID NO:51:

(i) SEQUENCE CHARACTERISTICS:
         (A) LENGTH: 12 base pairs
         (B) TYPE: nucleic acid
         (C) STRANDEDNESS: unknown
         (D) TOPOLOGY: unknown (ii) MOLECULE TYPE: DNA (genomic)

(xi) SEQUENCE DESCRIPTION: SEQ ID NO:51:

GATCCGGATC CG                                                         12

(2) INFORMATION FOR SEQ ID NO:52:

(i) SEQUENCE CHARACTERISTICS:
         (A) LENGTH: 12 base pairs
         (B) TYPE: nucleic acid
         (C) STRANDEDNESS: unknown
         (D) TOPOLOGY: unknown (ii) MOLECULE TYPE: DNA (genomic)

(xi) SEQUENCE DESCRIPTION: SEQ ID NO:52:

TCGACGGATC CG                                                         12

(2) INFORMATION FOR SEQ ID NO:53:

(i) SEQUENCE CHARACTERISTICS:
         (A) LENGTH: 29 base pairs
         (B) TYPE: nucleic acid
         (C) STRANDEDNESS: unknown
         (D) TOPOLOGY: unknown (ii) MOLECULE TYPE: DNA (genomic)

(xi) SEQUENCE DESCRIPTION: SEQ ID NO:53:

GGGGACTCTA GAGGATCCCG AATTTCCCC                                       29

(2) INFORMATION FOR SEQ ID NO:54:

(i) SEQUENCE CHARACTERISTICS:
         (A) LENGTH: 57 base pairs
         (B) TYPE: nucleic acid
         (C) STRANDEDNESS: unknown
         (D) TOPOLOGY: unknown (ii) MOLECULE TYPE: DNA (genomic)

(xi) SEQUENCE DESCRIPTION: SEQ ID NO:54:

GATCCAGCTG AAGGCTCGAC AAGGCAGATC CACGGAGGAG CTGATATTTG GTGGACA        57

(2) INFORMATION FOR SEQ ID NO:55:

(i) SEQUENCE CHARACTERISTICS:
         (A) LENGTH: 57 base pairs
         (B) TYPE: nucleic acid
         (C) STRANDEDNESS: unknown
         (D) TOPOLOGY: unknown (ii) MOLECULE TYPE: DNA (genomic)

(xi) SEQUENCE DESCRIPTION: SEQ ID NO:55:

AGCTTGTCCA CCAAATATCA GCTCCTCCGT GGATCTGCCT TGTCCAGCCT TCAGCTG        57

(2) INFORMATION FOR SEQ ID NO:56:
```

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:56:

AGCTGTGGAT AGGAGCAACC CTATCCCTAA TATACCAGCA CCACCAAGTC AGGGCAATCC 60

CGGG                                                                64

(2) INFORMATION FOR SEQ ID NO:57:

(i) SEQUENCE CHARACTERISTICS:
        (A) LENGTH: 64 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:57:

TCGACCCGGG ATTGCCCTGA CTTGGTGGTG CTGGTATATT AGGGATAGGG TTGCTCCTAT 60

CCAC                                                                64

(2) INFORMATION FOR SEQ ID NO:58:

(i) SEQUENCE CHARACTERISTICS:
        (A) LENGTH: 62 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:58:

CCGGGCCATT TGTTCCAGGC ACGGGATAAG CATTCAGCCA TGGGATATCA AGCTTGGATC 60

CC                                                                  62

(2) INFORMATION FOR SEQ ID NO:59:

(i) SEQUENCE CHARACTERISTICS:
        (A) LENGTH: 62 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:59:

TCGAGGGATC CAAGCTTGAT ATCCCATGGC TGAATGCTTA TCCCGTGCCT GGAACAAATG 60

GC                                                                  62

(2) INFORMATION FOR SEQ ID NO:60:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:60:

```
    GATATCAAGC TTGGATCCC                                                    19
```

(2) INFORMATION FOR SEQ ID NO:61:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:61:

```
    CGGTACCTCG AGTTAAC                                                      17
```

(2) INFORMATION FOR SEQ ID NO:62:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:62:

```
    CATGGTTAAC TCGAGGTACC GAGCT                                             25
```

(2) INFORMATION FOR SEQ ID NO:63:

(i) SEQUENCE CHARACTERISTICS:
        (A) LENGTH: 13 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:63:

```
    ATCTGCATGG GTG                                                          13
```

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:64:

```
    GGGGACTCTA GAGGATCCAG                                                   20
```

(2) INFORMATION FOR SEQ ID NO:65:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:65:

```
    GTTAACTCGA GGTACCGAGC TCGAATTTCC CC                                     32
```

(2) INFORMATION FOR SEQ ID NO:66:

```
        (i) SEQUENCE CHARACTERISTICS:
            (A) LENGTH: 10 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:66:

CTAGAGGATC                                                      10

(2) INFORMATION FOR SEQ ID NO:67:

(i) SEQUENCE CHARACTERISTICS:
            (A) LENGTH: 10 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:67:

CATGGATCCT                                                      10

(2) INFORMATION FOR SEQ ID NO:68:

(i) SEQUENCE CHARACTERISTICS:
            (A) LENGTH: 12 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:68:

GATCGTGATC AC                                                   12

(2) INFORMATION FOR SEQ ID NO:69:

(i) SEQUENCE CHARACTERISTICS:
            (A) LENGTH: 28 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:69:

CTCGAGATCT AGATATCGAT GAATTCCC                                  28

(2) INFORMATION FOR SEQ ID NO:70:

(i) SEQUENCE CHARACTERISTICS:
            (A) LENGTH: 41 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:70:

TATGGATCCT GTGATAACCG ACATATGCCC CGGTTTCGTT G                   41

(2) INFORMATION FOR SEQ ID NO:71:

(i) SEQUENCE CHARACTERISTICS:
            (A) LENGTH: 12 base pairs
            (B) TYPE: nucleic acid
```

```
            (C) STRANDEDNESS: unknown
            (D) TOPOLOGY: unknown (ii) MOLECULE TYPE: DNA (genomic)

(xi) SEQUENCE DESCRIPTION: SEQ ID NO:71:

CAGATCTGTG CA                                                       12

(2) INFORMATION FOR SEQ ID NO:72:

(i) SEQUENCE CHARACTERISTICS:
            (A) LENGTH: 12 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:72:

AATTGAGATC TC                                                       12

(2) INFORMATION FOR SEQ ID NO:73:

(i) SEQUENCE CHARACTERISTICS:
            (A) LENGTH: 12 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:73:

AATTGAGATC TC                                                       12

(2) INFORMATION FOR SEQ ID NO:74:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:74:

TCCTGATCTG TGCAGGTCCC C                                             21

(2) INFORMATION FOR SEQ ID NO:75:

(i) SEQUENCE CHARACTERISTICS:
            (A) LENGTH: 37 base pairs
            (B) TYPE: nucleic acid
            (C) STRANDEDNESS: unknown
            (D) TOPOLOGY: unknown (ii) MOLECULE TYPE: DNA (genomic)

(xi) SEQUENCE DESCRIPTION: SEQ ID NO:75:

GGGGACTCTA GAGGATCCGG ATCCGTCGAC CATGGTC                            37

(2) INFORMATION FOR SEQ ID NO:76:

(i) SEQUENCE CHARACTERISTICS:
            (A) LENGTH: 27 base pairs
            (B) TYPE: nucleic acid
            (C) STRANDEDNESS: unknown
            (D) TOPOLOGY: unknown (ii) MOLECULE TYPE: DNA (genomic)
```

(xi) SEQUENCE DESCRIPTION: SEQ ID NO:76:

GGGGAATTGG AGAGCTCGAA TTTCCCC                                          27

(2) INFORMATION FOR SEQ ID NO:77:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:77:

GGGAATTGAG ATCAGGATCT CGAGCTCGGG                                       30

(2) INFORMATION FOR SEQ ID NO:78:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:78:

CAAGCTTGGC TGCAGGTC                                                    18

(2) INFORMATION FOR SEQ ID NO:79:

(i) SEQUENCE CHARACTERISTICS:
        (A) LENGTH: 11 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:79:

CTGTGATAAC C                                                           11

(2) INFORMATION FOR SEQ ID NO:80:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:80:

GGGAATTCAT CGATATCTAG ATCTCGAGCT CGGGGTACCG AGCTCGAATT C               51

(2) INFORMATION FOR SEQ ID NO:81:

(i) SEQUENCE CHARACTERISTICS:
        (A) LENGTH: 32 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:81:

CGACCTGATC ACCCCAGCAG ATTCGAAGAA GG                                    32

(2) INFORMATION FOR SEQ ID NO:82:

(i) SEQUENCE CHARACTERISTICS:
        (A) LENGTH: 35 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:82:

```
TTCAGTGGAT CCGAACTTCC TAGCTGAAAA ATGGG                            35
```

(2) INFORMATION FOR SEQ ID NO:83:

(i) SEQUENCE CHARACTERISTICS:
        (A) LENGTH: 385 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:83:

```
TGATCACCCC AGCAGATTCG AAGAAGGTAC AGTACACACA CATGTATATA TGTATGATGT 60

ATCCCTTCGA TCGAAGGCAT GCCTTGGTAT AATCACTGAG TAGTCATTTT ATTACTTTG 120

TTTGACAAGT CAGTAGTTCA TCCATTTGTC CCATTTTTTC AGCTTGGAAG TTTGGTTGC 180

CTGGCACTTG GTCTAATAAC TGAGTAGTCA TTTTATTACG TTGTTTCGAC AAGTCAGTA 240

CTCATCCATC TGTCCCATTT TTTCAGCTAG GAAGTTTGGT TGCACTGGCC TTGGACTAA 300

AACTGATTAG TCATTTTATT ACATTGTTTC GACAAGTCAG TAGCTCATCC ATCTGTCCC 360

TTTTTCAGCT AGGAAGTTCG GATCC                                      385
```

(2) INFORMATION FOR SEQ ID NO:84:

(i) SEQUENCE CHARACTERISTICS:
        (A) LENGTH: 546 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:84:

```
GGATCCAGCT GAAGGCTCGA CAAGGCAGTC CACGGAGGAG CTGATATTTG GTGGACAAGC 60

TGTGGATAGG AGCAACCCTA TCCCTAATAT ACCAGCACCA CCAAGTCAGG GCAATCCCC 120

GATCACCCCA GCAGATTCGA AGAAGGTACA GTACACACAC ATGTATATAT GTATGATGT 180

TCCCTTCGAT CGAAGGCATG CCTTGGTATA ATCACTGAGT AGTCATTTTA TTACTTTGT 240

TTGACAAGTC AGTAGTTCAT CCATTTGTCC CATTTTTTCA GCTTGGAAGT TGGTTGCA 300

TGGCACTTGG TCTAATAACT GAGTAGTCAT TTTATTACGT TGTTTCGACA AGTCAGTAG 360

TCATCCATCT GTCCCATTTT TTCAGCTAGG AAGTTTGGTT GCACTGGCCT TGGACTAAT 420

ACTGATTAGT CATTTATTA CATTGTTTCG ACAAGTCAGT AGCTCATCCA TCTGTCCCA 480

TTTTCAGCTA GGAAGTTCGG ATCTGGGCC ATTTGTTCCA GGCACGGGAT AAGCATTCA 540

CCATGG                                                          546
```

MODIFIED *BACILLUS THURINGIENSIS* GENE FOR LEPIDOPTERAN CONTROL IN PLANTS

This application claims the benefit of U.S. Provisional application Ser. No. 60/005,405, filed Oct. 13, 1995.

The present invention relates to the design, synthesis and expression in plants of a DNA sequence that encodes a *Bacillus thuringiensis* protein that is toxic to specific insects. More particularly, the invention is directed to a synthetic DNA sequence which is optimized for expression in plants, a vector containing the synthetic DNA sequence which is suitable for transforming plants, and plants which stably express the protein coded for by the synthetic DNA sequence.

BACKGROUND OF THE INVENTION

A widely used microbial pesticide is derived from the soil microbe *Bacillus thuringiensis* (Bt). Bt is a gram-positive, spore-forming bacterium characterized by parasporal crystalline protein inclusions. The crystal protein, often referred to as the δ-endotoxin, has two forms: a nontoxic protoxin with an approximate molecular weight (MW) of 130 kilodaltons (kD); and a toxic form having an approximate MW of 68 kD. The crystalline protein inclusions contain the protoxin protein which is activated in the gut of larvae of a number of insect species. During activation, the protoxin is cleaved, the toxic moiety residing in an amino-proximal 58–68 kD polypeptide. In vivo, the crystal is activated by being solubilized and converted to toxic form by the alkalinity and proteases of the insect gut.

The toxic activity of the protein produced by Bt is highly specific to particular insect species and is recognized as safe to higher vertebrates. Numerous reports have shown that the intrasporal crystal proteins isolated from many strains of Bt possess extremely high levels of toxicity specific for *Lepidopteran larvae*, or *Coleopteran larvae*, with an effective concentration required to inhibit 50% of larval growth in the range of 1 ng/ml of diet for the most sensitive insects (MacIntosh et al., *J. Invert. Pathol.* 565 (1990) 258).

The cloning, sequencing and expression of the Bt protein gene in other bacterial hosts has been described (International Publication No. WO 93/04587, EP Appln. No. 89300388.9, EP Appln. No. 90304996.3, and U.S. Pat. No. 5,286,485). However, expression of insecticidal protein genes derived from Bt in plants has been extremely difficult, and typically, only low levels of protein have been obtained in transgenic plants (Vaeck et al., *Nature,* 328 (1987) 33; Barton et al., *Plant Physiol.,* 85 (1987) 1103; and Fischoff et al., *Bio/Technology,* 5 (1987) 807).

One possible explanation for low expression of the native Bt gene in transgenic plants is that the codon usage in a native Bt protein gene is significantly different from that of a typical plant gene (EP Appln. No. 89309069.6). Codon usage may influence the expression of genes at the level of translation, transcription or mRNA processing.

Another possible reason for low levels of expression of the native Bt gene in transgenic plants may be due to fortuitous transcription processing sites which produce aberrant forms of mRNA (International Publication No. WO 93/07278). Possible processing sites include polyadenylation sites, intron splicing sites, transcriptional termination signals and transport signals. Fortuitous occurrence of such processing sites in a coding region may complicate the expression of a gene in a transgenic host.

To optimize an insecticidal gene for expression in plants, attempts have been made to alter the native Bt gene to resemble, as much as possible, genes naturally contained within the host plant to be transformed. For example, U.S. Pat. No. 5,380,831 to Adang et al. describes a chemically synthesized gene encoding an insecticidal protein which is functionally equivalent to a native insecticidal protein of Bt, and which is designed to be expressed in plants at a level higher than a native Bt gene. The synthetic gene is at least approximately 85% homologous to a native insecticidal protein gene of Bt and is designed such that its distribution frequency of codon usage deviates no more than 25% of highly expressed plant genes, and preferably no more than about 10%. The synthetic gene has GC and TA doublet avoidance indices, based on the frequency in a host gene sequence, that deviates from that of the host plant by no more than about 10–15%, and has a GC content of about 45%.

International Publication No. WO 93/07278 describes a synthetic Bt crystal protein gene in which codon usage has been altered in order to increase expression in maize. The synthetic gene is at least approximately 66% homologous to a native insecticidal protein gene of Bt and 98% homologous to a pure maize optimized gene. The synthetic gene has a GC content of from 50–64% and does not have prolines at the 3' end of the sequence.

SUMMARY OF THE INVENTION

The present invention is directed to the design, synthesis, and expression in both bacterial and plant cells of a plant optimized DNA sequence that encodes a *Bacillus thuringiensis* HD73 protein which is toxic to Lepidopteran insects. The invention is further related to a method of designing a synthetic gene. The plant optimized DNA sequence comprises codons effective to encode an insecticidal plant protein (hereinafter ICP) with about 589 to about 619 amino acids. The nucleotide sequence coding for ICP is about 70 to about 71% homologous to a native Bt nucleotide sequence encoding ICP, and about 63% homologous to a pure maize nucleotide sequence. Codon usage in the plant optimized nucleotide sequence has a deviation from that of the host plant of about 0.23 to about 3.48, preferably about 1.075.

The present invention is also directed to plant expression vectors capable of expression in plant cells, such as maize. The plant expression vector comprising in sequence 5' to 3', a promoter sequence effective to initiate transcription in plant cells; a translational enhancer sequence specific to maize; a first vector unique restriction enzyme cleavage site; a coding sequence coding for a protein typically of less than about 620 amino acids, the protein preferably being substantially homologous with the amino-proximal portion of a Bt ICP; a second vector unique restriction enzyme cleavage site; and a polyadenylation sequence.

Another aspect of the invention is directed to a transgenic plant and seeds from a transgenic plant. The transgenic plant and seeds from a transgenic plant comprising in their genome the inheritable synthetic Bt gene described herein. This Bt synthetic gene is expressed in the cells of the plant or a plant grown from the seeds of the transgenic plant, in sufficient amounts to control lepidopteran insects.

The present invention also provides methods of engineering any structural gene so that it may be optimally expressed in plants, in particular maize. Due to the plasticity afforded by the redundancy of the genetic code (i.e. some amino acids are specified by more than one codon) the invention prescribes a method of modifying the genetic sequence of any gene so that the resulting protein that is expressed is unchanged, but the codons are modified to optimize the expression of the protein in the particular plant of interest.

In practicing the method of the invention, the codon bias of the plant is determined. The codon bias is the statistical codon distribution that the plant uses for coding its proteins. After determining the bias, the percent frequency of the codons in the gene of interest, such as a native Bacillus thuringiensis, is determined. The amino acid sequence of the protein of interest is reverse translated so that the resulting nucleic acid sequence codes for the same protein as the native gene, but the resulting nucleic acid sequence corresponds to the first preferred codons of the desired plant. The new sequence is analyzed for restriction enzyme sites that might have been created by the modification. The identified sites are further modified by replacing the codons with second or third choice preferred codons. Other sites in the sequence which could affect the transcription or translation of the gene of interest are the exon:intron 5' or 3' junctions, poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice. The method described above enables one skilled in the art to modify gene(s) that are foreign to a particular plant so that the genes are optimally expressed in plants.

It is an overall interest of the present invention to provide a means for protection of plants against insect damage. More specifically, it is of particular interest to provide a maize optimized nucleotide sequence coding for an insecticidal protein from Bt having the nucleotide sequence in SEQ. ID. NO. 1.

The invention further provides a doubly enhanced 35S or 19S promoter which expresses foreign proteins, including Bt crystal protein or Bt insecticidal crystal proteins more effectively than a 35S or 19S promoter as well as a MSV leader sequence that could be further modified for use with other promoters.

In another aspect, the invention provides a leader sequence which could be used to enhance the expression of any promoter.

Other aspects, advantages, features and characteristics of the present invention will become more apparent upon consideration of the following description and the appended claims.

BRIEF DESCRIPTION OF THE FIGURES

FIGS. (1A–1B) illustrates the PCR synthesis strategy.

FIG. 1A is a graphic representation of the modified ICP gene with key restriction sites indicated above the bar, numbers underneath denote their locations in the gene. The three gene parts that were synthesized separately are shown underneath the gene, the cloning sites incorporated into the ends of each part are shown at the ends of each fragment. FIG. 1B sets forth the PCR synthesis of the 5' end fragment of the ICP gene. The 12 oligonucleotides used in the synthesis are indicated by arrows. The direction of the arrows correspond to the polarity of synthesis of the nascent DNA strand. The location of each oligonucleotide in the gene fragment is indicated between the parentheses, the reverse order of the nucleotide location of the bottom set of oligonucleotides indicates their reverse complementarity to the top (coding) strand of the gene.

FIG. 2 shows the resulting gel from the purification of ICP oligonucleotides by denaturing PAGE. ICP oligonucleotides Bt6 through Bt10 were fractionated by electrophoresis on 12% denaturing PAGE as described in Example 1. Oligonucleotide identities are shown above each lane, and the size of each (nucleotides) is shown below the lane. The mobilities of the tracking dyes xylene cyanol (XC) and bromophenol blue (BPB) are indicated on the right.

FIG. 3 shows a gel which illustrates the progression in the synthesis of the three ICP gene parts. For each section, products of PCR steps 1–6 (5' and 3' sections) or 1–5 (center section) are shown in the lanes marked 1–6 or 1–5, respectively. Each lane contains 5 μl of gel purified DNA from the previous PCR step. Unmarked lanes at the outside of the gel contain 100 bp ladder DNA size standards (GIBCO/BRL).

FIG. 4 shows a gel that illustrates the expression of ICP in *E. coli*. ICP expressed in *E. coli* cells from a cytoplasmic expression vector was analyzed by SDS-PAGE and Western blotting as described in Example 4. Lane 1 contains an amount of *E. coli* total cell protein corresponding to about a 50 ng pellet of protein extract of *E. coli* cells expressing the cytoplasmic expression vector; lane 2 contains about 50 ng of cytoplasmic expression vector extract pellet; lane 3 contains about 10 ng of pellet extract. The negative control lane 4 contains 100 ng of extract pellet of *E. coli* cells expressing pET-9d. Lanes 5, 6 and 7 contain 20, 50 and 100 ng, respectively, of purified native Bt ICP.

FIG. 5 is a graphical representation which sets forth the results of Manduca sexta bioassays. Feeding assays with 500 ng each of *E. coli* extract protein (pET 9d pellet), pellet protein from extract of cells containing the ICP cytoplasmic expression plasmid cytoplasmic expression vector (CEV pellet), cytoplasmic expression vector expressing cells (CEV cells), and native ICP (Bt protein) were carried out as described in Example 6. Larval weight and mortality were scored 4 days after placing neonate larvae on the diets.

FIG. 6 is a map of plasmid vector pDAB 910 as further described in Example 7.

FIG. 7 is a map of plasmid vector pDAB 911 as further described in Example 7.

FIG. 8 is a map of plasmid vector pDAB 917 as further described in Example 7.

FIG. 9 is a gel that illustrates the expression of ICP in transgenic MSD callus. ICP expressed in MSD callus isolates was detected by SDS-PAGE and western blotting as described in Example 8. Lanes 1 through 7 contain callus extracts of maize isolates obtained by transformation of MSD line #4 with plasmid pDAB 911; lane 8 contains callus extract of nontransformed MSD line #4; lanes 9 and 10 contain 10 and 1 ng, respectively, of purified ICP.

FIG. 10 is a map of plasmid vector pDAD303 as further described in Example 7.

FIG. 11 illustrates several maps of tested promoters in plasmids pKA882, PDAB305, pDAB310, pDAB348 and pDAB353. More specifically, pKA882 contains the native 35S promoter, as embodied within CaMV nts 6605 to 7439 (MCASTRAS), followed by Linker Sequence A (SEQ. ID. NO. 3)

```
XbaI  BamHI  BamHI SalI  NcoI GGGGAC TCTAGAGGATCCGGATCCGTGACCATGG
``` wherein the ATG (underlined) encoded within the Nco I recognition sequence is the GUS translational start codon. Transcripts from this promoter contain as the 5' untranslated leader sequence essentially the above polylinker sequence.

pDAB348 contains an enhanced 35S promoter with additional 3' sequences and embodied as nucleotides 7093 to 7344 of CaMV DNA, the linker sequence CATCGATG, nucleotides 7093 to 7439 of CaMV, followed by the Linker Sequence A from above.

pDAB305 contains an enhanced 35S promoter with additional 3' sequences and embodied as nucleotides 7093 to 7344 of CaMV DNA, the linker sequence CATCGATG, nucleotides 7093 to 7439 of CaMV, the linker sequence GGGGACTCTAGAGGATCCAG (SEQ. ID. NO. 4), nucleotides 167 to 186 of MSV, nucleotides 188 to 277 of MSV, a C residue followed by nucleotides 120 to 210 of maize Adh1.S, nucleotides 555 to 672 of maize Adh1.S, the linker sequence GACGGATCTG (SEQ. ID. NO. 5), nucleotides 278 to 317 of MSV, and a G residue that represents the final base of an Nco I recognition sequence CC<u>ATG</u>G. As above, the GUS translational start codon is part of the Nco I site. Transcripts from this promoter contain as the 5' untranslated leader essentially the MSV coat protein leader sequence, into which has been inserted a deleted version of the maize Adh1.S intron 1.

pDAB310 contains an enhanced 35S promoter with additional 3' sequences and embodied as nucleotides 7093 to 7344 of CaMV DNA, the linker sequence CATCGATG, nucleotides 7093 to 7439 of CaMV, the linker sequence GGGGACTCTAGAGGATCCAG (SEQ. ID. NO. 6), nucleotides 167 to 186 of MSV, nucleotides 188 to 317 of MSV, and a G residue that represents the final base of an Nco I recognition sequence, CC<u>ATG</u>G. As above, the GUS translational start codon is part of the Nco I site.

Transcripts from this promoter contain the 5' untranslated leader essentially the MSV coat protein leader sequence.

pDAB353 contains an enhanced 35S promoter with additional 3' sequences and embodied as nucleotides 7093 to 7344 of CaMV DNA, the linker sequence CATCGATG, nucleotides 7093 to 7439 of CaMV, the linker sequence GGGGACTCTAGAG (SEQ. ID. NO. 7), nucleotides 120 to 210 of maize Adh1.S, nucleotides 555 to 672 of maize Adh1.S, and the sequence CCGTCGACC<u>ATG</u>G (SEQ. ID. NO. 8). As above, the GUS translational start codon is part of the Nco I site. Transcripts from this promoter contain as the 5' untranslated leader essentially a deleted version of the maize Adh.S intron 1.

DETAILED DESCRIPTION OF THE INVENTION

Definitions

Figure 1:
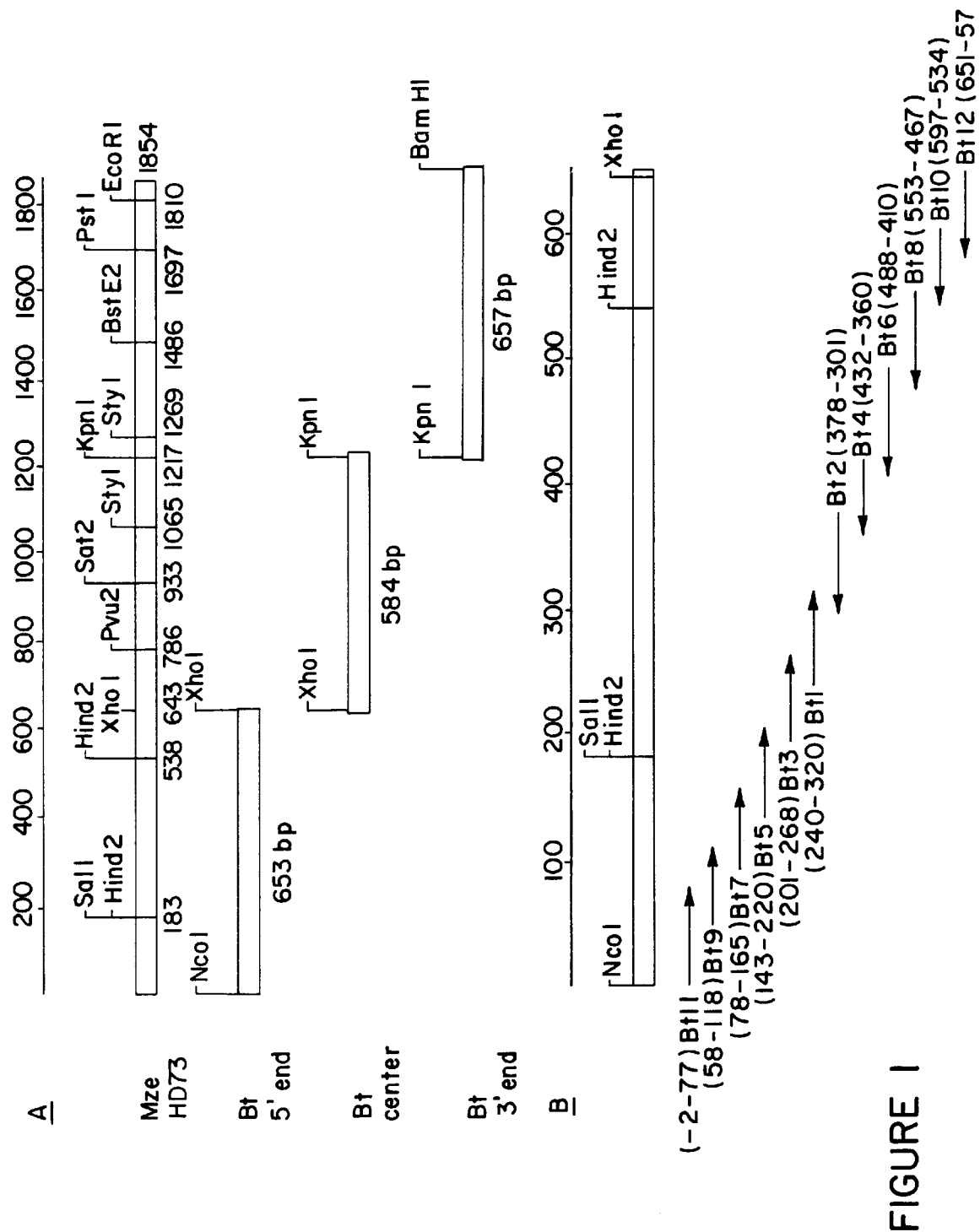

The following definitions are provided in order to provide clarity as to the intent or scope of their usage in the specification and claims. All patents and publications referred to herein are incorporated by reference herein.

Crystal protein or insecticidal crystal protein (ICP) or crystal toxin refers to the major protein component of the parasporal crystals formed in strains of Bt. This protein component exhibits selective toxicity to different species of insects. The molecular size of the major protein isolated from parasporal crystals varies depending on the strain of Bt from which it is derived. Crystal proteins having molecular weights of approximately 132, 65, and 28 kDa have been reported. It has been shown that the approximately 132 kDa protein is a protoxin that is cleaved to form an amino proximal insect toxin of approximately 65 kDa.

The crystal protein gene refers to the DNA sequence encoding the insecticidal crystal protein in either full length protoxin or toxin form, depending on the strain of Bt from which the gene is derived.

As used herein, the term nucleotide refers to monomeric unit of DNA or RNA consisting of a sugar moiety (pentose), a phosphate, and a nitrogenous heterocyclic base. The base is linked to the sugar moiety via the glycosidic carbon (1' carbon of the pentose). The combination of base and sugar is called a nucleoside; the base characterizes the nucleotide. The four DNA bases are adenine ("A"), guanine ("G"), cytosine ("C"), and thymine ("T"). The four RNA bases are A, G, C, and uracil ("U").

A structural gene is that portion of a gene comprising a DNA segment encoding a protein, polypeptide or a portion thereof, and excluding the 5' sequence which drives the initiation of transcription. The structural gene may be one which is normally found in the cell or one which is not normally found in the cellular location wherein it is introduced, in which case it is termed a heterologous gene. A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be a composite of segments derived from a plurality of sources (naturally occurring or synthetic, where synthetic refers to DNA that is chemically synthesized). The structural gene may also encode a fusion protein.

Operably linked refers to a juxtaposition wherein the components are configured so as to perform their usual function. Thus, control sequences operably linked to a coding sequence are capable of effecting the expression of the coding sequence.

Plant tissue includes differentiated and undifferentiated tissues of plants, including, but not limited to, roots, shoots, leaves, pollen, seeds, tumor tissue and various forms of cells in culture, such as single cells, protoplasts, embryos and callus tissue. The plant tissue may be in planta or in organ, tissue or cell culture.

Plant cell as used herein includes plant cells in planta and plant cells and protoplasts in culture.

Homology refers to identity or near identity of nucleotide or amino acid sequences. As is understood in the art, nucleotide mismatches can occur at the third or wobble base in the codon without causing amino acid substitutions in the final polypeptide sequence. Also, minor nucleotide modifications (e.g., substitutions, insertions or deletions) in certain regions of the gene sequence can be tolerated whenever such modifications result in changes in amino acid sequence that do not alter functionality of the final product. It has been shown that chemically synthesized copies of whole, or parts of, gene sequences can replace the corresponding regions in the natural gene without loss of gene function. Homologs of specific DNA sequences may be identified by those skilled in the art using the test of cross-hybridization of nucleic acids under conditions of stringency as is well understood in the art (as described in Hames et al., *Nucleic Acid Hybridisation*, (1985) IRL Press, Oxford, UK). Extent of homology is often measured in terms of percentage of identity between the sequences compared.

Preferred codon or frequency of preferred codon usage refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. The frequency of preferred codon usage exhibited by a host cell can be calculated by averaging the frequency of preferred codon usage in a large number of genes expressed by the host cell.

The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms the overall average deviation of the codon usage of a synthetic gene from that of a host cell is calculated using the equation $$A = \sum_{n=1}^{Z} \frac{\frac{|X_n - Y_N|}{X_N} \times 100}{Z}$$

where $X_n$=frequency of usage for codon n in the host cell; $Y_n$=frequency of usage for codon n in the synthetic gene; where n represents an individual codon that specifies an amino acid; and where the total number of codons is Z.

The term pure plant optimized nucleotide sequence refers to a gene or DNA sequence comprising 100% of the host plant preferred codon sequences for a particular polypeptide. A pure maize optimized sequence is a gene or DNA sequence which comprises 100% of the maize preferred codon sequence for a particular polypeptide.

As used herein, a plant optimized nucleotide sequence refers to a gene or DNA sequence produced from variations of the pure plant optimized sequence. The variations as described herein include alterations of the pure plant optimized nucleotide sequence to permit manipulation of the gene, such as by altering a nucleotide to create or eliminate restriction sites; and variations to eliminate potentially deleterious processing sites, such as potential polyadenylation sites or intron splicing recognition sites. A maize optimized nucleotide sequence refers to a gene or DNA sequence produced from variations of a pure maize optimized sequence. In one aspect of the invention, the plant optimized nucleotide sequence is about 70 to about 71% homologous with a native Bt nucleotide sequence encoding ICP, and about 63% homologous based on first choice codon usage and about 83% homologous to a pure maize optimized nucleotide sequence.

Derived from is used to mean taken, obtained, received, traced, replicated or descended from a source (chemical and/or biological). A derivative may be produced by chemical or biological manipulation (including, but not limited to, substitution, addition, insertion, deletion, extraction, isolation, mutation and replication) of the original source.

Chemically synthesized, as related to a sequence of DNA, means that the component nucleotides were assembled in vitro. Manual chemical synthesis of DNA may be accomplished using well established procedures (Caruthers, *Methodology of DNA and RNA Sequencing*, (1983), Weissman (ed.), Praeger Publishers, New York, Chapter 1); automated chemical synthesis can be performed using one of a number of commercially available machines.

The term designed to be highly expressed as used herein refers to a level of expression of a designed gene wherein the amount of its full-length specific mRNA transcripts produced is sufficient to be quantified in Northern blots and, thus, represents a level of specific mRNA expressed corresponding to greater than or equal to approximately 0.001% of the poly(A)+mRNA. Before this invention, natural Bt genes were transcribed at levels wherein the amount of full-length specific mRNA produced was insufficient to be estimated using the Northern blot technique. However, in the present invention, transcription of a synthetic maize optimized Bt ICP gene designed to be highly expressed, is increased to the extent that sufficiently high levels of the ICP accumulate to kill feeding insects.

Design of a Maize Optimized Bt ICP Gene Sequence

The design and synthesis strategy set forth herein represents the generally preferred methods for design and synthesis of a plant, specifically maize, optimized ICP gene. Those of ordinary skill in the art will recognize that changes to this protocol are possible without undue experimentation to design and synthesize an ICP gene for expression in other plant species.

The DNA sequence of the ICP gene from Bacillus thuringiensis subsp. kurstaki HD73, as reported by Adang et al., *Gene*, 36 (1985) 289, was used as a starting sequence for the design of a maize optimized Bt ICP gene. The resulting maize optimized Bt ICP gene is identified in SEQ. ID. NO. 1. The maize specific optimized insecticidal gene sequence contains about 63% first choice codons, between about 22% to about 37% second choice codons and between about 15% to about 0% third and/or fourth choice codons, wherein the total percentage is 100%. More preferably, the maize specific optimized insecticidal gene sequence contains about 63% first choice codons, between about 22% to about 37% second choice codons, and between 15% and 0% third choice codons, wherein the total percentage is 100%. Most preferably, the maize specific optimized insecticidal gene sequence contains about 63% first choice codons, at least about 22% second choice codons, about 7.5% third choice codons, and about 7.5% fourth choice codons, wherein the total percentage is 100%.

More specifically, *B. thuringiensis* CrylA(c) was used as the starting material. Analysis of the base composition of the native gene reveals significant disparity from maize genes. For example, the guanosine plus cytosine (G+C) composition of the native ICP gene is 37%, whereas maize genes fall into the G+C range of 45–75% (Table 1).

TABLE 1

Compilation of G + C contents of protein coding regions of maize genes

| Protein Class[a] | Range % G + C | Mean % G + C[b] |
|---|---|---|
| Metabolic Enzymes (40) | 44.4–75.3 | 59.0 (8.0) |
| Storage Proteins | | |
| Group I (23) | 46.0–51.9 | 48.1 (1.3) |
| Group II (13) | 60.4–74.3 | 67.5 (3.2) |
| Group I + II (36) | 46.0–74.3 | 55.1 (9.6)[c] |
| Structural Proteins (18) | 48.6–70.5 | 63.6 (6.7) |
| Regulatory Proteins (5) | 57.2–68.9 | 62.0 (4.9) |
| Uncharacterized Proteins (9) | 51.5–70.3 | 64.3–(7.2) |
| All Proteins (108) | 44.4–75.3 | 60.8 (5.2) |

[a]Numbers of genes in class given in parentheses.
[b]Standard deviations given in parentheses.
[c]Combined groups mean ignored in calculation of overall mean.

For the data in Table 1, coding regions of the genes were extracted from GenBank (Release 71) entries, and base compositions were calculated using the MacVector™ program (IBI, New Haven, Conn.). Intron sequences were ignored in the calculations. Group I and II storage protein gene sequences were distinguished by their marked difference in base composition.

The very low G+C content of the native Bt ICP gene (and consequent skewing towards high A+T content) results in the generation of sequences mimicking or duplicating plant gene control sequences that are known to be highly A+T rich. The presence of some A+T-rich sequences within the DNA of the introduced gene (e.g. TATA box regions normally found in gene promoters) may result in aberrant transcription of the gene. On the other hand, the presence of other regulatory sequences residing in the transcribed mRNA (e.g. polyadenylation signal sequences (AAUAAA), or sequences complementary to small nuclear RNAs involved in pre-mRNA splicing) may lead to RNA instability. Therefore, one goal in the design of a maize optimized Bt ICP gene was to generate a DNA sequence having a higher G+C content, and preferably one close to that of maize genes coding for metabolic enzymes. Another goal in the design of the maize optimized Bt ICP gene was to generate a DNA sequence that not only has a higher G+C content, but by modifying sequence changes should be made so as to not hinder translation.

Due to the plasticity afforded by the redundancy of the genetic code (i.e. some amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a gene's mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by the synthesis of low levels of the encoded protein.

A comparison of the codon composition of the Bt ICP gene and the codon compositions of maize genes (Table 2) reveals a large disparity in codon bias.

TABLE 2

Comparison of codon usage between 26 maize genes and a gene encoding a *Bacillus thuringiensis* Cry1A(c) protein[a]

| Amino Acid | Codon[a] | Maize[b] % | Bt[b] % |
|---|---|---|---|
| Gly | GGG | 16 | 22 |
| Gly | GGA | 13 | 40 |
| Gly | GGT | 21 | 28 |
| Gly | GGC | 50 | 10 |
| Glu | GAG | 81 | 21 |
| Glu | GAA | 19 | 79 |
| Asp | GAT | 24 | 75 |
| Asp | GAC | 76 | 25 |
| Val | GTG | 40 | 20 |
| Val | GTA | 6 | 40 |
| Val | GTT | 17 | 30 |
| Val | GTC | 37 | 10 |
| Ala | GCG | 24 | 23 |

TABLE 2-continued

Comparison of codon usage between 26 maize genes and a gene encoding a *Bacillus thuringiensis* Cry1A(c) protein[a]

| Amino Acid | Codon[a] | Maize[b] % | Bt[b] % |
|---|---|---|---|
| Ala | GCA | 13 | 26 |
| Ala | GCT | 27 | 39 |
| Ala | GCC | 36 | 12 |
| Arg | AGG | 26 | 14 |
| Arg | AGA | 7 | 42 |
| Arg | CGG | 13 | 1 |
| Arg | CGA | 3 | 14 |
| Arg | CGT | 11 | 25 |
| Arg | CGC | 40 | 4 |
| Ser | AGT | 5 | 27 |
| Ser | AGC | 28 | 7 |
| Ser | TCG | 16 | 13 |
| Ser | TCA | 10 | 20 |
| Ser | TCT | 14 | 18 |
| Ser | TCC | 27 | 15 |
| Lys | AAG | 90 | 32 |
| Lys | AAA | 10 | 68 |
| Asn | AAT | 19 | 72 |
| Asn | AAC | 81 | 28 |
| Met | ATG | 100 | 100 |
| Ile | ATA | 8 | 24 |
| Ile | ATT | 24 | 53 |
| Ile | ATC | 68 | 23 |
| Thr | ACG | 26 | 22 |
| Thr | ACA | 11 | 39 |
| Thr | ACT | 16 | 22 |
| Thr | ACC | 47 | 17 |
| Trp | TAG | 100 | 100 |
| End | TGA | 26 | 0 |
| End | TAG | 52 | 100 |
| End | TAA | 22 | 0 |
| Cys | TGT | 21 | 62 |
| Cys | TGC | 79 | 38 |
| Tyr | TAT | 14 | 81 |
| Tyr | TAC | 86 | 19 |
| Leu | TTG | 13 | 9 |
| Leu | TTA | 3 | 42 |
| Leu | CTG | 31 | 9 |
| Leu | CTA | 9 | 18 |
| Leu | CTT | 16 | 16 |
| Leu | CTC | 28 | 6 |
| Phe | TTT | 20 | 80 |
| Phe | TTC | 80 | 20 |
| Gln | CAG | 59 | 13 |
| Gln | CAA | 41 | 87 |
| His | CAT | 29 | 82 |
| His | CAC | 71 | 18 |
| Pro | CCG | 27 | 21 |
| Pro | CCA | 23 | 49 |
| Pro | CCT | 20 | 26 |
| Pro | CCC | 30 | 4 |

[a]Maize codon usage adapted from Murray et al. (Nucl. Acids Res., 17 (1989) 477). A compilation of 62 maize genes (Wada et al., Nucl. Acids Res., 18 (1990) 2367) indicated the same most commonly used codons, although differences between extremes were lessened.
[b]Numbers represent the frequencies at which each codon appears in a gene sequence as a percentage of the total number of times that all codons for that particular amino acid occur. Underlined numbers signify the "preferred" codons for each organism or gene.

Without exception, any redundant codon present in the Bacillus gene is a nonpreferred maize codon. These differences in codon bias are particularly evident in those cases where only two codon choices exist (i.e. Glu, Asp, Lys, Asn, Cys, Tyr, Phe, Gln, and His).

In designing the maize optimized Bt ICP gene the amino acid sequence of ICP was reverse translated into a DNA sequence, utilizing a nonredundant genetic code established from the codon bias table compiled for maize gene DNA sequences. The resulting DNA sequence, which was completely homogeneous in codon usage, was further modified in five reiterations to establish a DNA sequence that, besides having a higher degree of codon diversity, also contained strategically placed restriction enzyme recognition sites, desirable base composition, and a lack of sequences that might interfere with transcription of the gene, or translation of the product mRNA.

Mze HD73 #1 trnc: Synthesis of an ICP gene with preferred maize codons. As a starting point for creating a new ICP gene sequence, a "Maize Genetic Code" was created, wherein each amino acid is specified by a unique codon chosen on the basis of the most commonly occurring maize codons from Table 2 (frequencies as underlined numerals in the "Maize %" columns). The native Bt ICP DNA sequence was translated into the corresponding protein sequence, and the amino-terminal 610 amino acids (which comprise the minimal insecticidal peptide of the ICP) were reverse-translated into a new DNA sequence based on the Maize Genetic Code. This sequence, designated Mze HD73 #1 trnc was therefore comprised entirely of "preferred" maize codons and had a G+C content of 66%, somewhat higher than a "typical" maize gene (Table 1). The new DNA sequence had 624 base changes from the native Bacillus ICP DNA sequence.

Mze HD73 #2 trnc: Elimination of enzyme recognition sites. The restriction enzymes BamH I, Bgl II, Bcl I, and Nco I are routinely used for the construction of gene expression cassettes. Therefore, it is preferable that a DNA sequence that encodes a protein of interest not contain recognition sites for these enzymes. Analysis of the DNA sequence of Mze HD73 #1 trnc revealed recognition sequences for three Bcl I sites, three Bgl I sites, two Bgl II sites, one BamH I site, and one Nco I site. Alteration of the DNA sequence in such a fashion as to eliminate these sites forces the use of codons that are not the "preferred" maize codons, but rather are second or lower choice codons. For example, nucleotide 249 of the sequence was changed from G to C, changing a leucine codon from CTG (the preferred maize codon, being present 31% of the time, Table 2), to CTC (the second most frequently used leucine codon, occurring 28% of the time). This single change eliminated a Bcl I recognition site and an overlapping Pvu II site. Twelve other changes and their rationales are given in Table 3.

TABLE 3

Changes made in Mze HD73 #1 trnc → Mze HD73 #2 trnc

| Position | Change | Rationale |
|---|---|---|
| 249 | G > C | Eliminate Bcl Ih site |
| 295 | C > A | Eliminate Bgl I site |
| 297 | C > G | Eliminate Bgl I site |
| 324 | G > A | Eliminate Bgl II site |
| 592 | C > A | Eliminate Bgl I site |
| 594 | C > G | Eliminate Bgl I site |
| 801 | C > T | Eliminate Bgl II site |
| 970 | A > T | Eliminate Bgl I site |
| 971 | G > C | Eliminate Bgl I site |
| 1020 | C > G | Eliminate Nco I site |
| 1368 | C > T | Eliminate BamH I site |
| 1461 | G > C | Eliminate Bcl I site |
| 1794 | G > C | Eliminate Bcl I site |

The resulting sequence was designated Mze HD73 #2 trnc, and encoded the identical protein as Mze HD73 #1 trnc.

Analysis of the sequence revealed no recognition sites for BamH I, Bgl II, Bcl I, Nco I, or several other commonly used enzymes. The analysis also revealed that the ICP coding strand of Mze HD73 #2 trnc contains an entire Open Reading Frame (ORF) in reading frames 1 and 3. The ORF in frame 1 corresponds to that of the ICP, and verifies that no stop codons were inadvertently generated by the changes made to the sequence. The single ORF in frame 3 begins with the G of the ICP start codon, and continues uninterrupted to the end of the sequence.

Mze HD73 #3 trnc: Modification of enzyme recognition sites to facilitate synthesis. Current technology (using a combination of automated and enzymatic DNA syntheses) has an upper limit in the range of a few hundred base pairs for the size of fragments that can be reasonably synthesized in vitro. Consequently, it was necessary to divide the 1830 bp of DNA sequence for the ICP into several sections, each one flanked by appropriate restriction enzyme recognition sequences. The spacing of these sites was such that the corresponding DNA fragments were of a size that could be easily synthesized and manipulated in vitro. Site introduction was accomplished by making 6 base changes in the sequence of Mze HD73 #2 (summarized in Table 4).

TABLE 4

Changes made in Mze HD73 #2 trnc → Mze HD73 #3 trnc

| Position | Change | Rationale |
|---|---|---|
| 645 | G > C | Create Xho I site |
| 841 | C > A | Eliminate Sst II site |
| 843 | C > G | Eliminate Sst II site |
| 1221 | G > C | Create Sal I site |
| 1531 | C > A | Eliminate Sst II site |
| 1533 | C > G | Eliminate Sst II site |

These changes were made to eliminate two of three Sst II sites (leaving an appropriately positioned, unique Sst II site), and to create new restriction enzyme recognition sites with appropriate spacing. Again, these changes did not alter the amino acid sequence of the encoded protein, and did not utilize any very low frequency maize codons. The strategy employed to identify the positions of the new sites was based on analysis of the codon usage frequencies (Table 2). Preferred or frequently used maize codon pairs were chosen that generated restriction sites when juxtaposed. For example, paired codons CTC (Leu) and GAG (Glu) form an Xho I recognition site (CTCGAG), and paired codons GTC (Val) and GAC (Asp) form a Sal I site (GTCGAC). Analysis of the ICP sequence identified a Leu/Glu pair at residues 215/216, and a Val/Asp pair at residues 407/408. Appropriate base substitutions were made to generate the recognition sequences at these sites (Table 4). Analysis of the sequence of this gene (Mze HD73 #3 trnc) revealed the same ORF's as in version #2.

A search of the DNA sequence of Mze HD73 #3 trnc with a plant consensus sequence for exon:intron 5' junctions [AG:GTAAGT] revealed a 4/8 match [GGTA] at 629–632, and 3/8 matches [GGT] at eight other positions. The (T) GGTA(C) at 629 could not be changed without changing the encoded amino acids, since the genetic code utilizes a unique Trp codon (TGG), and both codons for the following Tyr begin with TA [TAC and TAT]. However, the sequence GGTA is probably not sufficient to serve as a splice recognition site, since the 5' A residue of the consensus sequence is highly conserved in splice recognition sites for both plant and animal RNAs, and the GGTA sequence occurs in the *E. coli* β-glucuronidase coding region (which is expressed well in plant cells), and in exon 1 of maize alcohol dehydrogenase (Adh) 1. In addition, GGTA is found as part of all Kpn I recognition sites [GGTACC] which occur naturally in some plant genes, so it likely does not represent a potential splice donor site per se.

The Mze HD73 #3 trnc DNA sequence was then searched for sequences similar to or identical with the poly A addition site signal consensus AATAAA. A perfect match was found in the native ICP gene sequence, but no homology was found to this engineered sequence, or shorter versions of it (down to AATA) in Mze HD73 #3 trnc.

Sequences resembling an RNA polymerase II termination sequence were searched using the template CAN$_{7-9}$AGTNNAA, where N represents any of the four bases found in DNA. There were no matches at any level with N set 7 to 9.

It is thought that the formation of intrastrand self-complementary structures ("hairpins") in mRNAs inhibits the progression of ribosomes along the mRNA during translation, and that the hairpin formers CTTCGG and its same-strand complement CCGAAG are particularly disadvantageous. Two perfect matches of CTTCGG were found in Mze HD73 #3 trnc (at 201–206 and 1707–1712). However, there were no matches to CCGAAG, CCGAA, CGAAG, or CGAA. Since the importance of hairpins is uncertain, the ICP sequence was not examined for any other self-complementary sequence blocks.

Mze HD73 #3 trnc: Elimination of TA or GC doublets. Eukaryotic genes are relatively deficient in the nucleotide doublets TA and GC, and enriched in doublets TG and CT. Only two "preferred" maize codons (Table 2) contain TA or CG doublets: TAC (Tyr) and CGC (Arg). The use of these codons in the synthetic sequence necessitates the generation of doublets we wished to avoid. Therefore, the benefit of using the preferred codon must be balanced against the detriment of creating an overabundance of "forbidden" doublets. In the Tyr case, substitution by the second choice codon does not eliminate the TA doublet, since it is also a component of that codon (TAT). In the Arg case, however, the second choice codon (AGG) is used in maize only slightly less frequently than the first choice (26% vs 40% of the time), so the substitution of CGC by AGG was completed. The other codons that contain TA or CG doublets [GTA (Val); ATA (Ile); TAG, TAA (End); TTA, CTA (Leu); GCG (Ala); CGG, CGA, CGT (Art); ACG (Thr); and CCG (Pro)] are either not acceptable for use in coding regions (e.g. the stop codons), are found so infrequently in maize genes that they are not suitable for inclusion in a codon-biased sequence, or are members of codons sets that have acceptable synonyms (Table 2).

In addition to occurring within a single codon, CG and TA doublets are generated by juxtaposition of codons ending in C or T and codons beginning with G or A. Since none of the maize preferred codons end in T, T/A juxtapositions are necessarily due to doublets internal to single codons, in gene versions using only preferred codons. CG doublets generated by amino acid pairs are located by reviewing the protein sequence for juxtapositions of amino acids that are represented by maize preferred codons ending in C, with amino acids represented by maize preferred codons starting with G. The "C-enders" are Gly (GGC), Asp (GAC), Ala (GCC), Arg (CGC, Ser (AGC), Asn (AAC), Ile (ATC), Thr (ACC), Cys (TGC), Tyr (TAC), Phe (TTC), His (CAC, and Pro (CCC); the "G-starters" are Gly (GGC), Glu (GAG), Asp (GAC), Val (GTG), and Ala (GCC) (Table 5).

TABLE 5

Amino Acid Juxtapositions That Generate CG Doublets
AMINO ACIDS WITH CODONS THAT START WITH G

| Amino Acids with Codons That End with C[a] | Glycine (G) | Glutamic Acid (E) | Aspartic Acid (D) | Valine (V) | Alanine (A) |
|---|---|---|---|---|---|
| Glycine (G) | Gly/Gly | Gly/Gly | Gly/Asp | Gly/Val | Gly/Ala |
| GGC(50) > GGT(21) | G/G | G/E | G/D | G/V | G/A |
| Alanine (A) | Ala/Gly | Ala/Glu | Ala/Asp | Ala/Val | Ala/Ala |
| GCC(36) > GCT(27) | A/G | A/E | A/D | A/V | A/A |
| Arginine (R) | Arg/Gly | Arg/Glu | Arg/Asp | Arg/Val | Arg/Ala |
| CGC(40) > AGG(26) | R/G | R/E | R/D | R/V | R/A |
| Serine (S) | | | | | |
| AGC(28) > TCG(16) | Ser/Gly | Ser/Glu | Ser/Asp | Ser/Val | Ser/Ala |
| AGC(28) > TCT(14) | S/G | S/E | S/D | S/V | S/A |
| Isoleucine (I) | Ile/Gly | Ile/Glu | Ile/Asp | Ile/Val | Ile/Ala |
| ATC(68) > ATT(24) | I/G | I/E | I/D | I/V | I/A |
| Threonine (T) | Thr/Gly | Thr/Glu | Thr/Asp | Thr/Val | Thr/Ala |
| ACC(47) > ACG(26) | T/G | T/E | T/D | T/V | T/A |
| Proline (P) | Pro/Gly | Pro/Glu | Pro/Asp | Pro/Val | Pro/Ala |
| CCC(30) > CCG(27) | P/G | P/E | P/D | P/V | P/A |

[a]Recommended codon substitutions and the relative frequencies of the codons in maize genes are given below the amino acid names.

Having identified such amino acid doublets, one could then try to change either of the codons to minimize the occurrence of CG doublets, without sacrificing an inordinate amount of codon bias. However, since all of the alternate codons for the preferred codon "G-starters" also begin with G, the G of these CG doublets can not be changed, and one is confined to changes in the codons for the first amino acid of the pair, when appropriate alternate codons exist. In some instances [e.g. Asp: GAC (76)>GAT (24); Asn: AAC (81) >AAT (19); Cys: TGC (79)> TGT (21); Tyr: TAC (86)>TAT (14); Phe: TTC (80)>TTT (20); and His: CAC (71)>CAT (29)], the alternate codon is found in maize genes at such a significantly lower frequency than the preferred codons that substitution is not an option. Therefore, doublets generated by those juxtapositions can be ignored.

Accordingly, a list of 128 doublets that comprised juxtapositions of the above amino acids that generate CG in the Mze HD73 #3 trnc protein sequence was compiled (Table 6). Changes to the sequence of the codons corresponding to 74 of the amino acid doublets (underlined position numbers in Table 6) were made to eliminate the CG base doublets.

TABLE 6

Amino Acid Juxtapositions in Mze HD73 #3 trnc That Generate CG Doublets[a]

| Position | Amino Acids |
|---|---|
| 8/9 | ASN/GLU |
| 19/20 | PRO/GLUE |
| 25/26 | GLY/GLY |
| 26/27 | GLY/GLU |
| 29/30 | ILE/GLU |
| 31/32 | THR/GLY |
| 36/37 | ILE/ASP |
| 48/49 | SER/GLU |
| 50/51 | PHE/VAL |
| 52/53 | PRO/GLY |
| 53/54 | GLY/ALA |
| 54/55 | ALA/GLY |
| 56/57 | PHE/VAL |
| 68/69 | PHE/GLY |
| 74/75 | ASP/ALA |
| 80/81 | ILE/GLU |
| 88/89 | ILE/GLU |

TABLE 6-continued

Amino Acid Juxtapositions in Mze HD73 #3 trnc That Generate CG Doublets[a]

| Position | Amino Acids |
|---|---|
| 91/92 | PHE/ALA |
| 110/111 | TYR/ALA |
| 111/112 | ALA/GLU |
| 115/116 | ARG/GLU |
| 119/120 | ALA/ASP |
| 124/125 | PRO/ALA |
| 127/128 | ARG/GLU |
| 135/136 | ASN/ASP |
| 139/140 | SER/ALA |
| 143/144 | THR/ALA |
| 148/149 | PHE/ALA |
| 149/150 | ALA/VAL |
| 159/160 | SER/VAL |
| 161/162 | TYR/VAL |
| 164/165 | ALA/ALA |
| 170/171 | SER/VAL |
| 173/174 | ARG/ASP |
| 174/175 | ASP/VAL |
| 176/177 | SER/VAL |
| 178/179 | PHE/GLY |
| 184/185 | PHE/ASP |
| 185/186 | ASP/ALA |
| 186/187 | ALA/ALA |
| 194/195 | ASN/ASP |
| 200/201 | ILE/GLY |
| 204/205 | THR/ASP |
| 206/207 | TYR/ALA |
| 207/208 | ALA/VAL |
| 213/214 | THR/GLY |
| 217/218 | ARG/VAL |
| 221/222 | PRO/ASP |
| 224/225 | ARG/ASP |
| 234/235 | ARG/GLU |
| 239/240 | THR/VAL |
| 243/244 | ILE/VAL |
| 250/251 | TYR/ASP |
| 259/260 | THR/VAL |
| 265/266 | ARG/GLU |
| 271/272 | PRO/VAL |
| 276/277 | PHE/ASP |
| 277/278 | ASP/GLY |
| 281/282 | ARG/GLY |
| 283/284 | SER/ALA |
| 287/288 | ILE/GLU |
| 307/308 | THR/ASP |
| 308/309 | ASP/ALA |
| 311/312 | ARG/GLY |
| 317/318 | SER/GLY |
| 325/326 | PRO/VAL |
| 329/330 | SER/GLY |
| 331/332 | PRO/GLU |
| 338/339 | TYR/GLY |
| 343/344 | ASN/ALA |
| 344/345 | ALA/ALA |
| 350/351 | ILE/VAL |
| 357/358 | GLY/VAL |
| 373/374 | ILE/GLY |
| 381/382 | SER/VAL |
| 384/385 | ASP/GLY |
| 386/387 | THR/GLU |
| 388/389 | PHE/ALA |
| 390/391 | TYR/GLY |
| 398/399 | SER/ALA |
| 399/400 | ALA/VAL |
| 404/405 | SER/GLY |
| 406/407 | THR/VAL |
| 412/413 | ASP/GLU |
| 419/420 | ASN/VAL |
| 432/433 | HIS/GLY |
| 438/439 | SER/GLY |
| 444/445 | SER/VAL |
| 449/450 | ARG/ALA |
| 459/460 | SER/ALA |
| 460/461 | ALA/GLU |
| 466/467 | ILE/ALA |
| 468/469 | SER/ASP |
| 475/476 | PRO/ALA |
| 476/477 | ALA/VAL |
| 484/485 | ASN/GLY |
| 486/487 | SER/VAL |
| 489/490 | SER/GLY |
| 491/492 | PRO/GLY |
| 494/495 | THR/GLY |
| 495/496 | GLY/GLY |
| 496/497 | GLY/ASP |
| 504/505 | SER/GLY |
| 511/512 | ARG/GLY |
| 514/515 | ILE/GLU |
| 528/529 | ARG/VAL |
| 530/531 | ARG/VAL |
| 533/534 | TYR/ALA |
| 535/536 | SER/VAL |
| 542/543 | ASN/VAL |
| 554/555 | THR/VAL |
| 556/557 | PRO/ALA |
| 558/559 | THR/ALA |
| 568/569 | SER/ASP |
| 570/571 | PHE/GLY |
| 573/574 | PHE/GLU |
| 575/576 | SER/ALA |
| 577/578 | ASN/ALA |
| 586/587 | ILE/VAL |
| 588/589 | GLY/VAL |
| 593/594 | SER/GLY |
| 595/596 | THR/ALA |
| 596/597 | ALA/GLY |
| 597/598 | GLY/VAL |
| 600/601 | ILE/ASP |
| 603/604 | PHE/GLU |
| 607/608 | PRO/VAL |
| 609/610 | THR/ALA |

[a]Bases in positions in bold type were changed as documented in Table 7 below.

The choice of which alternate codons to substitute for the preferred ones is largely determined by the fact that the alternate should not be amongst the class of very infrequently used codons. One factor to consider is that a DNA sequence comprised of only the preferred maize codons may suffer from expression problems, since an unnatural reliance on a single codon for each amino acid may deplete the pool of tRNAs or aminoacyl-tRNA synthetases for that codon. It is thought to be beneficial to introduce some diversity in codon composition by using second (or third) choice codons, as long as the natural usage of the codon in maize genes seems to accommodate the choice. In this regard, it is important to note that the frequency of codon occurrence in any organism's genes must be weighted relative to the number of synonymous codons that exist for the particular amino acid in the universal genetic code. For example, the relative frequencies of maize usage of the Phe codon TTT (20%) clearly reflects a greater amount of counterselection (codon bias) than the identical relative frequency of the Pro codon CCT (20%), since there are only two Phe codons, and four Pro codons (Table 2). The acceptability of an alternate codon as a substitute for a preferred one is therefore not a straightforward choice.

Additional factors come into play when making the choice of acceptable alternative codons to reduce the numbers of CG doublets. For example, when the preferred Arg codon CGC (40%) occurs in the context CGCG, two CG doublets are eliminated simultaneously by substitution with the second choice Arg codon AGG (26%). Clearly, such substitutions are desirable from the dual standpoints of reducing CG doublets, as well as generating codon diversity. On a more subtle basis, substitution of the preferred Thr codon ACC (47%) in the context ACCG by the second choice codon ACG (26%), or substitution of the preferred Ser codon AGC (28%) in the context AGCG by the third choice codon TCG (16%), does not change the overall numbers of CG doublets, but generates desirable codon diversity. Finally, substitution of the preferred Ser codon AGC (28%) in the context AGCG with the fourth choice codon TCT (14%) eliminates the CG doublet, generates codon diversity, and increases the overall number of CT doublets as well.

Table 7 summarizes these and other changes made to the sequence of Mze HD73 #3 trnc to generate Mze HD73 #4 trnc.

TABLE 7

Changes made in Mze HD73 #3 trnc → Mze HD73 #4 trnc

| Position | Change | Basis* |
|---|---|---|
| 75 | C > T | 1 |
| 78 | C > T | 1 |
| 156 | C > A | 1 |
| 159 | C > T | 1, 10 |
| 162 | C > T | 1, 9 |
| 183 | G > C | 2 |
| 264 | C > T | 1 |
| 333 | C > T | 1, 9 |
| 343 | C > A | 3 |
| 345 | C > G | 1 |
| 357 | C > T | 1, 9 |
| 372 | C > A | 1 |
| 379 | C > A | 1 |
| 381 | C > G | 1 |
| 429 | C > G | 3 |
| 447 | C > T | 1, 9 |
| 480 | G > C | 3, 9 |
| 492 | C > T | 1, 9 |
| 508 | A > T | 3 |
| 509 | G > C | 3 |
| 510 | C > G | 1 |
| 517 | C > A | 1 |
| 519 | C > G | 1 |
| 555 | C > T | 1 |
| 558 | C > T | 1, 9 |
| 600 | C > T | 1 |
| 612 | C > G | 3 |
| 639 | C > G | 3 |
| 649 | C > A | 1 |
| 651 | C > G | 1 |
| 663 | C > A | 1 |
| 670 | C > A | 1 |
| 672 | C > G | 1 |
| 700 | C > A | 3 |
| 702 | C > G | 1 |
| 717 | C > G | 1 |
| 729 | C > T | 1 |
| 777 | C > G | 1 |
| 793 | C > A | 1 |
| 795 | C > G | 1 |
| 813 | C > A | 1 |
| 847 | A > T | 3 |
| 848 | G > C | 3 |
| 849 | C > G | 1 |
| 852 | C > T | 3, 4, 9 |
| 861 | C > T | 1 |
| 921 | C > G | 1 |
| 927 | C > T | 3, 4, 9 |
| 949 | A > T | 3, 9 |
| 950 | G > C | 3, 9 |
| 951 | C > T | 1, 9 |
| 975 | C > A | 1 |
| 985 | A > T | 3, 9 |

TABLE 7-continued

Changes made in Mze HD73 #3 trnc → Mze HD73 #4 trnc

| Position | Change | Basis* |
|---|---|---|
| 986 | G > C | 3, 9 |
| 987 | C > T | 1, 9 |
| 993 | C > A | 1 |
| 1032 | C > T | 1, 9 |
| 1050 | C > T | 1 |
| 1071 | C > T | 1 |
| 1119 | C > T | 1 |
| 1141 | A > T | 3 |
| 1142 | G > C | 3 |
| 1143 | C > G | 1 |
| 1152 | C > T | 1 |
| 1158 | C > T | 1, 9 |
| 1167 | C > T | 3, 4, 9 |
| 1210 | A > T | 3, 9 |
| 1211 | G > C | 3, 9 |
| 1212 | C > T | 1, 9 |
| 1215 | C > T | 5 |
| 1221 | C > G | 6 |
| 1312 | A > T | 3 |
| 1313 | G > C | 3 |
| 1314 | C > G | 1 |
| 1330 | A > T | 3, 4 |
| 1331 | G > C | 3, 4 |
| 1332 | C > T | 1 |
| 1345 | C > A | 1 |
| 1347 | C > G | 1 |
| 1353 | C > A | 3, 4 |
| 1375 | A > T | 3, 9 |
| 1376 | G > C | 3, 9 |
| 1377 | C > T | 1, 9 |
| 1380 | C > T | 1, 9 |
| 1398 | C > T | 1 |
| 1402 | A > T | 3, 9 |
| 1403 | G > C | 3, 9 |
| 1404 | C > T | 1, 9 |
| 1428 | C > T | 1, 9 |
| 1456 | A > T | 3 |
| 1457 | G > C | 3 |
| 1458 | C > G | 1 |
| 1465 | A > T | 3 |
| 1466 | G > C | 3 |
| 1467 | C > G | 1 |
| 1470 | C > T | 3, 4 |
| 1473 | C > A | 1, 3, 4 |
| 1476 | C > T | 3, 4 |
| 1482 | C > G | 3 |
| 1485 | C > T | 1 |
| 1488 | C > T | 1 |
| 1510 | A > T | 3, 9 |
| 1511 | G > C | 3 |
| 1512 | C > G | 1 |
| 1515 | C > T | 3, 4 |
| 1582 | C > A | 1 |
| 1583 | C > G | 1 |
| 1587 | G > C | 3 |
| 1588 | C > A | 1 |
| 1590 | C > G | 1 |
| 1593 | G > C | 3 |
| 1594 | C > A | 1, 3, 4 |
| 1596 | C > G | 3, 4 |
| 1602 | C > T | 3, 4, 9 |
| 1603 | A > T | 3, 9 |
| 1604 | G > C | 3, 9 |
| 1605 | C > T | 1, 9 |
| 1662 | C > G | 1 |
| 1668 | C > A | 1 |
| 1674 | C > G | 1 |
| 1699 | A > T | 3 |
| 1700 | G > C | 3 |
| 1702 | A > T | 3, 9 |
| 1703 | G > C | 3 |
| 1704 | C > G | 1 |
| 1723 | A > T | 3 |
| 1724 | G > C | 3 |
| 1725 | C > G | 1 |

TABLE 7-continued

Changes made in Mze HD73 #3 trnc → Mze HD73 #4 trnc

| Position | Change | Basis* |
|---|---|---|
| 1764 | C > T | 1 |
| 1777 | A > T | 3, 9 |
| 1778 | G > C | 3, 9 |
| 1779 | C > T | 1 |
| 1785 | C > G | 1 |
| 1788 | C > T | 1, 9 |
| 1791 | C > T | 1 |
| 1821 | C > A | 1 |
| 1827 | C > G | 1 |
| 1831–33 | CCA | 7 |
| 1834–36 | CCA | 7 |
| 1837–39 | TAG | 8 |

*BASIS CODES: 1 = Eliminate CG doublet; 2 = Create Sal I site; 3 = Generate codon diversity; 4 = Reduce G + C content; 5 = Create Kpn I site; 6 = Eliminate Sal I site; 7 = Proline codon; 8 = Stop codon; 9 = Generate CT doublet; 10 = Eliminate Nar I site.

Two proline codons and a stop codon (TAG) were added to the end of the sequence (total amino acids now about 612), thereby producing MZE HD73 #4 trnc+. The presence of terminal proline residues is thought to reduce carboxy-terminus proteolysis. The resulting sequence was scanned for restriction sites. Base changes were made to eliminate a Sal I site at position 1219, create a new one at position 181, eliminate a Nar I site at position 158, and create a new Kpn I site at position 1217. An ORF search revealed the ICP ORF in frame 1, and one small ORF each in frames 2 and 3. The long frame 3 ORF present in previous versions of the gene was interrupted by a stop codon at base 78; no other ORFS beginning with an ATG and longer than 25 amino acids was present in frame 3.

Mze HD73 #5 trnc+: Reduction of GC content and increase in codon diversity. Comparison of base doublet frequencies between versions #4 trnc+ and previous versions of the sequence (Table 3) revealed that the base composition had been altered towards reductions in CG base pairs, and towards abundances in TG and CT base pairs. However, version #4 trnc+ still had a relatively high G+C content (62%) compared to the target of 55–60% for maize genes. Reduction of this parameter necessitated using more alternate codons containing A and/or T.

Table 8 summarizes the changes made to the sequence of Mze HD73 #4 trnc+ to generate Mze HD73 #5 trnc+.

TABLE 8

Changes made in Mze HD73 #4 trnc+ → Mze HD73 #5 trnc+

| Position | Change | Basis* |
|---|---|---|
| 15 | C > A | 1 |
| 36 | C > T | 1 |
| 46 | C > T | 1 |
| 57 | C > T | 1 |
| 72 | G > T | 1 |
| 87 | C > T | 1 |
| 105 | C > A | 1 |
| 115 | A > T | 1, 2 |
| 116 | G > C | 1, 2 |
| 117 | C > T | 1, 2 |
| 132 | G > A | 1 |
| 142 | A > T | 1, 2 |
| 143 | G > C | 1, 2 |
| 144 | C > T | 1, 2 |
| 174 | G > T | 1 |
| 177 | C > T | 1 |
| 210 | C > A | 1 |

TABLE 8-continued

Changes made in Mze HD73 #4 trnc+ → Mze HD73 #5 trnc+

| Position | Change | Basis* |
|---|---|---|
| 216 | G > A | 1 |
| 225 | C > T | 1 |
| 231 | G > T | 1 |
| 237 | G > A | 1 |
| 258 | G > A | 1 |
| 276 | C > T | 1 |
| 285 | G > A | 1 |
| 292 | A > T | 2 |
| 293 | G > C | 2 |
| 300 | G > T | 1 |
| 307 | C > T | 1 |
| 363 | C > A | 1 |
| 376 | C > T | 1 |
| 399 | G > A | 1 |
| 415 | A > T | 1, 2 |
| 416 | G > C | 1, 2 |
| 417 | C > T | 1, 2 |
| 420 | C > T | 1 |
| 438 | C > T | 1 |
| 462 | G > A | 1 |
| 468 | C > T | 1 |
| 471 | G > T | 1 |
| 489 | G > A | 1 |
| 499 | C > T | 1 |
| 510 | G > T | 1 |
| 514 | C > T | 1 |
| 526 | A > T | 1, 2 |
| 527 | G > C | 1, 2 |
| 528 | C > T | 1, 2 |
| 537 | C > T | 1 |
| 540 | G > A | 1 |
| 571 | A > T | 1, 2 |
| 572 | G > C | 1, 2 |
| 573 | C > T | 1, 2 |
| 621 | C > T | 1 |
| 660 | C > T | 1 |
| 667 | A > T | 2 |
| 668 | G > C | 2 |
| 684 | C > T | 1 |
| 693 | G > A | 1 |
| 723 | G > T | 1 |
| 735 | C > T | 1 |
| 744 | C > A | 1 |
| 754 | A > T | 2 |
| 755 | G > C | 2 |
| 759 | C > T | 1 |
| 768 | C > A | 1 |
| 781 | A > T | 1, 2 |
| 782 | G > C | 1, 2 |
| 783 | C > T | 1, 2 |
| 792 | C > T | 1 |
| 816 | G > T | 1 |
| 817 | C > T | 1 |
| 831 | C > T | 1 |
| 835 | A > T | 2 |
| 836 | G > C | 2 |
| 849 | G > T | 1 |
| 855 | G > A | 1 |
| 873 | C > T | 1 |
| 877 | A > T | 1, 2 |
| 878 | G > C | 1, 2 |
| 879 | C > T | 1, 2 |
| 882 | C > T | 1 |
| 897 | C > T | 1 |
| 900 | G > T | 1 |
| 912 | C > T | 1 |
| 960 | G > A | 1 |
| 969 | C > T | 1 |
| 978 | G > T | 1 |
| 981 | C > T | 1 |
| 1008 | C > T | 1 |
| 1009 | C > T | 1 |
| 1017 | C > T | 1 |
| 1035 | C > T | 1 |
| 1038 | C > A | 1 |

TABLE 8-continued

Changes made in Mze HD73 #4 trnc+ → Mze HD73 #5 trnc+

| Position | Change | Basis* |
|---|---|---|
| 1041 | G > A | 1 |
| 1056 | C > T | 1 |
| 1059 | G > A | 1 |
| 1068 | G > A | 1 |
| 1086 | G > T | 1 |
| 1087 | A > T | 2 |
| 1088 | G > C | 2 |
| 1096 | C > T | 1 |
| 1110 | C > A | 1 |
| 1135 | G > A | 1 |
| 1140 | G > T | 1 |
| 1143 | G > T |   |
| 1149 | G > T | 1 |
| 1177 | A > T | 1, 2 |
| 1178 | G > C | 1, 2 |
| 1179 | C > T | 1, 2 |
| 1186 | C > T | 1 |
| 1191 | C > A | 1 |
| 1197 | C > T | 1 |
| 1228 | C > T | 1 |
| 1242 | C > T | 1 |
| 1245 | C > A | 1 |
| 1263 | C > A | 1 |
| 1266 | C > T | 1 |
| 1272 | G > A | 1 |
| 1279 | A > T | 1, 2 |
| 1280 | G > C | 1, 2 |
| 1281 | C > T | 1, 2 |
| 1288 | C > T | 1 |
| 1299 | G > T | 1 |
| 1300 | A > T | 2 |
| 1301 | G > C | 2 |
| 1311 | C > T | 1 |
| 1341 | C > T | 1 |
| 1360 | A > T | 2 |
| 1361 | G > C | 2 |
| 1374 | C > T | 1 |
| 1416 | C > T | 1 |
| 1419 | G > A | 1 |
| 1425 | C > T | 1 |
| 1431 | G > T | 1 |
| 1446 | G > T | 1 |
| 1494 | G > T | 1 |
| 1501 | C > T | 1 |
| 1536 | C > T | 1 |
| 1551 | C > A | 1 |
| 1563 | C > A | 1 |
| 1564 | A > T | 2 |
| 1565 | G > C | 2 |
| 1614 | C > A | 1 |
| 1621 | C > T | 1 |
| 1645 | A > T | 2 |
| 1646 | G > C | 2 |
| 1686 | G > T | 1 |
| 1722 | G > A | 1 |
| 1734 | C > T | 1 |
| 1744 | A > T | 1, 2 |
| 1745 | G > C | 1, 2 |
| 1746 | C > T | 1, 2 |
| 1749 | G > T | 1 |
| 1812 | G > A | 1, 3 |
| 1830 | C > T | 1 |

*BASIS CODES: 1 = Reduce G + C content; 2 = Generate codon diversity; 3 = Create EcoR I site.

As shown by the Basis Codes for the table, these changes were made to reduce the G+C content of the DNA and to introduce additional codon diversity, without sacrificing an inordinant amount of codon bias. Where possible, blocks of high G+C sequence were interrupted by the addition of T or A substitutions. Also, a unique EcoR I site was created near the 3' end of the gene to provide for possible future sequence additions. Substitute codons choices useful to reduce GC content are set forth in Table 9.

TABLE 9

Alternative codons used to reduce G + C content or increase CT or TG doublets

| Amino Acid | Substitute Codon Choices[a] | | | |
|---|---|---|---|---|
| | Preferred | 1st Alternate | 2nd Alternate | 3rd Alternate |
| Ala | GCC(36) | GCT(27) | GCG(24) | |
| Arg | CGC(40) | AGG(26) | CGG(13) | CGT(11) |
| Asp | GAC(76) | GAT(24) | | |
| Gln | CAG(59) | CAA(41) | | |
| Glu | GAG(81) | GAA(19) | | |
| Gly | GGC(50) | GGT(21) | GGG(16) | |
| Ile | ATC(68) | ATT(24) | | |
| Leu | CTG(31) | CTC(28) | CTT(13) | TTG(13) |
| Pro | CCC(30) | CCG(27) | CCA(23) | CCT(20) |
| Ser | AGC(28) | TCC(27) | TCG(16) | TCT(14) |
| Thr | ACC(47) | ACG(26) | ACT(16) | |
| Val | GTG(40) | GTRC(37) | GTT(17) | |

[a]Numbers in parentheses are frequencies of usage in maize genes (from Table 2).

Substitutions (listed in Table 9) were made with the following rationales listed below:

i) While all Pro codons are acceptable substitutes for one another, CCT generates a CT doublet, as well as lowers the G+C content.

ii) The two Gln codons are present in maize genes in approximately equal frequencies, and can therefore be readily substituted for one another. Similarly, the Ser codons AGC and TCC are considered to be interchangeable. Analogous frequency similarities exist for the Val codons GTG and GTC, Leu codons CTG and CTC, and Ala minor codons GCT and GCG.

iii) Leu and Ser minor codons TTG and TCT are acceptable when they follow a C-ending codon, so that additional CT doublets are generated. TTG offers the added feature of increasing the TG doublet count.

iv) Arg codon AGG may be substituted for the preferred codon CGC (see discussion in previous section). Although AGG occurs in maize genes at substantially lower frequency than the preferred codon, it is found twice as often as the third choice codon.

v) Minor codons such as GAT (Asp), GAA (Glu), ATT (Ile), ACT (Thr), and GTT (Val), which have obviously been counterselected in maize, should be used sparingly, if possible. It is preferable that they be placed before or after codons that will contribute to the formation of a CT or TG doublet. Because they are a feature of native maize genes, their inclusion in a synthetic gene need not be avoided entirely.

Mze HD73 #6 trnc+. Only a few changes were made to the sequence of Mze HD73 #5 trnc+ to generate the final version of the gene, Mze HD73 #6 trnc+. (summarized in Table 10).

TABLE 10

Mze HD73 #5 trnc+ → Mze HD73 #6 trnc+

| Position | Change | Rationale |
|---|---|---|
| 1831–33 | CCA → ACC | Pro → Thr |
| 1834–36 | CCA → CTG | Pro → Leu |
| 1837–39 | TAG → GAG | Stop → Glu |
| 1840–42 | GCT | Ala codon |
| 1843–45 | GAG | Glu codon |
| 1846–48 | CCA | Pro codon |

TABLE 10-continued

Mze HD73 #5 trnc+ → Mze HD73 #6 trnc+

| Position | Change | Rationale |
|---|---|---|
| 1849–51 | CCA | Pro codon |
| 1852–54 | TAG | Stop codon |

As summarized in Table 11, changes resulting in Mze HD73 #5 trnc+ and Mze HD73 #6 trnc+ diminished the numbers of CG doublets by almost 50%, and clearly enriched in TG and CT doublets. Moreover, the G+C content of 56% falls well within the range of maize metabolic genes.

TABLE 11

Comparisons of base doublet numbers and base compositions of ICP genes

| | | | Truncated HD73 Gene Versions | | | | |
|---|---|---|---|---|---|---|---|
| Doublet | BT 1830 bp | Mze #1 1830 bp | Mze #2 1830 bp | Mze #3 1830 bp | Mze #4 1836 bp[a] | Mze #5 1836 bp[a] | Mze #6 1851 bp[a] |
| TA | 174 | 27 | 27 | 27 | 29[a] | 36[a] | 37[a] |
| CG | 46 | 171 | 170 | 168 | 102 | 90 | 90 |
| TG | 102 | 110 | 107 | 105 | 138 | 142 | 144 |
| CT | 86 | 98 | 98 | 98 | 129 | 165 | 167 |
| % G + C | 37 | 66 | 66 | 66 | 62 | 56 | 56 |

[a]TAG stop codon, not considered to be part of the coding region, is ignored.

Examination of the DNA sequence that Perlak et al. (*PNAS*, 88 (1991) 3324) successfully expressed in transgenic plants revealed that the gene encoded 615 amino acids of the native ICP (rather than the 610 encoded by MZE HD73 #5 trnc+). Codons for the five (5) additional amino acids were therefore added between codon 610 and the two (2) Pro codons added in version #4. MZE HD73 #6 trnc+therefore encodes 615 amino acids of native HD73 ICP, and two carboxy-terminus proline residues (SEQ. ID. NO. 1).

Table 12 below lists the codon usage patterns of the native Bacillus HD73 gene, the Mze HD73 #1 trnc+gene, and Mze HD73 #6 trnc+.

TABLE 12

Comparisons of codon numbers of ICP genes

| Amino Acid | Codon[a] | Bt | Mze #1 | Mze #6 |
|---|---|---|---|---|
| Gly | GGG(16) | 8 | 0 | 0 |
| Gly | GGA(13) | 19 | 0 | 0 |
| Gly | GGT(21) | 13 | 0 | 18 |
| Gly | GGC(50) | 5 | 45 | 27 |
| Glu | GAG(81) | 2 | 27 | 27 |
| Glu | GAA(19) | 25 | 0 | 2 |
| Asp | GAT(24) | 20 | 0 | 3 |
| Asp | GAC(76) | 5 | 25 | 22 |
| Val | GTG(40) | 6 | 42 | 32 |
| Val | GTA(6) | 18 | 0 | 0 |
| Val | GTT(17) | 18 | 0 | 4 |
| Val | GTC(37) | 0 | 0 | 6 |
| Ala | GCG(24) | 1 | 0 | 0 |
| Ala | GCA(13) | 11 | 0 | 0 |
| Ala | GCT(27) | 19 | 0 | 26 |
| Ala | GCC(36) | 4 | 35 | 10 |
| Arg | AGG(26) | 7 | 0 | 15 |
| Arg | AGA(7) | 23 | 0 | 0 |
| Arg | CGG(13) | 1 | 0 | 0 |
| Arg | CGA(3) | 4 | 0 | 0 |
| Arg | CGT(11) | 7 | 0 | 4 |

TABLE 12-continued

Comparisons of codon numbers of ICP genes

| Amino Acid | Codon[a] | Bt | Mze #1 | Mze #6 |
|---|---|---|---|---|
| Arg | CGC(40) | 1 | 43 | 24 |
| Ser | AGT(5) | 21 | 0 | 0 |
| Ser | AGC(28) | 3 | 61 | 23 |
| Ser | TCG(16) | 7 | 0 | 6 |
| Ser | TCA(10) | 12 | 0 | 0 |
| Ser | TCT(14) | 11 | 0 | 21 |
| Ser | TCC(27) | 7 | 0 | 11 |

TABLE 12-continued

Comparisons of codon numbers of ICP genes

| Amino Acid | Codon[a] | Bt | Mze #1 | Mze #6 |
|---|---|---|---|---|
| Lys | AAG(90) | 1 | 2 | 2 |
| Lys | AAA(10) | 1 | 0 | 0 |
| Asn | AAT(19) | 34 | 0 | 0 |
| Asn | AAC(81) | 14 | 48 | 48 |
| Ile | ATA(8) | 18 | 0 | 0 |
| Ile | ATT(24) | 23 | 0 | 13 |
| Ile | ATC(68) | 6 | 47 | 34 |
| Thr | ACG(26) | 5 | 0 | 12 |
| Thr | ACA(11) | 12 | 0 | 0 |
| Thr | ACT(16) | 12 | 0 | 4 |
| Thr | ACC(47) | 6 | 35 | 20 |
| Trp | TGG(100) | 10 | 10 | 10 |
| End | TGA(26) | 0 | 0 | 0 |
| End | TAG(52) | 0 | 0 | 1 |
| End | TAA(22) | 0 | 0 | 0 |
| Cys | TGT(21) | 1 | 0 | 0 |
| Cys | TGC(79) | 1 | 2 | 2 |
| Tyr | TAT(14) | 23 | 0 | 0 |
| Tyr | TAC(86) | 4 | 27 | 27 |
| Leu | TTG(13) | 5 | 0 | 13 |
| Leu | TTA(3) | 22 | 0 | 0 |
| Leu | CTG(31) | 2 | 48 | 20 |
| Leu | CTA(9) | 8 | 0 | 0 |
| Leu | CTT(16) | 10 | 0 | 14 |
| Leu | CTC(28) | 1 | 0 | 2 |
| Phe | TTT(20) | 30 | 0 | 0 |
| Phe | TTC(80) | 6 | 36 | 36 |
| Gln | CAG(59) | 5 | 27 | 8 |
| Gln | CAA(41) | 22 | 0 | 19 |

TABLE 12-continued

Comparisons of codon numbers of ICP genes

| Amino Acid | Codon[a] | Bt | Mze #1 | Mze #6 |
|---|---|---|---|---|
| His | CAT(29) | 7 | 0 | 0 |
| His | CAC(71) | 2 | 9 | 9 |
| Pro | CCG(27) | 6 | 0 | 0 |
| Pro | CCA(23) | 15 | 0 | 26 |
| Pro | CCT(20) | 10 | 0 | 9 |
| Pro | CCC(30) | 2 | 33 | 0 |
| Met | ATG(100) | 8 | 8 | 8 |

[a]Numbers in parentheses refer to codon usage (%) in maize genes, as explained for Table 2.

Analysis of Mze HD73 #6 trnc+ and comparison to dicots and maize genes is set forth in Table 13.

TABLE 13

Deviation of codon usage between MZE HD73 #6 trnc+, dicots and maize.

| Amino Acid | Codon | Freq. of Codon Usage in Mze #6[a] ($Y_n$) | Freq. of Codon Usage in Dicots[b] ($X_n$) | Dev. of Codon Usage from Dicots[c] A | Freq. of Codon Usage in Maize[b] ($X_n$) | Deviation of Codon Usage from Maize[c] A |
|---|---|---|---|---|---|---|
| Gly | GGG | 0 | 0.12 | 1.5625 | 0.16 | 1.5625 |
|  | GGA | 0 | 0.38 | 1.5625 | 0.13 | 1.5625 |
|  | GGT | 0.4 | 0.33 | 0.3314394 | 0.21 | 1.4136905 |
|  | GGC | 0.6 | 0.16 | 4.296875 | 0.5 | 0.3125 |
| Glu | GAG | 0.93104 | 0.51 | 1.2899341 | 0.81 | 0.233477 |
|  | GAA | 0.06896 | 0.49 | 1.3425844 | 0.19 | 0.9953494 |
| Asp | GAT | 0.12 | 0.58 | 1.2392241 | 0.24 | 0.78125 |
|  | GAC | 0.88 | 0.42 | 1.7113095 | 0.76 | 0.2467105 |
| Val | GTG | 0.76191 | 0.29 | 2.5425903 | 0.4 | 1.4136905 |
|  | GTA | 0 | 0.12 | 1.5625 | 0.06 | 1.5625 |
|  | GTT | 0.09524 | 0.39 | 1.1809371 | 0.17 | 0.6871499 |
|  | GTC | 0.14286 | 0.2 | 0.4464286 | 0.37 | 0.9592181 |
| Ala | GCG | 0 | 0.06 | 1.5625 | 0.24 | 1.5625 |
|  | GCA | 0 | 0.25 | 1.5625 | 0.13 | 1.5625 |
|  | GCT | 0.72222 | 0.42 | 1.1243386 | 0.27 | 2.6170267 |
|  | GCC | 0.27778 | 0.27 | 0.0450103 | 0.36 | 0.3568673 |
| Arg | AGG | 0.34884 | 0.25 | 0.6177326 | 0.26 | 0.5338775 |
|  | AGA | 0 | 0.3 | 1.5625 | 0.07 | 1.5625 |
|  | CGG | 0 | 0.04 | 1.5625 | 0.13 | 1.5625 |
|  | CGA | 0 | 0.08 | 1.5625 | 0.03 | 1.5625 |
|  | CGT | 0.09302 | 0.21 | 0.8703627 | 0.11 | 0.2411469 |
|  | CGC | 0.55814 | 0.11 | 6.3656184 | 0.4 | 0.6177326 |
| Ser | AGT | 0 | 0.14 | 1.5625 | 0.05 | 1.5625 |
|  | AGC | 0.37705 | 0.18 | 1.7104964 | 0.28 | 0.5415691 |
|  | TCG | 0.09836 | 0.06 | 0.9989754 | 0.16 | 0.6019467 |
|  | TCA | 0 | 0.19 | 1.5625 | 0.1 | 1.5625 |
|  | TCT | 0.34426 | 0.25 | 0.5891393 | 0.14 | 2.2797131 |
|  | TCC | 0.18033 | 0.18 | 0.0028461 | 0.27 | 0.5189359 |
| Lys | AAG | 1 | 0.61 | 0.9989754 | 0.9 | 0.1736111 |
|  | AAA | 0 | 0.39 | 1.5625 | 0.1 | 1.5625 |
| Asn | AAT | 0 | 0.45 | 1.5625 | 0.19 | 1.5625 |
|  | AAC | 1 | 0.55 | 1.2784091 | 0.81 | 0.3665123 |
| Ile | ATA | 0 | 0.18 | 1.5625 | 0.08 | 1.5625 |
|  | ATT | 0.27659 | 0.45 | 0.6020981 | 0.24 | 0.2382535 |
|  | ATC | 0.72340 | 0.37 | 1.4924166 | 0.68 | 0.099734 |
| Thr | ACG | 0.33333 | 0.08 | 4.9479167 | 0.26 | 0.4407051 |
|  | ACA | 0 | 0.27 | 1.5625 | 0.11 | 1.5625 |
|  | ACT | 0.11111 | 0.35 | 1.0664683 | 0.16 | 0.4774306 |
|  | ACC | 0.55556 | 0.3 | 1.3310185 | 0.47 | 0.2844267 |
| Trp | TAG | 1 | 1 | 0 | 1 | 0 |
| End | TGA | 0 | 0.33 | 1.5625 | 0.26 | 1.5625 |
|  | TAG | 1 | 0.19 | 6.6611842 | 0.52 | 1.4423077 |
|  | TAA | 0 | 0.48 | 1.5625 | 0.22 | 1.5625 |
| Cys | TGT | 0 | 0.44 | 1.5625 | 0.21 | 1.5625 |
|  | TGC | 1 | 0.56 | 1.2276786 | 0.79 | 0.4153481 |
| Tyr | TAT | 0 | 0.43 | 1.5625 | 0.14 | 1.5625 |
|  | TAC | 1 | 0.57 | 1.1787281 | 0.86 | 0.2543605 |
| Leu | TTG | 0.26531 | 0.26 | 0.0318878 | 0.13 | 1.6262755 |
|  | TTA | 0 | 0.1 | 1.5625 | 0.03 | 1.5625 |
|  | CTG | 0.40816 | 0.09 | 5.5236678 | 0.31 | 0.4947745 |

TABLE 13-continued

Deviation of codon usage between MZE HD73 #6 trnc+, dicots and maize.

| Amino Acid | Codon | Freq. of Codon Usage in Mze #6[a] ($Y_n$) | Freq. of Codon Usage in Dicots[b] ($X_n$) | Dev. of Codon Usage from Dicots[c] A | Freq. of Codon Usage in Maize[b] ($X_n$) | Deviation of Codon Usage from Maize[c] A |
|---|---|---|---|---|---|---|
| | CTA | 0 | 0.08 | 1.5625 | 0.09 | 1.5625 |
| | CTT | 0.28571 | 0.28 | 0.0318878 | 0.16 | 1.2276786 |
| | CTC | 0.04082 | 0.19 | 1.2268394 | 0.28 | 1.3347303 |
| Phe | TTT | 0 | 0.45 | 1.5625 | 0.2 | 1.5625 |
| | TTC | 1 | 0.55 | 1.2784091 | 0.8 | 0.390625 |
| Gln | CAG | 0.29630 | 0.41 | 0.433322 | 0.59 | 0.777817 |
| | CAA | 0.70370 | 0.59 | 0.3011221 | 0.41 | 1.1192977 |
| His | CAT | 0 | 0.54 | 1.5625 | 0.29 | 1.5625 |
| | CAC | 1 | 0.46 | 1.8342391 | 0.71 | 0.6382042 |
| Pro | CCG | 0 | 0.09 | 1.5625 | 0.27 | 1.5625 |
| | CCA | 0.74286 | 0.42 | 1.2011054 | 0.23 | 3.4840839 |
| | CCT | 0.25714 | 0.32 | 0.3069196 | 0.2 | 0.4464286 |
| | CCC | 0 | 0.17 | 1.5625 | 0.3 | 1.5625 |
| Met | ATG | 1 | 1 | 0 | 1 | 0 |
| | Total | | | 97.160136 | | 68.584457 |

[a]Calculations based on codon numbers for MZE HD73 #6 trnc+ from Table 12.
[b]Numbers taken from U.S.P.N. 5,380,831 (Table 1)
[c]Calculations based on formula set forth in Definitions section.

Compared to the bacterial sequence, Mze HD73 #6 trnc+ has 538 base changes within the 1845 bp of the ICP coding region (538/1845×100=29% difference), and 6 additional changes due to the addition of the two Pro codons, for a total of 544 differences in 1851 bp. Comparison with the DNA sequence published by Perlak et al. (*PNAS*, 88 (1991) 3324) reveals that the present maize optimized Bt ICP gene differs at 422 positions out of 1845 (23% difference), and the encoded proteins differ at amino acids 206, 227, 245, 254, 289, and 313 (6 changes out of 615 amino acids, not including the terminal prolines).

Table 14 set forth below further illustrates the teachings of the method of modifying a gene by using preferred and non-preferred maize codons to make a plant optimized nucleotide sequence.

TABLE 14

Use of Non-preferred Maize Codons in MZE HD73 #6 trnc+

| | PHE | | | | | |
|---|---|---|---|---|---|---|
| Maize (%) | TTC(76) | TTT(24) | | | | |
| MZE#6(36) | 36 | 0 | | | | |
| | LEU | | | | | |
| Maize (%) | CTG(28) | CTC(26) | CTT(16) | TTG(15) | CTA(10) | TTA(5) |
| MZE#6(49) | 20 | 2 | 14 | 13 | 0 | 0 |
| | SER | | | | | |
| Maize (%) | AGC(26) | TCC(24) | TCG(16) | TCT(14) | TCA(13) | AGT(7) |
| MZE#6(61) | 23 | 11 | 6 | 21 | 0 | 0 |
| | TYR | | | | | |
| Maize (%) | TAC(80) | TAT(20) | | | | |
| MZE#6(27) | 27 | 0 | | | | |
| | END | | | | | |
| Maize (%) | TGA(46) | TAG(42) | TAA(12) | | | |
| MZE#6(1) | 0 | 1 | 0 | | | |
| | CYS | | | | | |
| Maize (%) | TGC(75) | TGT(25) | | | | |
| MZE#6(2) | 2 | 0 | | | | |
| | TRP | | | | | |
| Maize (%) | TGG(100) | | | | | |
| MZE#6(10) | 10 | | | | | |
| | PRO | | | | | |
| Maize (%) | CCG(29) | CCA(26) | CCC(25) | CCT(20) | | |
| MZE#6(35) | 0 | 26 | 0 | 9 | | |
| | HIS | | | | | |
| Maize (%) | CAC(65) | CAT(35) | | | | |
| MZE#6(9) | 9 | 0 | | | | |
| | GLN | | | | | |
| Maize (%) | CAG(56) | CAA(44) | | | | |
| MZE#6(27) | 8 | 19 | | | | |
| | ARG | | | | | |

TABLE 14-continued

Use of Non-preferred Maize Codons in MZE HD73 #6 trnc+

| | | | | | | |
|---|---|---|---|---|---|---|
| Maize (%) | CGC(34) | AGG(30) | CGG(14) | CGT(10) | AGA(8) | CGA(4) |
| MZE#6(43) | 24 | 15 | 0 | 4 | 0 | 0 |
| | ILE | | | | | |
| Maize (%) | ATC(60) | ATT(27) | ATA(13) | | | |
| MZE#6(47) | 34 | 13 | 0 | | | |
| | MET | | | | | |
| Maize (%) | ATG(100) | | | | | |
| MZE#6(8) | 8 | | | | | |
| | THR | | | | | |
| Maize (%) | ACC(45) | ACG(22) | ACT(18) | ACA(15) | | |
| MZE#6(36) | 20 | 12 | 4 | 0 | | |
| | ASN | | | | | |
| Maize (%) | AAC(79) | AAT(21) | | | | |
| MZE#6(48) | 48 | 0 | | | | |
| | LYS | | | | | |
| Maize (%) | AAG(81) | AAA(19) | | | | |
| MZE#6(2) | 2 | 0 | | | | |
| | VAL | | | | | |
| Maize (%) | GTG(42) | GTC(33) | GTT(18) | GTA(7) | | |
| MZE#6(42) | 32 | 6 | 4 | 0 | | |
| | ALA | | | | | |
| Maize (%) | GCC(33) | GCG(26) | GCT(26) | GCA(15) | | |
| MZE#6(36) | 10 | 26 | 0 | 0 | | |
| | ASP | | | | | |
| Maize (%) | GAC(68) | GAT(32) | | | | |
| MZE#6(25) | 22 | 3 | | | | |
| | GLU | | | | | |
| Maize (%) | GAG(76) | GAA(24) | | | | |
| MZE#6(29) | 27 | 2 | | | | |
| | GLY | | | | | |
| Maize (%) | GGC(45) | GGG(21) | GGT(21) | GGA(13) | | |
| MZE#6(45) | 27 | 0 | 18 | 0 | | |

In MZE HD73 #6 trnc+, maize codon preferences are distributed as follows:

19 of the 20 first choice codons are used a total of 389 out of 618 possible times, or 63% of the time.

13 of the 18 second choice codons are used a total of 136 times out of 618 possible times, or 22% of the time.

5 of the 10 third choice codons are used a total of 46 times out of 618 possible times, or 7.5% of the time.

6 of the 8 fourth choice codons are used a total of 47 times out of 618 possible times, or 7.5% of the time.

0 of the 3 fifth choice codons are used.

0 of the 3 sixth choice codons are used. Based on the frequency of use of first choice maize codons, MZE HD73 #6 trnc+ is 63% homologous to a pure plant optimized nucleotide sequence.

Synthesis of a Maize Optimized Bt ICP Gene

A nucleotide sequence corresponding to Mze HD73 #6 trnc+ was synthesized in a series of Polymerase Chain Reactions (PCR) as taught in U.S. Pat. No. 4,683,202 to Mullis and U.S. Pat. No. 4,683,195 to Mullis et al., by stepwise addition of overlapping oligonucleotides. The procedure relies on PCR amplification of intermediate synthesis product, followed by amplification of extensively modified large DNA fragments prior to cloning. Following one round of amplification, the intermediate product is purified, annealed to the next set of overlapping primers, and amplified. Entire genes can thus be synthesized without annealing, ligation, transformation and selection of intermediate reaction products; steps that are necessary with other approaches.

Taq polymerase, the enzyme used in PCR amplification, lacks 3'-5' exonuclease activity, and therefore is unable to 'proofread' the nascent sequence and remove misincorporated nucleotides. Under certain conditions (55° C. annealing temperature and 200 $\mu$M deoxynucleotide concentration), the polymerase was calculated to misincorporate nucleotides at a frequency of $5\times10^{-6}$ (Gelfland et al., *PCR Protocols*, (1989), Academic Press, Inc., San Diego, Calif.). The chance that an error occurs in a certain sequence increases with increasing numbers of amplification cycles, and therefore larger genes are best synthesized in several separate parts of intermediate size (500–700 nucleotides) which are subsequently sown together by PCR amplification, or joined together by traditional ligation of ends. This strategy also allows the different parts to be modified or exchanged without affecting the entire sequence of the gene.

In one aspect of the invention for the design of the Bt ICP gene, several unique restriction enzyme recognition sites were introduced into the sequence to allow the joining of separately synthesized parts (SEQ. ID. NO. 1). Also, two C residues were added to the 5' end of the sequence shown in SEQ. ID. NO. 1 to generate an Nco I site, and a BamH I site was added to the 3' end of the gene (downstream of the coding region) so that the completed ICP gene could be inserted into Nco I and BamH I (or other sites with BamH I compatible ends) sites in some of the vectors. The 1854 nt ICP sequence was split into three parts of roughly equivalent size. Each part, upon completion of the synthesis, was designed to contain at each of its ends a unique restriction site. These sites were used to join the individual parts together to construct the contiguous sequence encoding 617 amino acids. The 5' part was designed to have unique 5' Nco I and 3' Xho I sites at the ends, the central part was designed to have unique 5' Xho I and 3' Kpn I sites at the ends, and the 3' part was designed to have unique 5' Kpn I and 3' BamH I sites (see FIG. 1A).

In another aspect of the invention, the 5'-most ICP gene fragment of 653 basepairs (bp) was synthesized from 12 overlapping 61 to 86 base long oligonucleotides in 6 PCR steps. All oligonucleotides were designed to produce 18 to 20 base overlaps during the successive PCR steps. In each case, synthesis of the fragment was carried out from the "inside-out", as is exemplified in FIG. 1B. Step 1 of the synthesis process was begun by annealing of oligonucleotides Bt1 and Bt2. Only in the central area of overlap between the two is the annealed molecule double stranded. The remainder of the molecule was made double stranded by extension with the Taq Polymerase during 30 amplification cycles. In the second step, this double stranded molecule was denatured, then annealed to and reamplified with oligonucleotides Bt3 and Bt4. In the third step, this double stranded molecule (corresponding to the sequence of Bt3, Bt1, Bt2 and Bt4) was denatured, annealed to and amplified with oligonucleotides Bt5 and Bt6. This process was repeated until the sequence was extended to a 653 bp double stranded molecule corresponding to the entire sequence of the 5' part of the Bt gene (see FIG. 1B). Similarly, the 584 bp central fragment was synthesized using 10 overlapping 75 to 83 base long oligonucleotides in 5 PCR steps and the 3'-most ICP gene fragment of 657 bp was synthesized using 12 overlapping 59 to 84 base oligonucleotides in 6 PCR steps. Following synthesis, each of the gene parts cloned in pBlueScript ("pBS", Stratagene, La Jolla, Calif.) vectors were verified by sequence analysis. Corrections, when necessary, were made using a PCR mutagenesis approach. The corrections were resequenced prior to joining of the individual fragments into the complete gene.

The Bt ICP gene was constructed from a total of 34 oligonucleotides ranging in size from 59 to 86 nt. The sequence of all 34 oligonucleotides is presented in Table 15.

TABLE 15

Oligonucleotides Used in the Synthesis of the Bt ICP gene[a]

| Name (SEQ.ID.NO) | Fragment | Sequence | Location | Size |
|---|---|---|---|---|
| Bt 1 (9) | 5' end | CGA GCA GCT CAT CAA CCA ACG CAT TGA GGA GTT CGC TCG CAA CCA AGC CAT CTC CAG GCT TGA GGG CTT GAG CAA CCT GTA | 240–330 | 81 |
| Bt 2 (10) | 5' end | CAA GGC TAG GTT GGT TAG GTC AGC CTC CCA CTC CCT GAA GCT CTC AGC GTA GAT TTG GTA CAG GTT GCT CAA GCC CTC | rc 301–378 | 78 |
| Bt 3 (11) | 5' end | CTT CGG CCC AAG CCA ATG GGA CGC TTT CCT TGT GCA AAT CGA GCA GCT CAT CAA CCA ACG CAT TGA GG | 201–268 | 68 |
| Bt 4 (12) | 5' end | GGC CGT GGT CAG AGC AGA GTT CAT GTC GTT GAA TTG GAT GCG CAT CTC CTC CCT CAA GGC TAG GTT GGT TAG G | rc 360–432 | 73 |
| Bt 5 (13) | 5' end | CTG AGT TCG TGC CAG GTG CTG GCT TCG TGC TTG GTC TAG TCG ACA TCA TCT GGG GCA TCT TCG GCC CAA GCC AAT GGG | 143–220 | 78 |
| Bt 6 (14) | 5' end | TGC ACG TAG ACG CTC AGA AGA GGC ACT TAG TAG TTC TGC ACA GCG AAC AGA GGG ATG GCC GTG GTC AGA GCA GAG TTC A | rc 410–488 | 79 |
| Bt 7 (15) | 5' end | ACA CCC CAA TCG ACA TCT CTC TGA GCC TGA CCC AAT TCC TGC TGT CTG AGT TCG TGC CAG GTG CTG GC | 98–165 | 71 |
| Bt 8 (16) | 5' end | CGA AGC CCC AGC GTT GAC CGA ACA CAG ACA CGT CCC TCA ACA CAG ACA GGT GCA AGT TAG CAG CTT GCA CGT AGA CGC TCA GAA GAG | rc 467–553 | 86 |
| Bt 9 (17) | 5' end | GAG GTG GAG GTG CTT GGT GGT CAG CGC ATT GAG ACC GGC TAC ACC CCA ATC GAC ATC TCT C | 58–118 | 61 |
| Bt 10 (18) | 5' end | CAG CCT GGT CAG GTC GTT GTA GCG AGA GTT GAT GGT GGC AGC ATC GAA GCC CCA GCG TTG ACC G | rc 534–597 | 64 |
| Bt 11 (19) | 5' end | CCA TAG ACA ACC CAA ACA TCA ACG AGT GCA TCC CTT ACA ACT GCT TGA GCA ACC CTG AGG TAG AGG TGC TTG GTG G | 2–77 | 79 |
| Bt 12 (20) | 5' end | CCT CTC GAG GCC CGT GTT GTA CCA GCG CAC AGC GTA GTC CGT GTA GTT GCC AAT CAG CCT GGT CAG GTC GTT GTA GCG | rc 574–651 | 78 |
| Bt 13 (21) | center | CGC TCT CCT CAC CTG ATG GAC ATT CTT AAC AGC ATC ACT ATC TAC ACG GAC GCT CAC CGC GGC TAC TAC TAC TAG | 874–948 | 75 |
| Bt 14 (22) | center | GAA CTC TAG GCC AGA GAA ACC AAC TAG GGA AGC CAT GAT TTG GTG GCC AGA CCA GTA GTA GTA GCC GCG GTG AGC | rc 799–925 | 75 |
| Bt 15 (23) | center | TTG GAG AAC TTC GAT GGC TCC TTC AGG GGC TCT GCT CAA GGC ATT GAG CGC AGC ATT CGC TCT CCT CAC CTG ATG GAC | 817–894 | 78 |
| Bt 16 (24) | center | GTT GAG CCA CAA TGC GCT GTT GTG GAG CAG CGT TGC CCA TCG TAC CGT ACA AAG GGA AGG TGA ACT CTG GGC CAG AGA AAC C | rc 979–1060 | 82 |
| Bt 17 (25) | center | CCC GTC GCT ACC CAA TCC GCA CGG TGT CTC AGC TGA CTA GGG AGA TTT ACA CCA ACC CAG TTT TAG AGA ACT TCG ATG GCT CC | 755–837 | 83 |

TABLE 15-continued Oligonucleotides Used in the Synthesis of the Bt ICP gene[a]

| Name (SEQ.ID.NO) | Fragment | Sequence | Location | Size |
|---|---|---|---|---|
| Bt 18 (26) | center | GTT GAA TAG GCG GCG GTA CAA GGT GCT GGA AAG GGT GCG GTA CAC ACC TTG GCC CAG TTG AGC CAC AAT GCG CTG TTG | rc 1039–1116 | 78 |
| Bt 19 (27) | center | CCG CAG GGA GCT GAC CCT GAC GGT GCT TGA CAT TGT GGC TCT GTT CCC AAA CTA CGA CTC CCG TCG CTA CCC AAT CCG C | 696–774 | 79 |
| Bt 20 (28) | center | AAG CGA ACT CAG TGC CAT CAA GCA CAG AAA GCT GTT GGT TGT TGA TGC CAA TGT TGA ATG GGC GGC GGT ACA AGG | rc 1094–1168 | 75 |
| Bt 21 (29) | center | GGC CTC GAG AGG GTG TAG GGT CCA GAC TCC AGG GAC TAG GTG CGT TAC AAC CAA TTC CGC AGG GAG CTG ACC CTG | 640–714 | 75 |
| Bt 22 (30) | center | GTC CAC GGT ACC AGA CTT GCG GTA CAC AGC GCT TAG CAA GTT GCT AGA GGT GCC GTA AGC GAA CTC AGT GCC ATC AAG | rc 1147–1224 | 78 |
| Bt 23 (31) | 3' end | GTC ATC TCG GGT CCA GGT TTC ACG GGT GGT GAC CTT GTG CGC TTG AAC AGC TCG GGT AAC AAC ATC CAG AAC AGG GGT TAC | 1459–1539 | 81 |
| Bt 24 (32) | 3' end | ACC TGA CCC TGA CCC TGT AGC GGG TGC TAG TAG ATG GGA AGT GGA TTG GCA CCT CGA TGT AAC CCC TGT TCT GGA TGT T | rc 1519–1597 | 79 |
| Bt 25 (33) | 3' end | GCC TCT GAC AGC ATC ACT CAA ATC CCT GCT GTT AAG GGC AAC TTC CTT TTC AAC GGC TCG GTC ATC TCG GGT CCA GGT TTC | 1399–1470 | 72 |
| Bt 26 (34) | 3' end | GTT GCT GAA GAT GGA GCT GTT GCC CCA GTT CAC GTT CAA GTG GAT TAG GGT GGT CAC AGA AGC GTA CCT GAC CCT GAC CCT GTA | rc 1579–1659 | 81 |
| Bt 27 (35) | 3' end | ATC AGG GCC CCA ATG TTC TCC TAG ATT CAC CGT TCT GCT GAG TTC AAC AAC ATC ATT GCC TCT GAC AGC ATC ACT CAA | 1342–1419 | 78 |
| Bt 28 (36) | 3' end | CGA AGT AGC CGA AGT CCG AGG ACT GCA GGT TGT CAA GGC TAG TAG CCG TAG CTG GCA CCG TGT TGC TGA AGA TAG AGC TGT T | rc 1639–1720 | 82 |
| Bt 29 (37) | 3' end | CAC CGC TTG AGC CAC GTT TCC ATG TTC CGT TCG GGC TTC AGC AAC AGC TCT GTG AGC ATT ATC AGG GCC CCA ATG TTC | 1282–1359 | 78 |
| Bt 30 (38) | 3' end | GCG CAC ACC CAC GAT GTT GCC AAG AGA GCT GGT GAA AGC GTT GGC CGA TTC GAA GTA GCC GAA GTC CGA | rc 1702–1770 | 69 |
| Bt 31 (39) | 3' end | CCA CAG AAC AAC AAC GTG CCA CCT CGC CAA GGC TTC TCT CAC CGC TTG AGC CAC GTT TCC | 1243–1302 | 60 |
| Bt 32 (40) | 3' end | GGG ATG AAT TCG AAG CGG TCG ATG ATG ACA CCA GCC GTG CCA GAG AAG TTG CGC ACA CCC ACG ATG TTG CC | rc 1750–1820 | 71 |
| Bt 33 (41) | 3' end | CGC AAG TCT GGT ACC GTG GAC AGC TTG GAC GAG ATC CCT CCA CAG AAC AAC AAC GTG CCA | 1204–1263 | 60 |
| Bt 34 (42) | 3' end | CTC TAG ATC CCT ATG GTG GCT CAG CCT CCA GGG TAG CCG TCA CTG GGA TGA ATT CGA AGC GGT C | rc 1801–1854 | 64 |

[a]For each oligonucleotide, the name, gene fragment sequence, location in the complete ICP gene, and length (in bases) are shown. Nucleotide locations marked with rc indicate that the sequence of the oligonucleotide corresponds to the reverse complement of the nucleotide sequence of the top (coding) strand of the gene.

Several conditions were followed in the design of the oligonucleotides: i) All oligonucleotide overlaps were a minimum of 18 nt; ii) The 3'-most base of each oligonucleotide was chosen to be G or C; iii) The 5'-most base of each oligonucleotide was chosen adjacent to and downstream of a T residue in the sequence, in order to avoid problems with non-template addition of A residues at the 3' end of the opposite strand (Clark et al., Nucl. Acids Res., 16 (1988) 9677); iv) Extensive internal basepairing in each oligonucleotide was avoided where possible; and v) Basepairing between oligonucleotides used in all steps except the first (oligonucleotide annealing) step for each fragment was also avoided where possible.

Gene Expression in E. coli

Figures 4, 5:
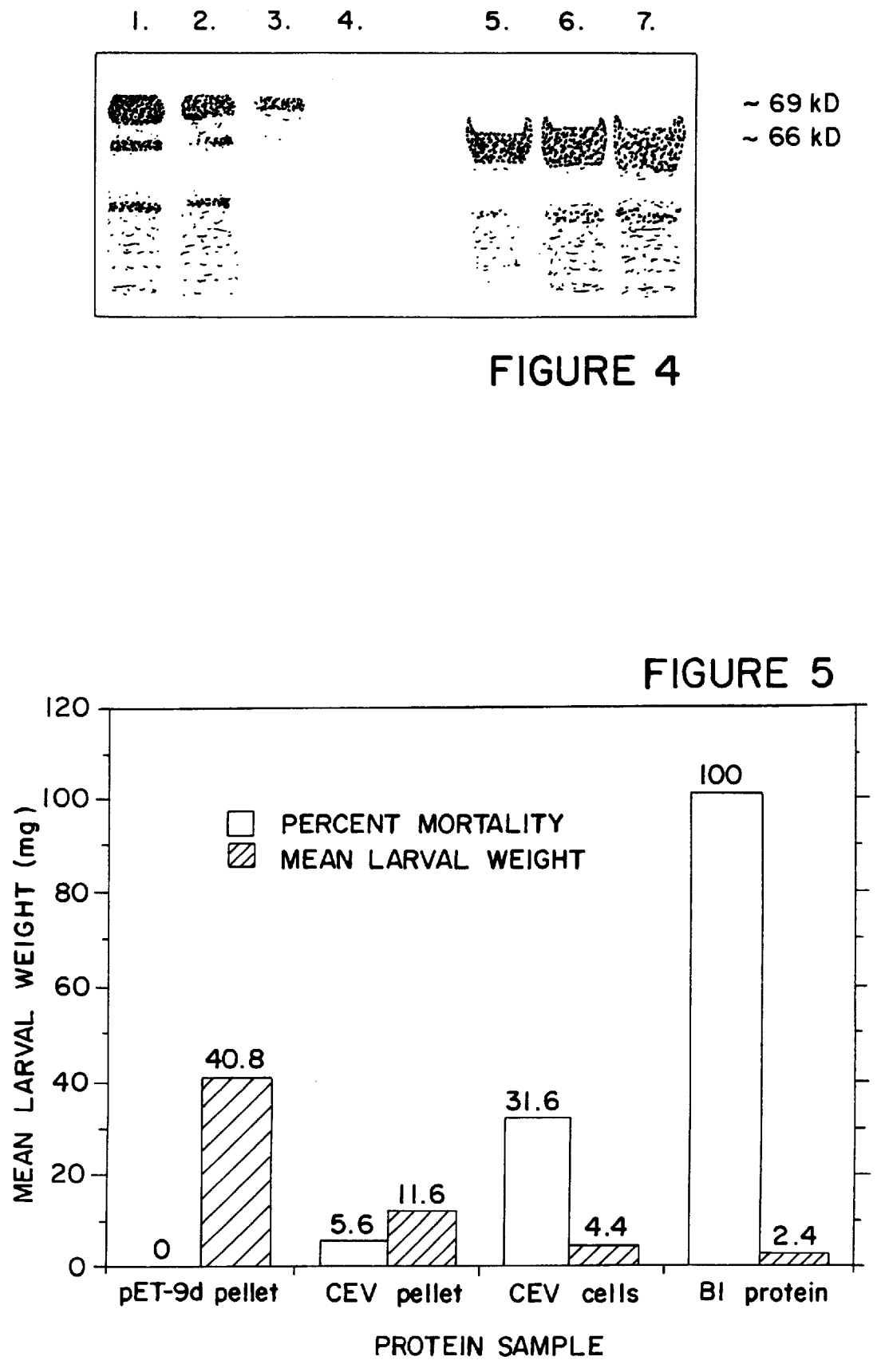
Figure 6:
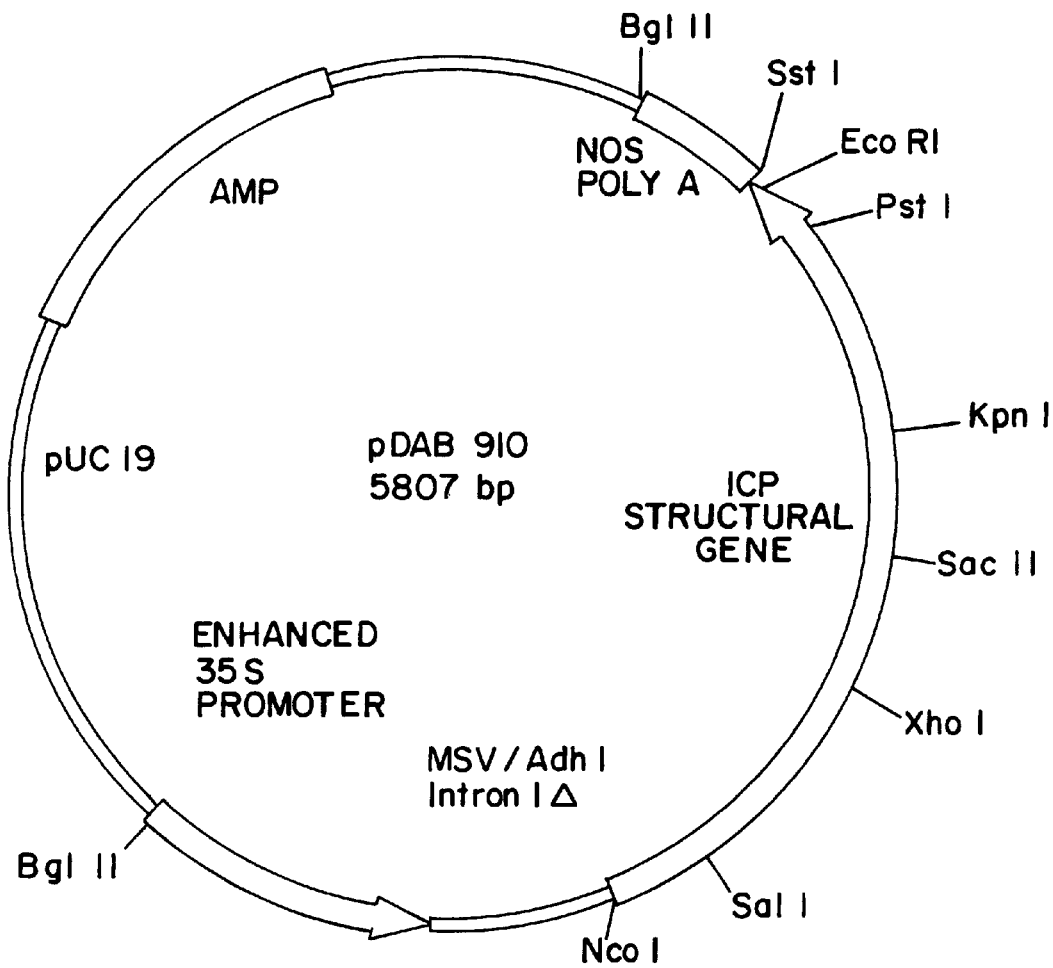

To demonstrate that a functional protein of correct size, antigenicity, and toxicity to Lepidopteran insects was encoded by the synthesized nucleotide sequence, expression studies were carried out in E. coli prior to the initiation of plant transformation experiments. To this end, the maize optimized DNA sequence coding for ICP was inserted in T7 expression plasmids, and E. coli extracts highly enriched in the ICP gene product were prepared. SDS-PAGE and immunoblot analysis demonstrated that the gene product was of the correct size and cross reacted with antiserum raised against purified native B. thuringiensis delta-endotoxin (FIG. 4). The biological action of the protein was demonstrated in M. sexta feeding assays (FIG. 5). Further verification of the success of engineering and synthesis strategies was provided by the demonstration that the ICP gene produced antigenically active protein of the correct size in transformed maize callus cells (FIG. 6). Feeding bioassays with H. virescens larvae revealed the insecticidal activity of the engineered protein. Together, these data demonstrate that the maize optimized nucleotide sequence produces a protein which shares several biological features (e.g., antigenicity, size, biological activity) with wildtype ICP isolated from nature.

Preparation of Recombinant DNA Vectors Containing the Synthetic Maize Optimized Bt ICP Gene The maize optimized nucleotide sequence coding for Bt ICP is expressed in plants at an enhanced level when compared to that observed with natural Bt structural genes. Expression of the maize optimized Bt ICP nucleotide sequence requires transformation of a plant cell with an appropriate vector. The maize optimized nucleotide sequence for Bt ICP was combined with a promoter functional in plants, where the structural gene and the promoter region being in such position and orientation with respect to each other that the structural gene can be expressed in a cell in which the promoter region is active, thereby forming a functional gene. The promoter regions include, but are not limited to, bacterial and plant promoter regions. In another aspect of the invention, the promoter is selected from the group consisting of inducible promoters, constitutive promoters, temporal or developmentally-regulated promoters, tissue-preferred, and tissue-specific promoters.

In an important aspect of the invention, the vector includes an MSV (Maize Streak Virus) leader sequence, a 35S promoter, and an enhancer specific for maize, such as an Adh intron 1 or Adh intron 6 as further described in the Examples.

To express the promoter region/structural gene combination, the DNA segment carrying the combination is contained by a cell. Combinations which include plant promoter regions are contained by plant cells, which, in turn, may be contained by plants or seeds. Combinations which include bacterial promoter regions are contained by bacteria, e.g., Bt or E. coli. Those in the art will recognize that expression in types of micro-organisms other than bacteria may in some circumstances be desirable and, given the present disclosure, feasible without undue experimentation.

Appropriate recombinant DNA vectors with which the maize optimized Bt ICP gene can be combined are further described in herein in the Examples.

Transformation of Maize with the Synthetic ICP Gene Vector and Transformation of all Plants with the Doubly Enhanced Promoter The recombinant DNA molecule carrying a maize optimized Bt ICP gene under promoter control can be introduced into plant tissue by any means known to those skilled in the art. The technique used for a given plant species or specific type of plant tissue depends on the known successful techniques. As novel means are developed for the stable insertion of foreign genes into plant cells and for manipulating the modified cells, skilled artisans will be able to select from known means to achieve a desired result.

The doubly enhanced promoters can be used to express foreign genes in maize as well as dicots or other monocots. More specifically, dicots include but are not limited to soybeans, legumes, rapeseed, cotton, sunflower, tomatoes, potatoes, sugar beets, alfalfa, cloves and peanuts. Monocots include but are not limited to maize, wheat, sorghum, oats, rye, barley, rice, millets, sugar cane and grasses.

In addition to using a doubly enhanced 35S or 19S promoter from cauliflower mosaic virus, other promoters may be modified by the teachings discussed herein. More specifically, promoters which may be modified with the MSV leader sequence adh1, adh6, or other introns (SEQ. ID. NOS. 43, 44, 45, 46 and 47) include but are not limited to octopine synthase promoter, nopaline synthase promoter and manopine synthetase promoter.

Plant promoters, can also be further modified by the teachings herein and include but are not limited to ribulose-1,6-biphosphate (RUBP) carboxylase small subunit (ssu), beta-conglycinin promoter, phaseolin promoter, ADH promoter, actin, ubiquitin, zein, oleosin, napin, ACP, heat-shock promoters, and tissue specific promoters or pollen-specific, embryo specific, corn silk specific, cotton fiber specific, root specific, seed endosperm specific promoters and the like.

Several techniques exist for introducing foreign genetic material into plant cells, and for obtaining plants that stably maintain and express the introduced gene. Such techniques include acceleration of genetic material coated onto microparticles directly into cells (U.S. Pat. Nos. 4,945,050 to Cornell and 5,141,131 to DowElanco). Plants may be transformed using Agrobacterium technology, see U.S. Pat. Nos. 5,177,010 to University of Toledo, 5,104,310 to Texas A&M, European Patent Application 0131624B1, European Patent Applications 120516, 159418B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to MaxPlanck, European Patent Applications 604662 and 627752 to Japan Tobacco, European Patent Applications 0267159, and 0292435 and U.S. Pat. No. 5,231,019 all to Ciba Geigy, U.S. Pat. Nos. 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, U.S. Pat. Nos. 5,472,869 and 5,384,253 both to Dekalb, WO9209696 and WO9321335 both to PGS. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Another variable is the choice of a selectable marker. The preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which code for resistance or tolerance to glyphosate; hygromycin; methotrexate; phosphinothricin (bar); imidazolinones, sulfonylureas and triazolopyrimidine herbicides, such as chlorosulfuron; bromoxynil, dalapon and the like.

In addition to a selectable marker, it may be desirous to use a reporter gene. In some instances a reporter gene may be used without a selectable marker. Reporter genes are genes which are typically not present or expressed in the recipient organism or tissue. The reporter gene typically encodes for a protein which provide for some phenotypic change or enzymatic property. Examples of such genes are provided in K. Weising et al. Ann. Rev. Genetics, 22, 421 (1988), which is incorporated herein by reference. A preferred reporter gene is the glucuronidase (GUS) gene.

Once introduced into the plant tissue, the expression of the structural gene may be assayed by any means known to the art, and expression may be measured as mRNA transcribed or as protein synthesized. Techniques are known for the in vitro culture of plant tissue, and in a number of cases, for regeneration into whole plants (EP Appln No. 88810309.0). Procedures for transferring the introduced expression complex to commercially useful cultivars are known to those skilled in the art.

Once plant cells expressing the gene under control of a plant expressible promoter are obtained, plant tissues and whole plants can be regenerated therefrom using methods and techniques well-known in the art. The regenerated plants are then reproduced by conventional means and the introduced genes can be transferred to other strains and cultivars by conventional plant breeding techniques.

Expression of the ICP Gene in Maize Cells

The functionality of the maize optimized Bt ICP gene in plant cells has been tested in maize transformation systems, in Black Mexican Sweet (BMS) protoplasts, and in stably transformed maize callus cultures. These studies indicated that the engineered ICP gene expressed well in maize and that the levels of accumulated ICP were sufficient to provide insect control in in vitro feeding assays.

Introduction of the gene into regenerable maize cultures by helium blast transformation as described in U.S. Pat. No. 5,141,131, provided fertile plants that expressed the gene. Plants grown from the seeds of transgenic maize plants also expressed the ICP gene in subsequent generations.

The following examples illustrate methods for carrying out the invention and should be understood to be illustrative of, but not limiting upon, the scope of the invention which is defined in the appended claims.

EXAMPLES

Example 1: Oligonucleotide Synthesis.

Oligonucleotides were synthesized on either the Applied Biosystems Inc., DNA synthesizer model 380A or model 390 using 0.2 $\mu$M columns and FOD phosphoramidites and standard cyanoethyl chemistry; synthesis was done in the Trityl-Off mode. Following synthesis on the Model 380A synthesizer, each oligonucleotide was cleaved off the column and deprotected at 50° C. for 1 hr. and dried down by evaporation at 50° C. The oligonucleotides were resuspended in 300 $\mu$l TE buffer (10 mM Tris HCl pH 8.0, 1 mM EDTA) and the concentration was determined by measuring the absorbance at 260 nm.

Oligonucleotides were purified by electrophoresis on 12% denaturing polyacrylamide gels (PAGE). A PAGE gel stock solution of 300 mls was made by dissolving 126 g urea in 30 ml 10×Tris Borate EDTA buffer (TBE; 1×TBE is 0.9 M Tris-borate, 2 mM EDTA) and 90 ml 40% acrylamide stock and adjusting the volume of the solution to 300 mls with H$_2$O. The gel solution was filtered through a 0.2 $\mu$m filter. 40 mls of the PAGE stock was used to pour a 5-well gel using a Hoeffer Sturdier gel apparatus. Polymerization was initiated by addition of 350 $\mu$l 10% ammonium persulfate and 35 $\mu$l TEMED prior to pouring.

Each oligonucleotide was prepared as follows: 300 to 500 $\mu$g of oligonucleotide was diluted to 60 $\mu$l with TE buffer, then 60 $\mu$l of formamide gel loading buffer (10 ml formamide, 10 mg xylene cyanol FF, 10 mg bromophenol blue, 200 $\mu$l 0.5 M EDTA pH 8.0) was added and the sample was boiled for 5 minutes and chilled on ice. The samples were loaded on the gel using a sequencing pipet tip. Electrophoresis was carried out in 1: TBE at 300 volts for 3 hrs.

Following the run the acrylamide gel was transferred to SaranWrap™, placed on a white background (e.g., X-Ray intensifying screen), and exposed to short wave UV light. The presence of the DNA bands, as well as the location of xylene cyanol and bromophenol blue dye markers, was visualized as a shadow on the white background.

The DNA bands of appropriate size were excised from the gel and the DNA was eluted by diffusion. Each gel slice was macerated with a glass rod and incubated in 1.5 ml of oligo elution buffer (100 mM Tris HCl pH 8.0, 500 mM NaCl, 5 mM EDTA) with constant agitation in a rolling drum at 37° C. for 16 hours. The polyacrylamide slurry was filtered through a 3 cc syringe containing a glasswool plug and an attached 0.2 $\mu$m filter. The eluted oligonucleotide was concentrated by centrifugation for 2 hrs. at 3000×g in a Centricon 10 spin column (molecular weight cut-off 10,000 D) at room temperature, and washed with 2 ml TE buffer by centrifugation as above in the same tube. The purified oligonucleotide was recovered in a final volume of 30 to 40 $\mu$l. Concentration was determined by measurement of the absorbance at 260 nm.

Figure 2:
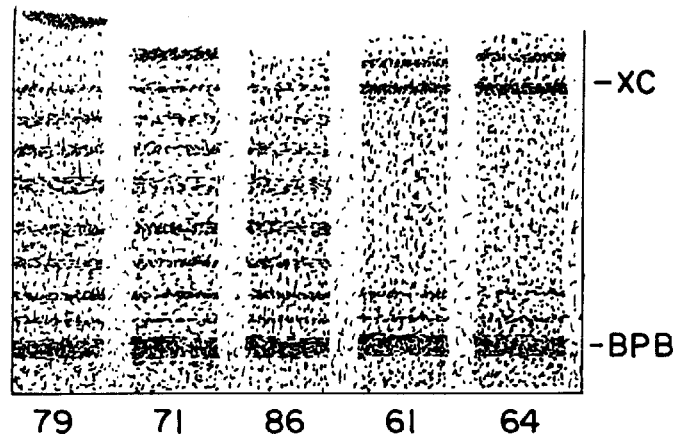

As an example of the result of oligonucleotide synthesis, the gel purification of oligonucleotides Bt6–Bt10 is shown in FIG. 2. FIG. 2 also shows two successful syntheses with the 380A synthesizer (Bt9 and Bt10) and two successful syntheses with the 390 synthesizer (Bt6 and Bt7).

Example 2: PCR Amplification.

All PCR amplifications were done in 100 $\mu$l reactions containing 20 mM Tris HCl pH 8.3, 1.5 mM MgCl, 25 mM KCl, 200 $\mu$M each of dATP, dGTP, dCTP and dTTP, and 5 units of Taq Polymerase (Perkin Elmer Cetus). Template and PCR primer concentrations varied depending on the step in the protocol. In the first PCR step, template was generated for each fragment by amplification with 0.5 $\mu$M of each of the primers of the first set (see FIG. 1) in the following regime: 1 minute denaturation at 94° C., 2 minutes annealing at 55° C. and 3 minutes extension at 72° C. for 30 cycles, followed by an additional extension period of 7 minutes at 72° C. The reaction products were loaded on a 5% native polyacrylamide gel and electrophoresed at 40 volts for 2.5 hours in 1×TBE. BRL 123 bp ladder run in a parallel lane was used as size standard. Following electrophoresis the gel was stained for 1 hr. in water containing 0.5 $\mu$g/ml ethidium bromide. The fragments of expected size were cut out of the gel and purified from the gel slice as described for the oligonucleotide purification (see above), with the exception that following filtering through glasswool and 0.2 $\mu$m filter, the DNA was concentrated by precipitation with 2.5 volumes of ethanol, 20 $\mu$g glycogen, and 0.05 volume of 8 M LiCl. The DNA was resuspended in 40 $\mu$l TE buffer. The second PCR step in the synthesis of each fragment was carried out in the same reaction mixture as the first step except that 5 $\mu$l of gel purified product of step 1 was used as template and the oligonucleotide concentration was 0.2 $\mu$M. The entire PCR reaction was electrophoresed on a 1% agarose gel and the bands of the expected size were excised and DNA was purified from the gel slices using the GeneClean Kit (Bi0101) and eluted in a final volume of 50 $\mu$l TE. All subsequent reactions were done as described for step 2.

Figure 3:
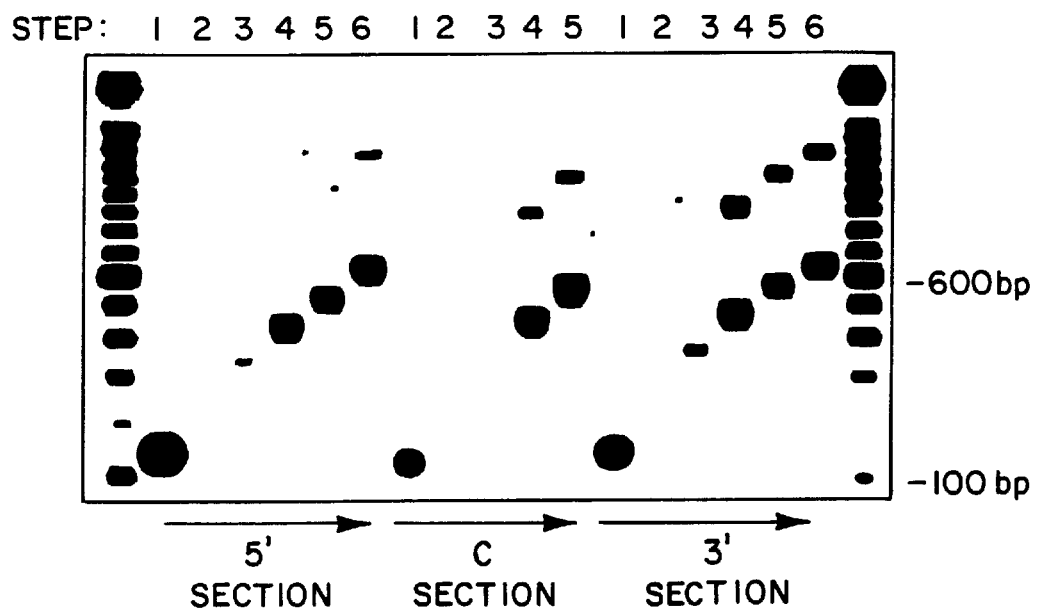

Each of the individual PCR steps gave large amounts of product of the expected size. In addition, in most cases bands of double the expected size could be seen, as well as other minor bands. All DNA products of appropriate size were gel purified and run on the gel shown in FIG. 3. This figure clearly demonstrates the stepwise addition of DNA sequence in consecutive PCR steps. The dimer-sized bands in each lane are considered to be artifacts of the electrophoresis, because gel purified DNA from monomer-size bands when re-run on a gel also gave this dimer-size band. The final product for each of the gene fragments was digested with the enzymes recognizing the restriction sites built in the end of each fragment (see FIG. 1A) and ligated to pBS DNA cut with the same enzymes. The ligation products were transformed into competent $E.$ $coli$ DH5α cells, and isolates carrying pBS plasmids containing the appropriate fragments were identified. DNA sequence of the ICP gene portion of these plasmids was determined, and five nucleotide differences from the Mze HD73 #6 trnc+ sequence were found. These changes were: 1) a conservative base change (G to T) in the 5' fragment at nt 639. (The "A" of the ATG start codon is designated base #1); 2) a conservative base change (A to G) in the center fragment at nt 1038; 3) a deletion of two G nucleotides in the center fragment at nt 657–658 which would cause a frameshift in the encoded polypeptide; 4) a base change (T to C) in the center fragment at nt 877 which would result in a serine to proline change; and 5) a deletion of one C nucleotide in the 3' fragment at nt 1401, also producing a frameshift. The latter three errors, which would have resulted in extensive frameshift and amino acid changes, were corrected by PCR mutagenesis as described in Example 3 (see below). Following the PCR correction, the center and 3' fragments were digested and cloned in pBS and the inserts of the resulting plasmids were sequenced to verify that during the correction process no other changes were introduced. Aside from the already existing conservative base changes in the 5' and center fragments (which were not corrected) the sequences were identical to the designed ICP (Mze HD73 #6 trnc+) sequence of SEQ. ID. NO. 1.

Example 3: Correction of ICP Gene Fragments.

All DNA manipulations and *E. coli* transformations were carried out according to standard procedures (Sambrook et al., *Molecular Cloning: A Laboratory Manual*, (1989) 2nd Ed., Cold Spring Harbor Press, Cold Spring Harbor, N.Y.; Ausubel et al., *Current Protocols in Molecular Biology*, (1987) John Wiley and Sons, New York, N.Y.). Following cloning of the three individual ICP gene fragments into pBluescript, the sequence was determined using the Sequenase Kit (US Biochemical, Cleveland, Ohio) using sequencing primers based on the modified ICP sequence or using some of the PCR synthesis primers described above.

Errors in the ICP gene fragments were corrected by PCR mutagenesis. For each correction two PCR reactions were set up. One PCR reaction amplified the 5' half of the fragment, using a 5' end oligonucleotide and the error-correcting oligonucleotide. The other PCR reaction amplified the 3' half of the fragment using the complementary error correction oligonucleotide and a 3' end oligonucleotide. The 5' and 3' corrected fragments were gel purified and joined together in a second step PCR reaction by amplification with only the 5' end and 3' end oligonucleotides as primers. Oligonucleotides used in the error correction were synthesized and gel purified as described above. PCR reaction conditions were as described above, except that annealing was done at 50° C. and 25 cycles were used. Fragments were gel purified using the GeneClean kit available from Bi0101.

Example 4: *E. coli* Expression.

For *E. coli* expression, the ICP was inserted as a 1862 base pair Nco I BamH I DNA fragment in the Nco I and BamH I sites of cytoplasmic expression vector pET-9d (Novagen, Madison, Wis.). One microgram of plasmid was transformed into 0.2 mls of competent cells of *E. coli* strain BL21 (which was available for purchase from Novagen, Madison, Wis.) and plated on LB plates containing kanamycin at 25 μg/ml (for plasmid pET-9d). Following overnight incubation at 37° C., colonies were scraped off the plate and resuspended in 10 mls of LB Broth containing the appropriate antibiotic and isopropyl-β-D-thiogalactoside (IPTG) at 1 mM. Cells were allowed to express protein for 3 hrs. during vigorous shaking at 37° C., then harvested by centrifugation at 1000×g for 10 minutes at 4° C.

For expression of pET-9d constructs, soluble and aggregated protein fractions were prepared as follows. Cell pellet was frozen and thawed twice, to aid in cell lysis, and the lysate was resuspended in 1 ml of lysis buffer (10 mM Tris HCl pH 8.0, 1 mM EDTA, 150 mM NaCl, 0.1% Triton X100, 100 g/ml DNaseI, 100 ug/ml RNaseH, 1 mg/ml lysozyme) and incubated at 37° C. until it was no longer viscous. Soluble protein was separated from aggregated denatured proteins by centrifugation at 4° C. for ten minutes. The insoluble pellet was resuspended in approximately 300 ul of the above lysis buffer. Both fractions had a final volume of 0.5 ml.

An abundant protein of molecular size 69 kD was present in the pellet fraction of both extracts produced from *E. coli* cells containing the cytoplasmic expression vector. This protein cross reacted with anti-serum raised against native delta-endotoxin purified from *B. thuringiensis* CryIA(c) cultures; the results of a representative protein gel immunoblot are shown in FIG. 4. Both *E. coli* (lane 1) and the pellet fraction prepared from the extract of those cells containing cytoplasmic expression vector (lanes 2 and 3) contained cross reactive protein. No cross reactive proteins were seen in equivalent amounts of pellet proteins of extract prepared from cells containing the cytoplasmic expression vector (lane 4).

The size of the anti-ICP cross-reactive protein produced in *E. coli* corresponds closely to the size of 68 kD predicted by the sequence of the ICP gene. The native ICP is slightly smaller (Mw 66 kD) compared to the product of the modified ICP gene (lanes 5, 6 and 7). In *B. thuringiensis*, the toxin is produced as a 130 kD protoxin. Upon ingestion by Lepidopteran insects, the protoxin is solubilized and activated by proteolytic cleavage. This proteolysis produces an active toxin moiety of 60–70 kD, depending on the strain of *B. thuringiensis*. In all Cry1 ICPs, proteolytic processing occurs in the center of the protoxin, and separates the toxin moiety from the C-terminal domain. Processing also occurs at the extreme N-terminus between amino acids Arg 28 and Ile 29, and is probably carried out by a serine-type protease. Amino terminal protein sequencing of trypsin activated protoxin of Cry1A(b) and Cry1C identified isoleucine at position 29 as the N-terminus (Hofte et al., *Microbiological Rev.,* 53 (1989) 242). Since the sequence of the Mze HD73 #6 trnc+ gene includes this putative serine protease site, cleavage at this site by serine protease activity in the *E. coli* extract would remove the N-terminal 28 amino acids. The result would be a product that is ≈3 kD smaller than the gene product predicted from the sequence of the gene. A protein of this size is seen as a faint band (at 66 kD) which comigrates with the native ICP toxin. The extracted protein was not quantified because the protein itself is insoluble and aggregates with cellular debris.

Example 5: Protein Concentrations Expressed by *E. coli.*

Protein concentrations were determined using the BioRad protein assay. Proteins were analyzed on 12.5% sodium dodecyl sulfate-polyacrylamide gels (SDS-PAGE) made in a Hoeffer Mighty Small minigel device, or on a Daiichi minigel device according to the manufacturers' recommendations. Staining for protein was done as described (Sambrook et al., *Molecular Cloning: A Laboratory Manual*, (1989), 2nd Ed., Cold Spring Harbor Press, Cold Spring Harbor, N.Y.), ICP was specifically detected by protein gel blot analysis (Western blotting) with rabbit antiserum raised against purified *B. thuringiensis* HD73 toxin, using the ECL Western blotting and detection system (Amersham, Arlington Heights, Ill.). Proteins were transferred from the gel to a Hybond-ECL nitrocellulose membrane (Amersham) by transfer using a Hoeffer SemiDry blotter at 0.5 mA/cm$^2$ of gel for 90 min. The membrane was incubated with the blocking reagent TBS-Tween-Milk (TBTM: 25 mM Tris HCl pH 7.4, 136 mM NaCl, 2.7 mM KCl, 0.1% Tween 20, 5% non-fat drymilk) at room temperature for 1 hr. Next, the membrane was incubated with primary antiserum at a 1:500 dilution in blocking reagent, followed by washing three times in 100 ml TBS-Tween (no milk) at room temperature for 10 minutes. The membrane was incubated for 1 hr. in blocking reagent containing secondary antiserum (goat anti-rabbit-IgG conjugated to horseradish peroxidase; Bio-Rad Laboratories, Hercules, Calif.), then washed three times in 100 ml TBS-Tween at room temperature for 10 minutes. The filter was incubated in 10 mls of reagent A+B (1:1; ECL kit) for 1 minute, excess liquid was drained off, and the membrane was exposed to Hyperfilm-ECL film for 10 sec. to 1 minute. ECL film was processed using standard developer and fixer. ICP signals were scanned with a Model 620 video densitometer (Bio-Rad) and the concentration was determined by comparison with scans of ICP standards electrophoresed on the same gel using 1-D Analyst software (Bio-Rad). FIG. 4 illustrates expression of ICP in *E. coli* and the concentration of such expressions.

Example 6: Feeding Assays.

ICP expressed in *E. coli* and extracted as indicated in Example 4 was used for feeding assays in Manduca sexta (tobacco hornworm). Neonate larvae were allowed to feed on artificial diets into which ICP or control samples were incorporated. After 4 days, their weights and mortality were determined.

The results of testing of *E. coli* extracts in *M. sexta* feeding assays (FIG. 5) indicated that the ICP encoded by Mze HD73 #6 trnc+ has Lepidopteran toxicity. Both the pellet fraction of *E. coli* extracts, as well as cells expressing the ICP, caused significant growth inhibition and mortality. However, the ICP containing *E. coli* extracts and cells were less toxic to *Manduca larvae* than was the purified native ICP. This may be explained by the fact that the lCP produced in *E. coli* was highly insoluble. It is possible that, due to the aggregation, the effective ICP concentration is much lower than the protein concentration would indicate.

Example 7: Construction of Plant Expression Plasmids.

A. Construction of a doubly-enhanced CaMV 35S Promoter:

This section describes molecular manipulations which result in a duplication of the expression-enhancer element of a plant promoter. This duplication has been shown (Kay et al., *Science* 236 (1987) 1299) to result in increased expression in tobacco plants of marker genes whose expression is controlled by such a modified promoter. [Note: The sequences referred to in this discussion are derived from the Cabb S strain of Cauliflower Mosaic Virus (CaMV). They are available as the MCASTRAS sequence of GenBank, and published by Franck et al. (*Cell* 21 (1980) 285). All of the DNA sequences are given in the conventional 5' to 3' direction. The starting material is plasmid pUC13/35S(−343) as descirbed by Odell et al. (Nature 313 (1985) 810). This plasmid comprises, starting at the 3' end of the Sma I site of pUC13 (Messing, *Methods in Enzymology* 101 (1983) 20), and reading on the strand contiguous to the noncoding strand of the lacZ gene of pUC13, nucleotides 6495 to 6972 of CaMV, followed by the linker sequence CATCGATG (which encodes a Cla I recognition site), followed by CaMV nucleotides 7089 to 7443, followed by the linker sequence CAAGCTTG, the latter sequence comprising the recognition sequence for Hind III, which is then followed by the remainder of the pUC13 plasmid DNA.

1. pUC13/35S(-343) DNA was digested with Cla I and Nco I, the 3429 base pair (bp) large fragment was separated from the 66 bp small fragment by agarose gel electrophoresis, and then purified by standard methods.

2. pUC13/35S(−343) DNA was digested with Cla I, and the protruding ends were made flush by treatment with T4 DNA polymerase. The blunt-ended DNA was the ligated to synthetic oligonucleotide linkers having the sequence CCCATGGG, which includes an Nco I recognition site. The ligation reaction was transformed into competent *Escherichia coli* cells, and a transformant was identified that contained a plasmid (named pOO#l) that had an Nco I site positioned at the former Cla I site. DNA of pOO#1 was digested with Nco I and the compatible ends of the large fragment were religated, resulting in the deletion of 70 bp from pOO#1, to generate intermediate plasmid pOO#l NcoΔ.

3. pOO#1 NcoΔ DNA was digested with EcoR V, and the blunt ends were ligated to Cla I linkers having the sequence CATCGATG. An *E. coli* transformant harboring a plasmid having a new Cla I site at the position of the previous EcoR V site was identified, and the plasmid was named pOO#l NcoΔ RV>Cla.

4. DNA of pOO#1 NcoΔ RV>Cla DNA was digested with Cla I and Nco I, and the small (268 bp) fragment was purifed from an agarose gel. This fragment was then ligated to the 3429 bp Cla I/Nco I fragment of pUC13/35S(−343) prepared above in step 1, and an *E. coli* transformant that harbored a plasmid having Cla I/Nco I fragments 3429 and 268 bp was identified. This plasmid was named pUC13/35S En.

5. pUC13/35S En DNA was digested with Nco I, and the protruding ends were made blunt by treatment with T4 DNA polymerase. The treated DNA was then cut with Sma I, and was ligated to Bgl II linkers having the sequence CAGATCTG. An *E. coli* transformant that harbored a plasmid in which the 416 bp Sma I/Nco I fragment had been replaced with at least two copies of the Bgl II linkers was identified, and named p35S $En^2$. [NOTE: The randomization of these Bgl II linkers generate, besides Bgl II recognition sites, also Pst I recognition sites, CTGCAG].

The DNA structure of p35s $En^2$ is as follows: Beginning with the nucleotide that follows the third C residue of the Sma I site on the strand contiguous to the noncoding strand of the lacZ gene of pUC13; the linker sequence CAGATCTGCAGATCTGCATGGGCGATG (SEQ. ID. NO. 48), followed by CaMV nucleotides 7090 to 7344, followed by the Cla I linker sequence CATCGATG, followed by CaMV nucleotides 7089 to 7443, followed by the Hind III linker sequence CAAGCTT, followed by the rest of pUC13 sequence. This structure has the feature that the enhancer sequences of the CaMV 35S promoter, which lie in the region upstream of the EcoR V site in the viral genome (nts 7090 to 7344), have been duplicated. This promoter construct incorporates the native 35S transcription start site, which lies 11 nucleotides upstream of the first A residue of the Hind III site.

Example 7B.

Plasmids utilizing the 35S promoter and the Agrobacterium NOS Poly A sequences: The starting material for the first construct is plasmid pBI221, purchased from CLONTECH (Palo Alto, Calif.). This plasmid contains a slightly modified copy of the CaMV 35S promoter, as described in Bevan et al. (1985), Baulcombe et al., (1986), Jefferson et al., (1986, 1987) and Jefferson (1987). Beginning at the 3' end of the Pst I site of pUC19 (Yanisch-Perron et al., 1985), and reading on the same strand as that which encodes the lacZ gene of pUC19, the sequence is comprised of the linker nucleotides GTCCCC, followed by CaMV nucleotides 6605 to 7439 (as described in Example 7A), followed by the linker sequence GGGGACTCTAGA GGATCCCCGGGTGGTC AGTCCCTT (SEQ. ID. NO. 49), wherein the underlined bases represent the BamH I recognition sequence. These bases are then followed by 1809 bp comprising the coding sequence of the *E. coli* uidA gene, which encodes the β-glucuronidase (GUS) protein, and 55 bp of 3' flanking bases that are derived from the *E. coli* genome (Jefferson, 1986), followed by the Sac I linker sequence GAGCTC, which is then followed by the linker sequence GAATTTCCCC (SEQ. ID. NO. 50). These bases are followed by the RNA transcription termination/polyadenylation signal sequences derived from the *Agrobacterium tumefaciens* nopaline synthase (NOS) gene, and comprise the 256 bp Sau3A I fragment corresponding to nucleotides 1298 to 1554 of DePicker et al. (1982), followed by two C residues, the Eco RI recognition sequence GAATTC, and the rest of pUC19.

1. pBI221 DNA was digested with EcoR I and BamH I, and the 3507 bp fragment was purified from an agarose gel. pRAJ275 (CLONTECH, Jefferson, 1987) DNA was digested with EcoR I and Sal I, and the 1862 bp fragment was purified from an agarose gel. These two fragments were mixed together, and complementary synthetic oligonucleotides having the sequence GATCCGGATCCG (SEQ. ID. NO. 51) and TCGACGGATCCG (SEQ. ID. NO. 52) were added. [These oligonucleotides when annealed have protruding single-stranded ends compatible with the protruding ends generated by BamH I and Sal I.] The fragments were ligated together, and an *E. coli* transformant harboring a plasmid having the appropriate DNA structure was identified by restriction enzyme analysis. DNA of this plasmid, named pKA881, was digested with Bal I and Eco RI, and the 4148 bp fragment was isolated from an agarose gel. DNA pBI221 was similarly digested, and the 1517 bp Eco RI/Bal I fragment was gel purified and ligated to the above pKA881 fragment, to generate plasmid pKA882.

2. pKA882 DNA was digested with Sac I, the protruding ends were made blunt by treatment with T4 DNA polymerase, and the fragment was ligated to synthetic BamH I linkers having the sequence CGGATCCG. An *E. coli* transformant that harbored a plasmid having BamH I fragments of 3784 and 1885 bp was identified and named pKA882B.

3. pKA882B DNA was digested with BamH I, and the mixture of fragments was ligated. An *E. coli* transformant that harbored a plasmid that generated a single 3783 bp fragment upon digestion with BamH I was identified and named p35S/NOS. This plasmic has the essential DNA structure of pBI221, except that the coding sequences of the GUS gene have been deleted. Therefore, CaMV nucleotides 6605 to 7439 are followed by the linker sequence GGGGAC TCTAGAGGATCCCGAATTTCCCC (SEQ. ID. NO. 53), where the single underlined bases represent an Xba I site, and the double underlined bases represent a BamH I site.

The linker sequence is then followed by the NOS Polyadenylation sequences and the rest of pBI221.

4. p35S/NOS DNA was digested with EcoR V and Pst I, and the 3037 bp fragment was purified and ligated to the 534 bp fragment obtained from digestion of p35S En$^2$ DNA with EcoR V and Pst I. An *E. coli* transformant was identified that harbored a plasmid that generated fragments of 3031 and 534 bp upon digestion with EcoR V and Pst I, and the plasmid was named p35S En$^2$/NOS. This plasmid contains the duplicated 35S promoter enhancer region described for p35S En$^2$ in Example 7A Step 5, the promoter sequences being separated from the NOS polyadenylation sequences by linker sequences that include unique Xba I and BamH I sites.

Example 7C

Construction of a synthetic untranslated leader

This example describes the molecular manipulations used to construct a DNA fragment that includes sequences which comprise the 5' untranslated leader portion of the major rightward transcript of the Maize Streak Virus (MSV) genome. The MSV genomic sequence was published by Mullineaux et al., (1984), and Howell (1984), and the transcript was described by Fenoll et al. (1988). The entire sequence, comprising 154 bp, was constructed in three stages (A, B, and C) by assembling blocks of synthetic oligonucleotides.

1. The A Block: Complementary oligonucleotides having the sequence GATCCAGCTGAAGGCTCGACAAGGCA-GATCCACGGAGGAGCTGATATTTGGTGGACA (SEQ. ID. NO. 54) and AGCTTGTCCACCAAATATCAGCTC-CTCCGTGGATCTGCCTTGTCCAGCCTTCAGCTG (SEQ. ID. NO. 55) were synthesized and purified by standard procedures. Annealing of these nucleotides into double-stranded structures leaves 4-base single stranded protruding ends [hereinafter referred to as "sticky ends"] that are compatible with those generated by BamH I on one end of the molecule (GATC), and with Hind III-generated single stranded ends on the other end of the molecule (AGCT). Such annealed molecules were ligated into plasmid pBluescript SK(–) [hereinafter called pBSK; Stratagene Cloning Systems, LaJolla, Calif.], that had been digested with BamH I and Hind III. The sequence of these oligonucleotides is such that, when ligated onto the respective BamH I and Hind III sticky ends, the sequences of the respective recognition sites are maintained. An *E. coli* transformant harboring a plasmid containing the oligonucleotide sequence was identified by restriction enzyme analysis, and the plasmid was named pMSV A.

2. The B Block: Complementary oligonucleotides having the sequences AGCTGTGGATAGGAGCAACCCTATC-CCTAATATACCAGCACCACCAAGTCAGGGCAA T CCCGGG (SEQ. ID. NO. 56) and TCGA CCCGGGATTGCCCTGACTTGGTGGTGCTGGTATAT TAGGGATAGGGTTGCTCC TATCCAC (SEQ. ID. NO. 57) were synthesized and purified by standard procedures. The underlined bases represent the recognition sequence for restriction enzymes Sma I and Xma I. Annealing of these nucleotides into double-stranded structures leaves 4-base sticky ends that are compatible with those generated by Hind III on one end of the molecule (AGCT), and with Sal I-generated sticky ends on the other end of the molecule (TCGA). The sequence of these oligonucleotides is such that, when ligated onto the Hind III sticky ends, the recognition sequence for Hind III is destroyed.

DNA of pMSV A was digested with Hind III and Sal I, and was ligated to the above annealed oligonucleotides. An E. coli transformant harboring a plasmic containing the new oligonucleotides was identified by restriction enzyme site mapping, and was named pMSV AB.

3. The C Block: Complementary oligonucleotides having the sequences CCGGGCCATTTGTTCCAGGCACGG-GATAAGCATTCAG CCATGGGATATCAAGCTTGGATCCC (SEQ. ID. NO. 58) and TCGAG GGATCCAAGCTTGATATCCCATGGCTGAATGCTT ATCCCGTGCCTGGAACAA ATGGC (SEQ. ID. NO. 59) were synthesized and purified by standard procedures. The oligonucleotides incorporate bases that comprise recognition sites (underlined) for Nco I (CCATGG), EcoR V (GATATC), Hind III (AAGCTT), and BamH I (GGATCC). Annealing of these nucleotides into double-stranded structures leaves 4-base sticky ends that are compatible with those generated by Xma I on one end of the molecule (CCGG), and with Xho I-generated sticky ends on the other end of the molecule (TCGA). Such annealed molecules were ligated into pMSV AB DNA that had been digested with Xma I and Xho I. An E. coli transformant harboring a plasmid containing the oligonucleotide sequence was identified by restriction enzyme site analysis, and DNA structure was verified by sequence analysis. The plasmid was named pMSV CPL; it contains the A, B and C blocks of nucleotides in sequential order ABC. Together, these comprise the 5' untranslated leader sequence ("L") of the MSV coat protein ("CP") gene. These correspond to nucleotides 167 to 186, and 188 to 317 of the MSV sequence of Mullineaux et al., (1984), and are flanked on the 5' end of the BamH I linker sequence GGATCCAG, and on the 3' end by the linker sequence GATATCAAGCTTGGATCCC (SEQ. ID. NO. 60). [Note: An A residue corresponding to base 187 of the wild type MSV sequence was inadvertently deleted during cloning.]

4. Bgl II Site Insertion: pMSV CPL DNA was digested at the Sma I site corresponding to base 277 of the MSV genomic sequence, and the DNA was ligated to Bgl II linkers having the sequence CAGATCTG. An E. coli transformant harboring a plasmic having a unique Bgl II site at the position of the former Sma I site was identified and verified by DNA sequence analysis, and the plasmid was named pCPL-Bgl.

Example 7D

Construction of a deleted version of the maize alcohol dehydrogenase 1 (Adh1) intron 1

The starting material is plasmid pVW119, which was obtained from V. Walbot, Stanford University, Stanford, Calif. This plasmid contains the DNA sequence of the maize Adh1.S gene, including intron 1, from nucleotides 119 to 672 [numbering of Dennis et al. (1984)], and was described in Callis et al. (1987). In pVW119, the sequence following base 672 of Dennis et al. (1984) is GAC<u>GGATCC</u>, where the underlined bases represent a BamH I recognition site. The entire intron 1 sequence, with 14 bases of exon 1, and 9 bases of exon 2, can be obtained from this plasmid on a 556 bp fragment following digestion with Bcl I and BamH I.

1. Plasmid pSG3525a(Pst) DNA was digested with BamH I and Bcl I, and the 3430 bp fragment was purified from an agarose gel. [NOTE: The structure of plasmid pSG3525a (Pst) is not directly relevant to the end result of this construction series. It was constructed during an unrelated series, and was chosen because it contained restriction recognition sites for both Bcl I and BamH I, and lacks Hind III and Stu I sites. Those skilled in the art will realize that other plasmids can be substituted at this step with equivalent results.] DNA of plasmid pVW119 was digested with BamH I and Bcl I, and the gel purified fragment of 546 bp was ligated to the 3430 bp fragment. An E. coli transformant was identified that harbored a plasmid that generated fragments of 3430 and 546 upon digestion with BamH I and Bcl I. This plasmid was named pSG AdhA1.

2. DNA of pSG AdhA1 was digested with Hind III, [which cuts between bases 209 and 210 of the Dennis et al., (1984) sequence, bottom strand], and with Stu I, which cuts between bases 554 and 555. The ends were made flush by T4 DNA polymerase treatment, and then ligated. An E. coli transformant that harbored a plasmid lacking Hind III and Stu I sites was identified, and the DNA structure was verified by sequence analysis. The plasmid was named pSG AdhA1Δ. In this construct, 344 bp of DNA have been deleted from the interior of the intron 1. The loss of these bases does not affect splicing of this intron. The functional intron sequences are obtained on a 213 bp fragment following digestion with Bcl I and BamH I.

3. DNA of plasmid pCPL-Bgl (Example 7C Step 4), was digested with Bgl II, and the linearized DNA was ligated to the 213 bp Bcl I/BamH I fragment containing the deleted version of the Adh1.S intron sequences from pSG AdhA1A. [Note: The sticky ends generated by digestion of DNA with Bgl II, Bcl I, and BamH I are compatible, but ligation of the BamH I or Bcl I sticky ends onto ones generated by Bgl II creates a sequence not cleaved by any of these three enzymes.] An E. coli transformant was identified by restriction enzyme site mapping that harbored a plasmid that contained the intron sequences ligated into the Bgl II site, in the orientation such that the Bgl II/Bcl I juncture was nearest the 5' end of the MSV CPL leader sequence, and the Bgl II/BamH I juncture was nearest the 3' end of the CPL. This orientation was confirmed by DNA sequence analysis. The plasmid was named pCPL A1I1Δ. The MSV leader/intron sequences can be obtained from this plasmid by digestion with BamH I and Nco I, and purification of the 373 bp fragment.

Example 7E

Construction of plant expression vectors based on the enhanced 35S promoter, the MSV CPL, and the deleted version of the Adh1 intron 1

1. DNA of plasmid p35S En$^2$/NOS was digested with BamH I, and the 3562 bp linear fragment was ligated to a 171 bp fragment prepared from pMSV CPL DNA digested with BamH I. This fragment contains the entire MSV CPL sequence described in Example 7C. An E. coli transformant was identified by restriction enzyme site mapping that harbored a plasmid that contained these sequences in an orientation such that the Nco I site was positioned near the NOS Poly A sequences. This plasmid was named p35S En$^2$ CPL/NOS. It contains the enhanced version of the 35S promoter directly contiguous to the MSV leader sequences, such that the derived transcript will include the MSV sequences in its 5' untranslated portion.

2. DNA of plasmid pKA882 (see Example 7B Step 1) was digested with Hind III and Nco I, and the large 4778 bp fragment was ligated to an 802 bp Hind III/Nco I fragment containing the enhanced 35S promoter sequences and MSV leader sequences from p35S En$^2$ CPL/NOS. An E. coli transformant harboring a plasmid that contained fragments of 4778 and 802 bp following digestion with Hind III and Nco I was identified, and named pDAB310. In this plasmid, the enhanced version of the 35S promoter is used to control expression of the GUS gene. The 5' untranslated leader portion of the transcript contains the leader sequence of the MSV coat protein gene.

3. DNA of plasmid pDAB310 was digested with Nco I and Sac I. The large 3717 bp fragment was purified from an agarose gel and ligated to complementary synthetic oligonucleotides having the sequences CGGTACCTCGAGT-TAAC (SEQ. ID. NO. 61) and CATGGTTAACTCGAGG-TACCGAGCT (SEQ. ID. NO. 62). These oligonucleotides, when annealed into double stranded structures, generate molecules having sticky ends compatible with those left by Sac I, on one end of the molecule, and with Nco I on the other end of the molecule. In addition to restoring the sequences of the recognition sites for these two enzymes, new sites are formed for the enzymes Kpn I (GGTACC), Xho I (CTCGAG), and Hpa I (GTTAAC). An *E. coli* transformant was identified that harbored a plasmid that contained sites for these enzymes, and the DNA structure was verified by sequence analysis. This plasmid was named pDAB1148.

4. DNA of plasmid pDAB1148 was digested with Bam HI and Nco I, the large 3577 bp fragment was purified from an agarose gel and ligated to a 373 bp fragment purified from pCPL A1I1Δ (Example 7D Step 3) following digestion with Bam HI and Nco I. An *E. coli* transformant was identified that harbored a plasmid with BamH I and Nco I, and the plasmid was named pDAB303. This plasmid has the following DNA structure: beginning with the base after the final G residue of the Pst I site of pUC19 (base 435), and reading on the strand contiguous to the coding strand of the lacZ gene, the linker sequence ATCTGCATGGGTG (SEQ. ID. NO. 63), nucleotides 7093 to 7344 of CaMV DNA, the linker sequence CATCGATG, nucleotides 7093 to 7439 of CaMV, the linker sequence GGGGACTCTAGAGGATC-CAG (SEQ. ID. NO. 64), nucleotides 167 to 186 of MSV, nucleotides 188 to 277 of MSV, a C residue followed by nucleotides 119 to 209 of Adh1.S, nucleotides 555 to 672 of maize Adh1.S, the linker sequence GACGGATCTG, nucleotides 278 to 317 of MSV, the polylinker sequence GTTAACTCGAGGTACCGAGCTCGAATTTCCCC (SEQ. ID. NO. 65) containing recognition sites for Hpa I, Xho I, Kpn I, and Sac I, nucleotides 1298 to 1554 of NOS, and a G residue followed by the rest of the pUC19 sequence (including the EcoR I site). It is noteworthy that the junction between nucleotide 317 of MSV and the long polylinker sequence creates an Nco I recognition site.

5. DNA of plasmid pDAB303 was digested with Nco I and Sac I, and the 3939 bp fragment was ligated to the 1866 bp fragment containing the GUS coding region prepared from similarly digested DNA of pKA882. The appropriate plasmid was identified by restriction enzyme site mapping, and was named pDAB305. This plasmid has the enhanced promoter, MSV leader and Adh1 intron arrangement of pDAB303, positioned to control expression of the GUS gene.

6. DNA of plasmid pKA882 was digested with Xba I and Nco I and the 5687 bp fragment was ligated to annealed synthetic oligonucleotides having the sequence CTAGAG-GATC (SEQ. ID. NO. 66) and CATGGATCCT (SEQ. ID. NO. 67). These oligonucleotides when annealed form a double-stranded structure having Xba I- and Nco I-compatible sticky ends. A recombinant plasmid lacking a Sal I site was identified by restriction enzyme mapping, verified by DNA sequence analysis, and was named pDAB349.

7. DNA of plasmid p35S En²/NOS was digested with Xba I and EcoR I, and the large fragment (3287 bp) was ligated to a 2152 bp fragment containing the GUS coding region and NOS polyadenylation region from similarly-digested pDAB349. A plasmid having the appropriate structure was identified by restriction site mapping, and was named pDAB313.

8. DNA of plasmid pDAB313 was digested with Xba I and Sac I, and the large 3558 bp fragment was ligated to a 1889 bp fragment prepared from similarly-cut DNA of pKA882. A plasmid having the appropriate structure was identified by restriction site mapping and was named pDAB348.

9. DNA of plasmid pDAB348 was digested with BamH I, and the large fragment (5437 bp) was ligated to a 213 bp Bcl I/BamH I fragment containing the deleted version of the Adh1.S intron 1, from pSG AdhA1Δ (Example 7D Step 2). A plasmid having the appropriate structure was identified by restriction site mapping and was named pDAB353.

Example 7F

The starting material is plasmid pIC35. This plasmid contains the 845 bp Sma I/Hind III fragment from pUC13 35S (−343) (see Section C of this example), ligated into the Nru I and Hind III sites of pIC19R (Marsh et al., *Gene*, 32 (1984) 481), in the orientation such that the Hind III recognition site is maintained. The source of the *A. tumefaciens* ORF25/26 sequences is plasmid pIC1925. This plasmid contains the 713 bp Hinc II fragment comprised by nucleotides 21728 to 22440 of *A. tumefaciens* pTi 15955 T-DNA (Barker et al., *Plant Molec. Biol.* 2 (1983) 335), ligated into the Sma I site of pIC19H (Marsh et al., *Gene*, 32 (1984) 481), in the orientation such that the BamH I site of pIC19H is adjacent to the ORF 25 end of the T-DNA fragment.

1. pIC 19R35/A: DNA of plasmid pIC35 was digested with BamH I, and ligated to the 738 bp fragment prepared by digestion of pIC1925 DNA with BamH I and Bgl II. An *E. coli* transformant was identified that harbored a plasmid in which a BamH I site was present positioned between the 35S promoter fragment, and the ORF 25/26 Poly A fragment. This plasmid was named pIC 19R35/A. (Note: Ligation of the compatible sticky ends generated by BamH I and Bgl II generates a sequence that is not a recognition site for either enzyme.)

2. pIC35/A: DNA of pIC 19R35/A was digested with Sma I at its unique site, and the DNA was ligated to Bgl II linkers having the sequence CAGATCTG. [NOTE: The randomization of these BgI II linkers generates, besides Bgl II recognition sites, also Pst I recognition sites, CTGCAG]. An *E. coli* transformant was identified that had at least two copies of the linkers (and therefore new Bgl II and Pst I sites) at the position of the former Sma I site. This plasmid was named pIC35/A.

3. pIC 20RΔ: DNA of plasmid pIC 20R (Marsh et al., *Gene*, 32 (1984) 481) was digested with Nru I and Sma I, and the blunt ends of the large fragment were ligated together. An *E. coli* transformant was identified that harbored a plasmid that lacked Nru I, Sma I, Hind III, Sph I, Pst I, Sal I, Xba I, and BamH I sites. This plasmid was called pIC 20RΔ.

4. pSG Bgl 3525 (Pst): DNA of pIC 2OR Δ was digested with Bgl II, and was ligated to the 1625 bp Bgl II fragment of pIC35/A. An *E. coli* transformant was identified that harbored a plasmid that contained the 35S promoter/ORF 25 poly A sequences. Restriction enzyme site mapping revealed these sequences to be in the orientation such that the unique Kpn I and Xho I sites of pIC 20RΔ are positioned at the 3' end of the ORF 25 Poly A sequences. This plasmid was named pSG Bgl 3525 (Pst)

5. pSG 3525 a (Pst): DNA of pSG Bgl 3525 (Pst) was digested with Bgl II under conditions in which only one of the two Bgl II sites of the molecule were cleaved. The 4301 bp linear fragments were ligated to synthetic adapter oligonucleotides having the sequence GATCG<u>TGATCAC</u> (SEQ. ID. NO. 68), where the underlined bases represent the Bcl I recognition sequence. An *E. coli* transformant was identified that had a Bcl I site at the position of the former Bgl II site positioned 5' to the 35S promoter. This plasmid was named pSG 3525 a (Pst)

6. pDAB 218: DNA of plasmid pIJ4104 (see Example 8) was digested with Sma I, and the 569 bp fragment was purified from an agarose gel. DNA of plasmid pSG 3525 a (Pst) (see above) was linearized by digestion at the unique Hinc II that lies between the 35S promoter and ORF poly A sequences, and the linear fragment was ligated to the 569 bp bar gene fragment. An *E. coli* transformant was identified by restriction enzyme site mapping that harbored a plasmid that contained the bar gene in the orientation such that Bgl II digestion generated fragments of 4118 and 764 bp. This plasmid was named pDAB 218.

7. pDAB 219: DNA of plasmid pDAB 218 was digested with Bcl I, and the linear fragment of 4882 bp was ligated to a 3133 bp Bgl II fragment prepared from DNA of pKA882-2xBg (see step 10 below). The latter fragment contains the GUS coding region, under the transcriptional control of the 35S promoter, with the Nos Poly A transcription termination signals. An *E. coli* transformant was identified that contained the GUS and PAT coding regions, and restriction enzyme recognition site mapping revealed that both coding regions were encoded by the same DNA strand. This plasmid was named pDAB 219.

8. DNA of plasmid pDAB 219 was used as the template for the polymerase chain reaction (PCR, (Saiki et al., *Science*, 239 (1988) 487)) using as primers the synthetic oligonucleotides: i) CTCGAGATCTAGATATCGATGAATTCCC (SEQ. ID. NO. 69), and ii) TAT <u>GGATCC</u>TGTGATAACC GACATATGCCCCGG<u>TTTCGTTG</u> (SEQ. ID. NO. 70). Primer i) represents nucleotides 419 to 446 of pDAB 219, and includes bases corresponding to the recognition sites of Xho I (CTCGAG), Bgl II (AGATCT), Xba I (TCTAGA), EcoR V (GATATC), Cla I (ATCGAT), and EcoR I (GAATTC). The single underlined bases in Primer ii) represent the recognition sequence of BamH I, and the double underlined bases represent nucleotides 1138 to 1159 of pDAB 219, and correspond to nucleotides 21728 to 21749 of the ORF 25 Poly A fragment (see above). PCR amplification generated a product of 760 bp.

9. pKA882-Bg: pKA882 DNA was digested with Pst I, and the linear fragments were ligated to synthetic adaptors having the sequence CAGATCT GTGCA (SEQ. ID. NO. 71) (Note: When annealed, these molecules form double stranded molecules that have sticky ends compatible with those generated by Pst I. Ligation of such molecules to Pst I digested DNA results in a sequence that is no longer cleaved by Pst I, and introduces a new Bgl II site.). An *E. coli* transformant was identified that harbored a plasmid that was not cleaved by Pst 1, and that had a unique Bgl II site. The plasmid was named pKA882-Bg.

10. pKA882-2xBg: pKA882-Bg DNA was digested with EcoR I, and the linear fragments were ligated to synthetic adaptors having the sequence AATTGAGATCTC (SEQ. ID. NO. 72). Ligation of annealed such molecules to EcoR I digested DNA results in a sequence that is no longer cleaved by EcoR I, and introduces a new Bgl II site. An *E. coli* transformant was identified that harbored a plasmid that was not cleaved by EcoR I, and that generated Bgl II fragments of 3027 and 2658 bp. This plasmid was named pKA882-2xBg.

11. pDAB 305 Bg: Plasmid pDAB305 was digested to completion with EcoR I, and the linearized DNA was ligated to kinased, self-complementary oligonucleotide adapters having the sequence AATTGAGATCTC (SEQ. ID. NO. 73). Ligation of this adapter to the overhanging ends generated by EcoR I recircularized the plasmid DNA, introduced a new Bgl II recognition site, and destroyed the former EcoR I recognition site. The resulting plasmid was named pDAB 305 Bg.

Example 8: Construction of plant transformation vectors containing the bar gene of *Streptomyces hygroscopicus*

The starting material is plasmid pIJ4104 (White et al., *Nucl. Acid Res.* 18 (1990) 1062), which contains the coding region of the bar gene of *S. hygroscopicus*, and was obtained from M. J. Bibb (John Innes Institute, Norwich, United Kingdom). The bar gene encodes the enzyme phosphinothricin acetyl transferase (PAT).

pDAB 219A: DNA of plasmid pDAB 219 was digested with Bgl II, the 7252 bp fragment was purified from an agarose gel, and ligated to the 747 bp fragment generated by digestion of the PCR product of Example 7F Step 8 by Bgl II and BamH I. An *E. coli* transformant was identified that harbored a plasmid that contained a unique Bgl II site positioned at the 3' end of the ORP 25 Poly A fragment. The DNA structure of the 3' end of the PAT coding sequence was confirmed by DNA sequence analysis. This plasmid was named pDAB 219Δ.

The DNA sequence of pDAB 219A is as follows: Beginning with the base following the last A residue of the Xba I site on the lac Z coding strand of pIC20R (Marsh et al., *Gene*, 32 (1984) 481), the linker TCCTGATCTGTGCA GGTCCCC (SEQ. ID. NO. 74), followed by CaMV nucleotides 6605 to 7439, followed by the linker sequence GGG- GACTCTAGAGGATCCGGATCCGTCGAC<u>CATGGTC</u> (SEQ. ID. NO. 75), followed by the rest of the coding region of GUS with 44 bp of 3' flanking *E. coli* genomic DNA (nucleotides 306 to 2152 of Jefferson et al., (*Proc. Natl. Acad. Sci.*, 83 (1986) 8447). The underlined bases represent the codons for the first two amino acids of the GUS protein, the second of which was changed from leucine in the original *E. coli* uid A gene (Jefferson et al., (*Proc. Natl. Acad. Sci.*, 83 (1986) 8447) to valine in pRAJ275 (Jefferson et al., *Plant Molec. Biol, Reporter,* 5 (1987) 387). These bases are followed by the linker sequence GGGGAATTG-GAGAGCTCGAATTTCCCC (SEQ. ID. NO. 76), then by bases 1298 to 1554 of the Nos Poly A sequence (DePicker et al., *J. Molec. Appl. Genet.,* 1 (1982) 5561). The linker sequence GGGAATTGAGATCAGGATCTC-GAGCTCGGG (SEQ. ID. NO. 77) is followed by bases 6495 to 6972 of CaMV, the linker CATCGATG, and CaMV bases 7090 to 7443. These bases are followed by the linker CAAGCTTGGCTGC AGGTC (SEQ. ID. NO. 78), then by bases corresponding to nucleotides 20 to 579 of the bar clone in pIJ4104 (White et al., *Nucl. Acids Res.* 18 (1990) 1062), the linker CTGTGATAACC (SEQ. ID. NO. 79), ORF 25/26 poly A nucleotides 21728 to 22440 (1), the linker GGAAT-TCATCGATATCT AGATCTCGAGCTCGGGGTACCGAGCTCGAATTC (SEQ. ID. NO. 80) and the rest of pIC20R. The Bgl II recognition site (underlined) represents a unique site into which other genes may be introduced.

Figure 7:
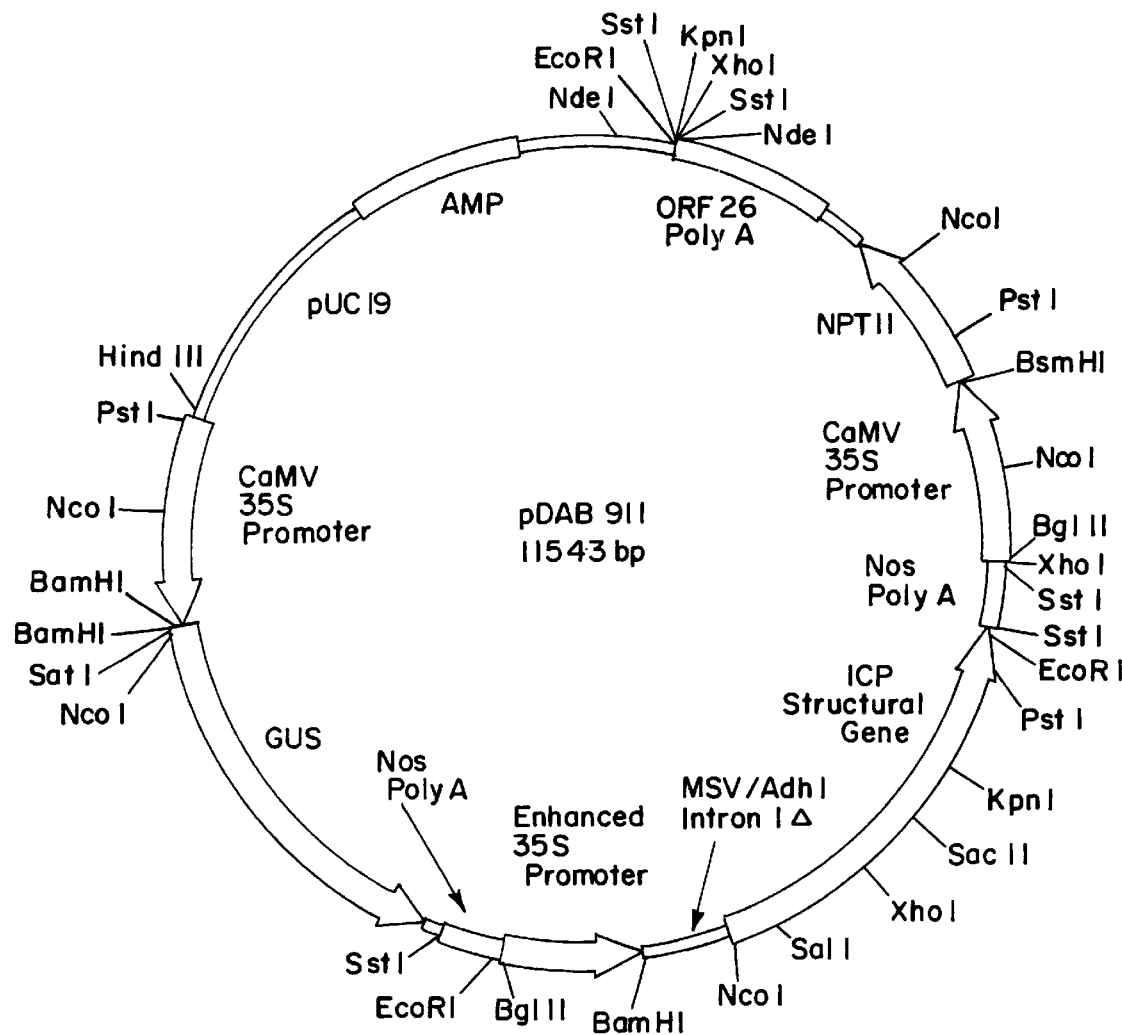
Figure 8:
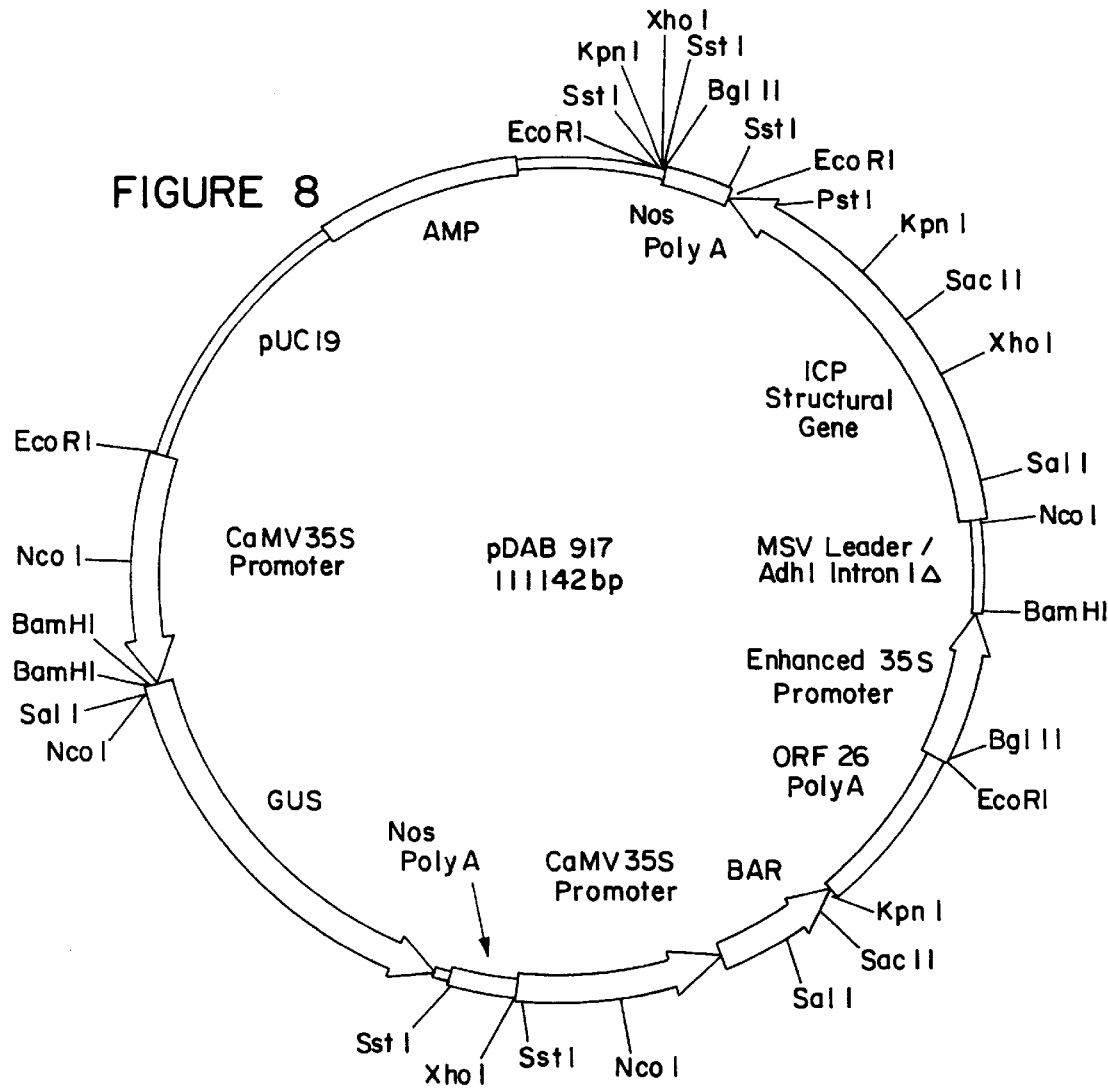

For expression in transgenic plant tissues and plants, the Bt ICP gene was subcloned into three different vectors. First, for cotransformation with plasmids carrying selectable and screenable markers, the ICP gene was cloned in plasmid pDAB305Bg. The BamH I site situated downstream of the ICP gene was modified to a Sst I site by insertion of a BamH I/Sst I adapter. The 1854 base pair Nco I-Sst I fragment carrying the ICP gene was inserted under the control of the high expression doubly enhanced 35S promoter and the nopaline synthase (Nos) poly A addition sequences, resulting in plasmid pDAB910 (FIG. 6). Second, for transformation into MSD culture protoplasts and kanamycin selection, the enhanced 35S/Bt/Nos cassette was subcloned from pDAB910, as a 3150 base pair Bgl II fragment, into the unique Bgl II site of pDAB199, where the preparation of this plasmid is disclosed Sukhapinda et al.(*Plant Cell Reports* 13 (1993) 63), transformation of maize (*Zea maysl*) proplasts and regeneration resulting in plasmid pDAB911 (FIG. 7). Third, the same 35SEn$^2$/Bt/Nos cassette was subcloned into the unique Bgl II site of pDAB219Δ, resulting in plasmid pDAB917 (FIG. 8), for transformation by bombardment of TypeII callus and Basta™ selection.

pDAB 917, which was prepared as indicated above, was deposited at the Agricultural Research Service Culture Collection (NRRL), 1815 North University Street, Peoria, Ill. 61604 on Jul. 21, 1998 and accession number NRRL B-30042.

Example 9: Construction of a Reference Gene Encoding Firefly Luciferase.

Production of the GUS protein from genes controlled by different promoter versions was often compared relative to an internal control gene that produced firefly luciferase (DeWet et al., *Molec. Cell Biol.* 7 (1987) 725). A plasmid (pT3/T7-1 LUC) containing the luciferase (LUC) coding region was purchased from CLONTECH (Palo Alto, Calif.), and the coding region was modified at its 5' and 3' ends by standard methods. Briefly, the sequences surrounding the translational start (ATG) codon were modified to include an Nco I site (CCATGG) and an alanine codon (GCA) at the second position. At the 3' end, an Ssp I recognition site positioned 42 bp downstream of the Stop codon of the luciferase coding region was made blunt ended with T4 DNA polymerase, and ligated to synthetic oligonucleotide linkers encoding the Bgl II recognition sequence. These modifications permit the isolation of the intact luciferase coding region on a 1702 bp fragment following digestion by Nco I and Bgl II. This fragment was used to replace the GUS gene of plasmid pDAB305 (see Example 7E, step 5), such that the luciferase coding region was expressed from the enhanced 35S promoter, resulting in plasmid pDeLux. The 5' untranslated leader of the primary transcript includes the modified MSV leader/Adh intron sequence.

Example 10: Cell Transformation.

Cell suspension cultures derived from immature maize microspores were used as the starting plant materials. These microspore-derived (MSD) cultures were maintained as described by Mitchell et al., *J. Plant Physiol.,* 137 (1991) 530. The cultures are haploid, and some cell lines were capable of regenerating haploid plants. Eight- to 20-month old cell suspension cultures were used for protoplast isolation. The protoplast density was adjusted to $4 \times 10^6$ protoplasts/ml of electroporation solution [20 mg/L $KH_2PO_4$, 115 mg/L $NaH_2PO_4$, 444 mg/L $CaCl_2$, 7.5 g/L NaCl, 36.4 g/L mannitol, pH 7.2 (Fromm et al., *Nature,* 319 (1986) 791]. The protoplast suspension was heat shocked at 42° C. for 5 minutes and then placed on ice. The plasmids pDAB 911 alone or pDAB 910 together with pDAB 326 were used in the protoplast transformation experiments. Equimolar DNA amounts of the plasmids (e.g. 64 μg of pDAB 911, 31.6 μg of pDAB 910 and 46 μg of pDAB 326) were used. The plasmid DNA, in 20–40 μl sterile 1.0 mM Tris, pH 8.0, 1.0 mM EDTA, was placed in a one ml polystyrene electroporation cuvette containing a volume of the electroporation solution to make a total volume of 0.5 ml. One-half ml of the protoplast suspension was pipetted into the cuvette immediately before a single electrical pulse (400 μF, 300 v/cm) was applied from an IBI Gene Zapper unit. The cuvette was immediately placed on ice for 10 minutes. A volume of two hundred and fifty μl of the protoplast suspension (ca. $5 \times 10^5$ protoplasts) was spread on a filter (47 mm nylon; Micron Separations, Inc.) which was placed over the feeder cells (300 mg of MSD cells, Line 34) spread over M1 solid medium in a 60×15 mm polystyrene Petri plate. One week after plating, the filter was transferred to a selection medium containing 100 mg/L kanamycin sulfate. After four to six weeks on the kanamycin containing medium, resistant callus isolates could be observed and selected. From a total of four transformation experiments with the mentioned plasmids, over 400 isolates were selected. These callus isolates were grown on the same medium until enough tissue was accumulated for further analysis.

To determine whether these selected isolates were transformed and expressed the introduced marker genes, the callus tissues were assayed for β-glucuronidase (GUS) activity using the histochemical technique described by Jefferson, *Plant Molec. Biol. Rep.,* 5 (1987) 387, and for neomycin phosphotransferase (NPT II) activity using the technique described by Reiss et al., *Gene,* 30 (1984) 211. The selected isolates were tested for expression of the introduced ICP gene by immunoblot analysis as described above. The results are summarized in Table 16.

TABLE 16

Summary of expression of β-glucuronidase (GUS), neomycin phosphotransferase II (NPT II), and Bt insecticidal crystal protein (ICP) genes in transformed MSD calli

| Exp. # | Plasmid(s) | # Selected Isolates | # GUS$^+$/ # Assayed | # NPT II$^+$/ # Assayed | # ICP$^\#$/ # Assayed |
|---|---|---|---|---|---|
| 1/28 | pDAB 911 | 27 | 0/23 | 10/17 | 2/12 |
| 3/3 | pDAB 911 | 117 | 5/117 | 13/21 | 0/20 |
| 3/6 | pDAB 911 | 95 | 0/95 | 1/26 | NA |
|  | pDAB 910 + pDAB 326 | 98 | 30/98 | 8/12 | 2/25 |
| 3/17 | pDAB 911 | 105 | 0/105 | 4/7 | 0/8 |

Figure 9:
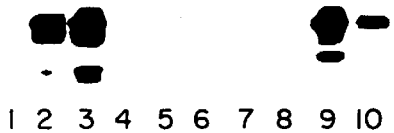
Figure 10:
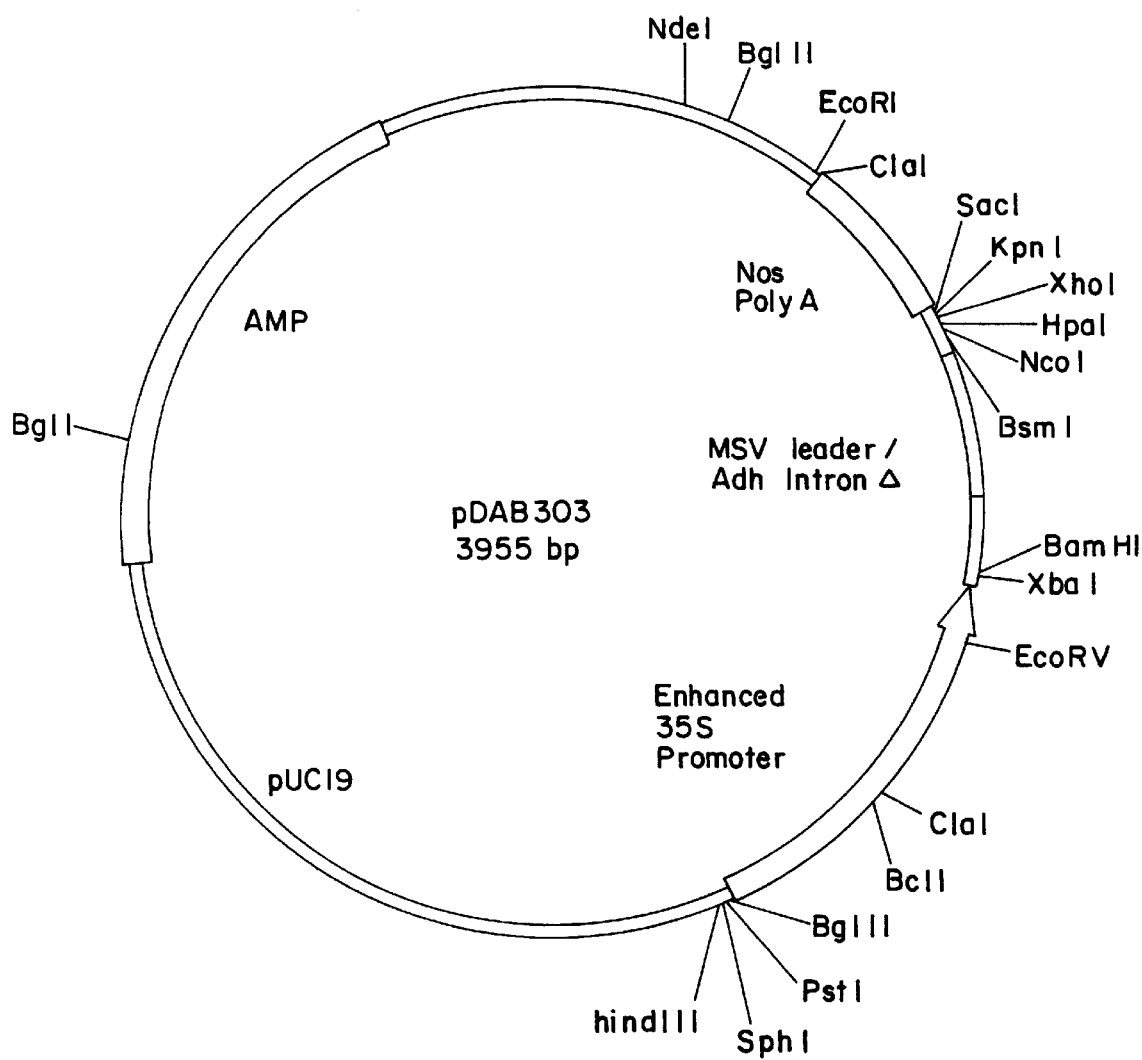
Figure 11:
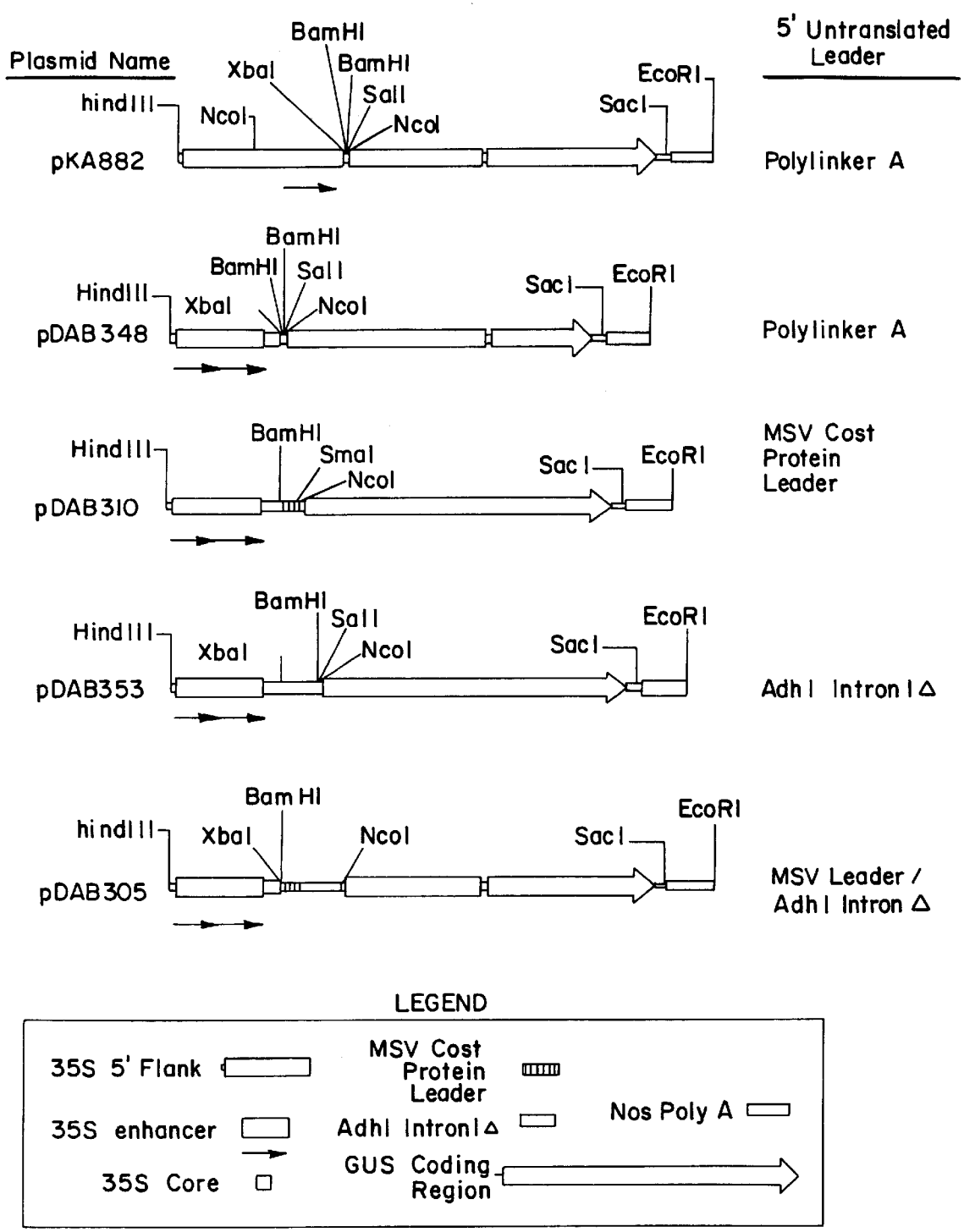

A total of four isolates showed detectable levels of the ICP. Two isolates were transformed with 10 pDAB 911, and their ICP expression level corresponds to approximately 0.1% of the total extractable protein (FIG. 9). The other two isolates, obtained from cotransformation of pDAB 910 and pDAB 326, also expressed ICP at approximately 0.1% of total extractable protein (data not shown). Callus tissue from one isolate (transformed with pDAB 911) was used in a 3-day feeding assay of *Heliothis virescens* neonate larvae. The results (Table 17) indicated that the callus tissue produced sufficient ICP to kill most of the larvae, and severely inhibit the growth of survivors.

TABLE 17

Insecticidal activity of MSD callus, transformed with the ICP gene, in a 3-day *Heliothis virescens* feeding bioassay

| Exp. # | Diet | # Input Larvae | # Dead | Mean Mass of Survivors (mg)[b] | % Killed: (% Growth Inhibition) |
|---|---|---|---|---|---|
| 1 | MSD control | 19 | 0 | 5.0 ± 0.55 | 0: (0) |
| 2 | MSD (ICP) | 20 | 12[a] | 0.26 ± 0.08 | 70; (95) |

[a]3 larvae escaped from the assay and were not counted.
[b]±1 Standard Deviation.

Example 11: Cell Transformation

Part A—Establishment of Embryogenic Callus Cultures

Embryogenic callus cultures were initiated from immature embryos of genotypes specially bred for amenability to in vitro manipulation. Cultures representing two genotypes were used: i) "Backcrossed B73" is a $BC_3$ inbred derived from the cross B73x(B73xA188), and ii) "High II" is a hybrid made by intermating two S3 lines derived from a B73xA188 cross. When exposed to appropriate cultural conditions, immature embryos from both of these genotypes display consistently high levels of callus formation capable of fertile plant regeneration.

Seeds of the two $S_3$ parents of "High II" and B73 were sown individually in pots containing approximately 4 kg of dry soil mix #3 (Conrad Fafard, Inc., Springfield, Mass.) moistened and adjusted to pH 6.0. The plants were maintained in a greenhouse under a 16/8 photoperiod. Ambient daylight was supplemented with a combination of high pressure sodium and metal halide lamps such that the minimum light intensity 2 m above pot level was approximately 1,500 ft-candles. Greenhouse temperature was maintained within 3° C. of 28° C. during the day and 22° C at night. The plants were irrigated as needed with a solution containing 400 mg/L of 20-20-20 fertilizer (W. R. Grace & Co., Fogelsville, Pa.), plus 8 mg/L chelated iron (CIBA-GEIGY, Greensboro, N.C.).

Pollen shed and silk emergence began 50–60 days after planting. Female plants were prepared for pollination on the day before pollen availability by cutting off the tip of the husks and silks of unfertilized ear shoots. The next day, after the silks had grown to form a thick "brush" all the same length, pollen was collected by placing paper bags over the tassels and carefully applied to the silks. "Backcrossed B73" embryos were produced on B73 μplants by pollinating with plants regenerated from $BC_2$ cultures (as described below). "High II" embryos resulted from intermating the $S_3$ lines.

When the developing embryos reached a length of approximately 1.5–2.0 mm (10–14 days after pollination), the ear was excised and surface sterilized by emersion in 70% v/v ethanol for 10 minutes followed by soaking in 20% v/v commercial bleach (1% sodium hypochlorite) for 30 minutes. Following a sterile, distilled water rinse, immature embryos were aseptically isolated and placed onto an "initiation" medium with the embryo axis in contact with the medium (scutellar-side away from the medium). The "initiation" medium consisted of the following components: N6 basal salts and vitamins (Chu, *Proc. Symp. Plant Tissue Culture*, (1978), Peking Press, pp. 43–56), 20 g/L sucrose, 2.9 g/L proline, 100 mg/l casein hydrolysate, 1 mg/l 2,4-dichloro-phenoxyacetic acid (2,4-D), 10 mg/L $AgNO_3$ and 2.5 g/L gelrite (Kelco, Inc., San Diego, Calif.) adjusted to pH 5.8.

The immature embryos were incubated at 28° C. in the dark for 10–30 days during which time callus tissue, displaying various types of morphology, proliferated from the scutellar region. The callus tissue produced during this time was classified into three distinct types: i) soft, granular, translucent callus lacking any apparent morphological organization (known as nonembrogenic), ii) compact, nodular, yellowish-to-white callus consisting of groups of somatic embryos (often fused) with distinct scutellar- and coleoptile-like structures (known as Type I), and iii) soft callus with numerous globular and elongated somatic embryos on suspensor-like structures (known as Type II). Type II callus was the most suitable for establishing friable, embryogenic cultures. Sometimes entire scutella proliferated with this type of tissue or at times only small sectors exhibiting this morphology developed. Selective subculture was then performed, whereby only tissue with well-defined globular and elongated somatic embryos along with some subtending undifferentiated, soft tissue was transferred to fresh "initiation" medium. After 2–3 subcultures on "initiation" medium, callus was transferred to "maintenance" medium. The "Maintenance" medium differed from the "initiation" medium in that it contained 690 mg/L proline and no $AgNO_3$. After 8–16 weeks of preferential enrichment for Type II callus, well-established, embryogenic cultures were ready for helium blasting.

Part B—Transformation via Helium Blasting

Helium blasting involved accelerating micron-size particles, coated with plasmid DNA, to penetrating velocities. The device used was described in U.S. Pat. No. 5,141,131. Briefly, the device consisted of a high pressure helium source, a reservoir of DNA-coated gold microparticles in suspension, and a multipurpose valve which provided selective communication between the outlet of the helium source and the inlet of the gold suspension. The gold particles were coated with plasmid DNA (pDAB917) containing coding sequences for selectable and screenable marker genes.

The selectable marker gene was bar which encodes for the enzyme phosphinothricin acetyltransferase (PAT) and confers resistance to the herbicide Basta™. The screenable marker gene was uidA which encodes for β-glucuronidase (GUS), the activity of which was monitored histochemically. Both genes were driven by the 35S constitutive promoter from Cauliflower Mosaic Virus. In this way, rare transformed cells were selected out of a background of non-transformed tissue by exposure to the herbicide Basta™ and tested for the presence of β-glucuronidase activity using a histochemical assay which turned positive tissue blue.

Plasmid DNA was adsorbed onto the surface of gold particles prior to use in transformation experiments. The gold particles were spherical with diameters ranging from about 1.5–3.0 microns (Aldrich Chemical Co., Milwaukee, Wis.). Adsorption was accomplished by adding 74 uL of 2.5 M calcium chloride and 30 uL of 0.1 M spermidine to 300 uL of DNA/gold suspension (140 ug pDAB917, 0.01 M Tris buffer, and 1 mM EDTA). The DNA-coated gold particles were vortexed immediately, then allowed to settle to the bottom of an Eppendorf tube and the resultant clear liquid was completely drawn off. The DNA-coated gold particles were then resuspended in 1 mL of 100% ethanol. The suspension was then diluted to 15 mg DNA/gold per mL of ethanol for use in helium blasting experiments.

Approximately 250 mg of embryogenic callus tissue, 5–7 days following subculture, was arranged in a thin circular layer directly on the surface of "maintenance" medium. The tissue was allowed to dry out slightly by allowing the plates to stand uncovered in a laminar flow hood for several minutes before use. In preparation for helium blasting, the callus was covered with a 104 micron stainless steel screen. The DNA-coated gold particles were then accelerated at the callus tissue. Each callus tissue sample was blasted 10–15 times with each blast delivering approximately 1 uL of DNA-coated gold suspension.

Part C—Selection of Transgenic Tissue and Plant Regeneration

After blasting, callus tissue was allowed to incubate for 1–2 days under the conditions described previously. Each tissue sample was then divided into approximately 60 equal pieces (1–3 mm diameter) and transferred to fresh "maintenance" medium containing 30 mg/L Basta™. Every three weeks, callus tissue was non-selectively transferred (with no regard for tissue morphology) to fresh Basta™-containing "maintenance" medium. At this concentration of herbicide, very little growth occurred. After 8–16 weeks, sectors proliferating from a background of growth inhibited tissue were apparent. This tissue was isolated from the other callus and maintained separately on Basta™-containing "maintenance" medium and selectively subcultured (only Type II tissue) every 10–14 days. At this point, a histochemical assay for GUS expression was performed as described below.

All Basta™-resistant callus (whether GUS positive or GUS negative) was selectively subcultured to "induction" medium and incubated at 28° C. in low light (125 ft-candles) for one week followed by one week in high light (325 ft-candles) provided by cool fluorescent lamps. The "induction" medium was composed of MS salts and vitamins (Murashige et al., *Physiol. Plant*, 15 (1962) 473–497) 30 g/L sucrose, 100 mg/L myo-inositol, 5 mg/L benzyl-amino purine, 0.025 mg/L 2,4-D, 2.5 g/L gelrite adjusted to pH 5.7. Following this two-week induction period, the callus was then non-selectively transferred to "regeneration" medium and incubated in high light at 28° C.

The "regeneration" medium was composed of MS salts and vitamins, 30 g/L sucrose, and 2.5 g/L gelrite adjusted to pH 5.7. Every 14–21 days the callus was subcultured to fresh "regeneration" medium selecting for tissue which appeared to be differentiating leaves and roots. Both "induction" and "regeneration" media contained 30 mg/L Basta™. Plantlets were transferred to 10 cm pots containing approximately 0.1 kg of dry soil mix, and were then moistened thoroughly and covered with clear plastic cups for approximately 4 days. At the 3–5 leaf stage, plants were transplanted to larger pots and grown to maturity as previously described. Self- or sibling-pollinations were performed on plants regenerated from the same culture or crossed to non-transformed seed-derived plants in order to obtain transgenic progenies.

Example 12: Field Trials

Using the procedures and transgenic progeny described in Example 11, four (4) transgenic inbreds were prepared using conventional breeding techniques. The resulting inbreds were used to develop four transgenic hybrids.

Seed from each of four (4) transgenic hybrids were planted in single row plots using a randomized complete block design. Locations included research stations in Indiana, Illinois, Minnesota, and Iowa. Control plots (non-transgenic control hybrids) were used to measure the amount of insect damage due to natural (Control A) and artificial infestations (Control B). Control of second generation European Corn Bore (ECB) was evaluated at all locations. First generation ECB and corn earworm were evaluated only at the Indiana and Illinois field research stations. All insects were obtained from a single source. Each trial was infested twice (4–6 days apart) with neonate larvae. For first generation ECB studies, 40–80 larvae were applied to plants at the mid-whorl development stage, while the same number of larvae were applied at mid-silk stage in second generation ECB studies. Damage to plants was determined 6 weeks later by splitting stalks and ear shoots when present. Number of ECB larvae and tunnels were recorded for each of 10 μplants per replicate. Studies on corn earworm required 10 μplants per replicate to be artificially infested with first instar larvae of corn earworm at about 5–10 per ear. Approximately 3 weeks later, ears were evaluated for the number of larvae present.

A combined analysis of variance was conducted on data collected for first generation ECB studies (Table 18). Artificially infested controls averaged one tunnel per stalk and had a level of infestation over 70 percent. Transgenic lines showed little to no ECB tunneling ($\leq 0.06$ tunnels per stalk) and had levels of infestation below 7 percent. A significant difference ($p<0.05$) was shown between controls and transgenic lines for larvae and tunnels per stalk as well as the percentage of infested plants. No statistical differences were found between the individual transgenic hybrids for control of first generation ECB.

TABLE 18

| | First Generation ECB Data | | | | |
|---|---|---|---|---|---|
| | Stalk | | | Ear | |
| | Number of Larvae | Number of Tunnels | % Stalk Infested | Number of Larvae | Number of Tunnels |
| INDIANA | | | | | |
| Control A | 0.05 | 0.33 | 25.0 | n/a | n/a |
| Control B | 0.25 | 1.23 | 72.5 | n/a | n/a |
| Hybrid 1 | 0.00 | 0.00 | 0.0 | n/a | n/a |
| Hybrid 2 | 0.00 | 0.00 | 0.0 | n/a | n/a |
| Hybrid 3 | 0.00 | 0.00 | 0.0 | n/a | n/a |
| Hybrid 4 | 0.00 | 0.03 | 2.5 | n/a | n/a |
| ILLINOIS | | | | | |
| Control A | 0.20 | 0.30 | 27.5 | 0.08 | 0.05 |
| Control B | 0.54 | 1.06 | 74.8 | 0.21 | 0.13 |
| Hybrid 1 | 0.00 | 0.00 | 0.0 | 0.00 | 0.00 |
| Hybrid 2 | 0.00 | 0.03 | 2.5 | 0.00 | 0.00 |
| Hybrid 3 | 0.00 | 0.13 | 12.5 | 0.00 | 0.00 |
| Hybrid 4 | 0.00 | 0.00 | 0.0 | 0.00 | 0.00 |
| Combined Analysis | | | | | |
| Control A | 0.13 | 0.31 | 26.3 | | |
| Control B | 0.40 | 1.14 | 73.6 | | |
| Hybrid 1 | n/a | n/a | n/a | | |
| Hybrid 2 | 0.00 | 0.01 | 1.3 | | |
| Hybrid 3 | 0.00 | 0.06 | 6.3 | | |
| Hybrid 4 | 0.00 | 0.01 | 1.3 | | |

For second generation ECB, artificially infested controls averaged between 1 to 3 tunnels per stalk; levels of infestation ranged from 72 to 100 percent (Table 19). Damage to transgenic hybrids ranged from none to slight ($\leq 0.25$ tunnels per stalk) with levels of infestation that ranged from 0 to 23 percent (Table 19). Measurements made on tunnel length showed that tunnels found in the transgenic lines were significantly smaller (p<0.5) compared to the controls (Table 19) Only mean and standard error of the mean were calculated for average tunnel length measurement; other statistical analyses were invalid because the lack of tunnels in the many replicates of the transgenics resulted in missing data. With the exception of the study in Minnesota, these data show that average tunnel length among transgenic hybrids were similar and smaller than the controls. Transgenic lines had significantly less damaged ears from ECB (p<0.05) than the controls. In general, significant differences (p<0.05) were found between controls and the transgenic lines. No statistically significant differences were detected between individual transgenic hybrids and their level of control to second generation ECB.

Artificially infested controls averaged approximately one earworm larvae per ear and a range of infestation between 40 and 90 percent. Transgenic hybrids were significantly different (p<0.05) from controls for both earworm per ear and percent plants infested. Although no statistically significant difference between transgenic hybrids was detected, hybrid #1 showed damage from earworm at both locations (Table 20). Hybrids 2, 3 and 4 showed little to no damage from the insect.

TABLE 20

Corn Earworm Data

|  | # of Earworm | % Infested | # of ECB | % Infested |
|---|---|---|---|---|
| INDIANA |  |  |  |  |
| Control A | 0.15 | 15.0 | n/a | n/a |
| Control B | 1.18 | 80.0 | n/a | n/a |
| Hybrid 1 | 0.05 | 5.0 | n/a | n/a |
| Hybrid 2 | 0.00 | 0.0 | n/a | n/a |

TABLE 19

Second Generation ECB Data

|  | Ear | | Stalk | | Total | | Average Tunnel Length* | |
|---|---|---|---|---|---|---|---|---|
|  | # of Larvae | # of Tunnels | # of Larvae | # of Tunnels | Tunnel Length | % Stalks Infested | Mean | S.E. of Mean |
| INDIANA |  |  |  |  |  |  |  |  |
| Control A | 0.18 | 0.10 | 0.28 | 0.35 | 1.05 | 47.5 | 2.92 | ±0.61 |
| Control B | 0.71 | 0.77 | 1.24 | 1.59 | 3.78 | 94.8 | 2.38 | ±0.20 |
| Hybrid 1 | 0.03 | 0.00 | 0.00 | 0.00 | 0.00 | 2.5 | n/a | n/a |
| Hybrid 2 | 0.00 | 0.00 | 0.00 | 0.00 | 0.00 | 0.0 | n/a | n/a |
| Hybrid 3 | 0.00 | 0.00 | 0.03 | 0.03 | 0.03 | 2.5 | 1.00 | n/a |
| Hybrid 4 | 0.00 | 0.00 | 0.00 | 0.00 | 0.00 | 0.0 | n/a | n/a |
| ILLINOIS |  |  |  |  |  |  |  |  |
| Control A | 0.45 | 0.60 | 1.60 | 1.83 | 9.21 | 85.0 | 5.85 | ±0.84 |
| Control B | 0.58 | 0.68 | 2.20 | 2.55 | 11.11 | 100.0 | 4.38 | ±0.39 |
| Hybrid 1 | 0.03 | 0.03 | 0.00 | 0.05 | 0.13 | 5.0 | 2.50 | n/a |
| Hybrid 2 | 0.00 | 0.00 | 0.00 | 0.08 | 0.19 | 5.0 | 2.53 | ±0.02 |
| Hybrid 3 | 0.00 | 0.00 | 0.00 | 0.13 | 0.32 | 10.0 | 2.52 | ±0.01 |
| Hybrid 4 | 0.00 | 0.00 | 0.00 | 0.08 | 0.19 | 7.5 | 2.50 | ±0.00 |
| IOWA |  |  |  |  |  |  |  |  |
| Control A | 0.13 | 0.23 | 0.68 | 1.80 | 3.35 | 82.5 | 2.06 | ±0.15 |
| Control B | 0.15 | 0.25 | 0.73 | 1.90 | 4.85 | 95.0 | 2.37 | ±0.23 |
| Hybrid 1 | 0.00 | 0.03 | 0.03 | 0.25 | 0.42 | 22.5 | 1.58 | ±0.35 |
| Hybrid 2 | 0.00 | 0.00 | 0.00 | 0.13 | 0.18 | 10.0 | 1.38 | ±0.43 |
| Hybrid 3 | 0.00 | 0.00 | 0.00 | 0.13 | 0.10 | 12.5 | 0.80 | ±0.12 |
| Hybrid 4 | 0.00 | 0.00 | 0.00 | 0.13 | 0.10 | 12.5 | 0.80 | ±0.12 |
| MINNESOTA |  |  |  |  |  |  |  |  |
| Control A | 0.00 | 0.05 | 0.40 | 0.68 | 1.79 | 47.5 | 2.63 | ±0.58 |
| Control B | 0.03 | 0.16 | 0.67 | 1.43 | 3.39 | 71.8 | 2.61 | ±0.38 |
| Hybrid 1 | 0.00 | 0.00 | 0.03 | 0.03 | 0.08 | 2.5 | 3.00 | n/a |
| Hybrid 2 | 0.00 | 0.00 | 0.00 | 0.03 | 0.04 | 2.5 | 1.50 | n/a |
| Hybrid 3 | 0.00 | 0.00 | 0.00 | 0.03 | 0.01 | 2.5 | 0.50 | n/a |
| Hybrid 4 | 0.00 | 0.00 | 0.03 | 0.05 | 0.15 | 5.0 | 3.00 | ±1.00 |
| Combined Analyses |  |  |  |  |  |  |  |  |
| Control A | 0.19 | 0.24 | 0.74 | 1.16 | 3.85 | 65.6 |  |  |
| Control b | 0.37 | 0.46 | 1.21 | 1.87 | 5.78 | 90.4 |  |  |
| Hybrid 1 | 0.01 | 0.01 | 0.01 | 0.08 | 0.16 | 8.1 |  |  |
| Hybrid 2 | 0.00 | 0.00 | 0.00 | 0.06 | 0.10 | 4.4 |  |  |
| Hybrid 3 | 0.00 | 0.00 | 0.01 | 0.08 | 0.11 | 6.9 |  |  |
| Hybrid 4 | 0.00 | 0.00 | 0.01 | 0.06 | 0.11 | 6.3 |  |  |

TABLE 20-continued

Corn Earworm Data

| | # of Earworm | % Infested | # of ECB | % Infested |
|---|---|---|---|---|
| Hybrid 3 | 0.00 | 0.0 | n/a | n/a |
| Hybrid 4 | 0.00 | 0.0 | n/a | n/a |
| ILLINOIS | | | | |
| Control A | 0.23 | 17.5 | 0.28 | 25.0 |
| Control B | 1.12 | 58.0 | 0.27 | 23.8 |
| Hybrid 1 | 0.28 | 27.5 | 0.03 | 2.5 |
| Hybrid 2 | 0.03 | 2.5 | 0.00 | 0.0 |
| Hybrid 3 | 0.00 | 0.0 | 0.00 | 0.0 |
| Hybrid 4 | 0.00 | 0.0 | 0.00 | 0.0 |
| Combined Analysis | | | | |
| Control A | 0.19 | 16.3 | | |
| Control B | 1.15 | 69.0 | | |
| Hybrid 1 | 0.16 | 16.3 | | |
| Hybrid 2 | 0.01 | 1.3 | | |
| Hybrid 3 | 0.00 | 0.0 | | |
| Hybrid 4 | 0.00 | 0.0 | | |

Numerous modifications and variations in practice of the invention are expected to occur to those skilled in the art upon consideration of the foregoing detailed description of the invention. Consequently, such modifications and variations are intended to be included within the scope of the following claims.

Example 13: Determination of Relative Promoter Strengths by Transient Expression in Electroporated Protoplasts Black Mexican Sweet (BMS) cultures (V. Walbot, Stanford University) were maintained as suspensions in liquid medium (Fromm et al., *PNAS USA* 82 (1985) 351).

Protoplasts were isolated from 4-day old cultures by 30 suspending the cells in 4X volumes of protoplast isolation solution (Fromm et al., *Enzymol.* 153 (1987) 351) containing 0.5% cellulase Onozuka RS, 0.5% hemicellulase, 0.02% pectinase (Karlan Research Products, Santa Rosa, Calif.), followed by gentle shaking. After 3.5 hr digestion, cells and protoplasts were collected by centrifugation, (208×g, 25° C., 5 min), and washed twice by gentle resuspension in protoplast isolation solution. Purification of protoplasts was achieved by flotation on Maize Wash Solution (Shanin, *Theor. Appl. Genet.* 69 (1985) 235). Protoplasts were washed twice in electroporation solution (Fromm et al., *Enzymol.* 153 (1987) 351), and brought to a final density of $4 \times 10^6$ protoplasts/ml. Prior to electroporation, the protoplasts were heat shocked for 5 min at 42° C., then placed on ice until use. Aliquots of about $2 \times 10^6$ protoplasts were electroporated with the appropriate DNA mixture in a 1 ml volume. Typically DNA mixtures contained (per $2 \times 10^6$ protoplasts in 1 ml), 60 ug of test plasmid DNA and 4.5 ug of reference plasmid DNA. Electroporation conditions were: 1500 uF, 200–400 V across a 1 cm gap, pulse time of 25 msec (Promega Model 240/250, Madison, Wis.). Following electroporation, the protoplasts were placed on ice for 10 min, then plated into plastic Petri dishes (previously coated with a thin layer of 1.2% SeaPlaque agarose; FMS BioProducts, Rockland, Me.) containing protoplast growth medium (Fromm et al., *PNAS USA* 82 (1985) 351) at a density of $2.5 \times 10^5$ protoplasts/ml.

Fluorometric assays for GUS activity using 4-methyl-umbelliferyl-glucuronide as a substrate were essentially as described by Jefferson (*Plant Molec. Biol. Reporter* 5 (1987) 387), and assays for luciferase activity using luciferin as substrate were based on the methods of DeWet et al. (*Molec. Cell. Biol.* 7 (1987) 725), Ow et al. (*Science* 234 (1986) 856), Ow et al. (*PNAS USA* 84 (1987) 4870), and Howell et al., (*Plant Molecular Biology Manual* (1989) Ch. B8,1). In some cases the GUS and LUC genes were coelectroporated on separate plasmids, in others they were introduced on a single plasmid. The results of comparative promoter strength studies are given below.

TABLE 21

| Plasmid | Promoter | 5' UTL* | Relative Strength |
|---|---|---|---|
| pKA882 | 35S | Linker A | 1 |
| pDAB348 | En 35S | Linker A | 0.8 |
| pDAB310 | En 35S | MSV CPL | 0.1 |
| pDAB353 | En 35S | Adh1.S intron1Δ | 5.8 |
| PDAB305 | En 35S | MSV CPL + Adh1.S intron1Δ | 42 |

*UTL = Untranslated Leader Sequence

These data demonstrate that no expression advantage is gained by duplication of the 35S enhancer element in maize protoplasts, nor does the MSV coat protein leader sequence confer a translational enhancement by itself. Some expression enhancement is seen when the deleted version of the maize Adh1.S intron 1 is positioned within the 5' untranslated leader. However, an approximately 40-fold increase in GUS expression over the native 35S promoter is observed when the enhanced 35S promoter is coupled to the MSV leader containing the deleted -version of the Adh1.S intron 1. The sequence of the promoter/leader combination is listed as SEQ. ID. NO. 43.

Example 14: Cloning of Intron 6

This example describes the cloning of intron 6 of the maize Adh1.S gene and its incorporation into the synthetic 5' untranslated leader sequence derived from the Maize Streak Virus coat protein gene (MSV/CPL, see above).

The starting material is plasmid pB428, obtained from J. Bennetson, Purdue University. This is a clone if ab 11.5 kbp BamH I fragment of maize genomic DNA inserted into the BamH I site of pBR322, and containing the Adh1.S gene (Dennis et al., *Nucl. Acids Res.* 12 (1984) 3983). A 396 bp fragment containing the intron 6 sequence and parts of flanking exons 6 and 7 was amplified from 10 ng of pB428 template DNA using 100 pmol each of forward primers having the sequence CGACC TGATCACCCCAGCAGATTCGAAGAAGG (SEQ. ID. NO. 81), and reverse primers of sequence TTCAG TGGATCCGAACTTCCTAGCTGAAAAATGGG (SEQ. ID. NO. 82). These primers contain the recognition sequences for Bcl I (TGATCA, underlined in forward primer), and BamH I, (GGATCC, underlined in reverse primers). They are designed to introduce the Bc I site immediately before nucleotide 2162, and the BamH I site immediately following nucleotide 2534, of the Adh1.S sequence of Dennis et al. (*Nucl. Acids Res.* 12 (1984) 3983). The resulting PCR fragment, of expected size 396 bp, contains 20 bases of Adh1.S exon 6, all of intron 6, and 11 bases of exon 7, as presented in (SEQ. ID. NO. 83) Reactions (100 ul final volume) contained, besides template and primers, 1×PCR reaction buffer (as described in Example 2), 0.2 mM final concentration of dATP, dTTP, dGTP, and dCTP, and 5 units of Taq DNA polymerase (Perkin Elmer/Cetus). Temperature cycles were: 94° (1 min; 25 cycles of 940 (I min), 55° (30 sec), 72° (30 sec), followed by an extension period of 72°, 10 min. Appropriate-sized fragments were extracted from an agarose gel, digested with restriction enzymes Bcl I and BamH I, and ligated into Bgl II-digested DNA of pCPL-Bg (see above). A plasmid was identified that had an appropriate restriction enzyme map, and was named pCPL-Adh6.

The structure of pCPL-Adh6 is as follows (vector sequences of pBSK are not included, see Example 7C step 1): the linker sequence GGATCCAG that includes a BamH I recognition site, nucleotides 167 to 186 of MSV, nucleotides 188 to 277 of MSV, the linker sequence GATCA, nucleotides 2162 to 2534 of maize Adh1.S, the linker sequence GGATCTG, and finally nucleotides 278 to 317 of MSV, including an Nco I recognition sequence (SEQ. ID. NO. 84). In analogy to pCPL AlIIΔ (see Example 7D step 3) the MSV leader/intron sequences can be obtained from this plasmid by digestion with BamH I and Nco I, and purification of the 541 bp fragment. This fragment is therefore the functional equivalent of the analogous fragment containing the Adh1.S intron 1 fragment utilized in palsmids described in Examples 7 and 13.

The nucleotide sequence coding for an insecticial protein from Et having the nucleotide SEQ. ID. NO. 1 and amino acid SEQ. ID. NO. 2 is shown in Table 22.

TABLE 22

| | | | | | | | | | | | | | | | | | SEQ. ID. NO. 1 and 2 |
|---|---|---|---|---|---|---|---|---|---|---|---|---|---|---|---|---|---|
| 1<br>1 ▲ | ATG<br>Met | GAC<br>Asp | AAC<br>Asn | AAC<br>Asn | CCA<br>Pro | ATC<br>Ile | AAC<br>Asn | GAG<br>Glu | TGC<br>Cys | ATC<br>Ile | CCT<br>Pro | TAC<br>Tyr | AAC<br>Asn | TTG<br>Leu | AGC<br>Ser | AAC<br>Asn | CCT GAG GTG GAG CTT GGT GAG CGC ATT GAG<br>Pro Glu Val Glu Leu Gly Glu Arg Ile Glu |
| 91<br>31 ▲ | ACC<br>Thr | GGC<br>Gly | TAC<br>Tyr | ACC<br>Thr | CCA<br>Pro | ATC<br>Ile | GAC<br>Asp | ATC<br>Ile | TCT<br>Ser | CTG<br>Leu | TTC<br>Phe | CTG<br>Leu | TCT<br>Ser | CTG<br>Leu | TTC<br>Phe | CTG<br>Leu | TCT<br>Ser | GAG TTC GTG GGT GCT CTT GGT CTG<br>Glu Phe Val Gly Ala Gly Phe Leu Gly Leu |
|  | SalI | | | | | | | | | | | | | | | | | |
| 181<br>61 ▲ | GTC<br>Val | GAC<br>Asp | ATC<br>Ile | ATC<br>Ile | TGG<br>Trp | GGC<br>Gly | ATC<br>Ile | TTC<br>Phe | GGC<br>Gly | CCA<br>Pro | AGC<br>Ser | CAA<br>Gln | ATC<br>Ile | TTC<br>Phe | CTT<br>Leu | GTG<br>Val | CAA<br>Gln | ATC AAC CTC ATC AAC GAG ATT GAG GAG<br>Ile Asn Leu Ile Asn Gln Arg Ile Glu Glu |
| 271<br>91 ▲ | TTC<br>Phe | GCT<br>Ala | CGC<br>Arg | AAC<br>Asn | CAA<br>Gln | GCC<br>Ala | ATC<br>Ile | TCC<br>Ser | AGG<br>Arg | CTT<br>Leu | GAG<br>Glu | CTT<br>Leu | GGT<br>Gly | CAA<br>Gln | ATC<br>Ile | TAC<br>Tyr | AGC<br>Ser | TTG GAG TGG CTG GAG GCT GAC<br>Phe Ala Glu Trp Glu Ala Asp |
| 361<br>121 ▲ | CCA<br>Pro | ACC<br>Thr | AAC<br>Asn | TTG<br>Leu | AGG<br>Arg | GAG<br>Glu | ATG<br>Met | GAG<br>Glu | CGC<br>Arg | ATC<br>Ile | TCT<br>Ser | AAC<br>Asn | ATG<br>Met | GCT<br>Ala | CTG<br>Leu | CTG<br>Leu | ACC<br>Thr | GCC ATC CCT CTG TTC GCT GTG<br>Ala Ile Pro Leu Phe Ala Val |
| 451<br>151 ▲ | CAG<br>Gln | AAC<br>Asn | TAC<br>Tyr | CAA<br>Gln | GTG<br>Val | CCT<br>Pro | CTT<br>Leu | CTG<br>Leu | AGC<br>Ser | GTC<br>Val | TAC<br>Tyr | GTC<br>Val | CAA<br>Gln | GCT<br>Ala | CAC<br>Ala | AAC<br>Asn | CTG<br>Leu | GTG TCT TTC GTG TGG CAA<br>Val Ser Phe Val Gly Gln |
| 541<br>181 ▲ | CGC<br>Arg | TGG<br>Trp | GGC<br>Gly | TTC<br>Phe | GAT<br>Asp | GCT<br>Ala | GCC<br>Ala | ATC<br>Ile | AAC<br>Asn | TCT<br>Ser | CGC<br>Arg | ACC<br>Thr | CTG<br>Leu | ATT<br>Ile | GGC<br>Gly | CTG<br>Leu | TAC<br>Tyr | GAC TAC GCT GTG CGC TGG<br>Asp Tyr Ala Val Arg Trp |
|  | XhoI | | | | | | | | | | | | | | | | | |
| 631<br>211 ▲ | TAC<br>Tyr | AAC<br>Asn | ACG<br>Thr | GGC<br>Gly | CTC<br>Leu | GAG<br>Glu | AGG<br>Arg | GTG<br>Val | TGG<br>Trp | GGT<br>Gly | CCA<br>Pro | GAC<br>Asp | TCC<br>Ser | AGG<br>Arg | GAG<br>Glu | GTG<br>Val | TAC<br>Tyr | CGC AGG GAG CTG ACC GTG<br>Arg Arg Glu Leu Thr Val |
| 721<br>241 ▲ | CTT<br>Leu | GAC<br>Asp | ATT<br>Ile | GTG<br>Val | GCT<br>Ala | CTG<br>Leu | TTC<br>Phe | CCA<br>Pro | AAC<br>Asn | TAC<br>Tyr | GAC<br>Asp | TCC<br>Ser | CGT<br>Arg | ATC<br>Ile | CGC<br>Arg | ACG<br>Thr | GTG<br>Val | TCT CAG ATT TAC ACC AAC<br>Ser Gln Ile Tyr Thr Asn |
| 811<br>271 ▲ | CCA<br>Pro | GTT<br>Val | TTG<br>Leu | GAG<br>Glu | AAC<br>Asn | TTC<br>Phe | GAT<br>Asp | GGC<br>Gly | TCC<br>Ser | TTC<br>Phe | AGG<br>Arg | GGC<br>Gly | TCT<br>Ser | GCT<br>Ala | CAA<br>Gln | ATT<br>Ile | GGC<br>Gly | CGC ATG CTG CAC CCT ATT CTT<br>Arg Met Leu His Pro Ile Leu |
| 901<br>301 ▲ | AAC<br>Asn | AGC<br>Ser | ATC<br>Ile | ACT<br>Thr | ATC<br>Ile | TAC<br>Tyr | ACG<br>Thr | GAC<br>Asp | GCT<br>Ala | CAC<br>His | CGC<br>Arg | ATG<br>Met | TGG<br>Trp | TCT<br>Ser | CAC<br>His | CAA<br>Gln | CAG<br>Gln | CAA GGT TCT TCT GGC<br>Gly His Gly Pro Val Gly Phe Ser Gly |
| 991<br>331 ▲ | CCA<br>Pro | GAG<br>Glu | TTC<br>Phe | ACC<br>Thr | TTG<br>Leu | CCT<br>Pro | ACG<br>Thr | TTG<br>Leu | ACG<br>Thr | GGC<br>Gly | ATG<br>Met | GCT<br>Ala | CTG<br>Leu | GCT<br>Ala | CGC<br>Arg | ATT<br>Ile | GCT<br>Ala | GTG CAA CTG GGC CAA GGT TAC CGC<br>Val Ala Gln Leu Gly Gln Gly Val Tyr Arg |
| 1081<br>361 ▲ | ACC<br>Thr | CTT<br>Leu | TCC<br>Ser | AGC<br>Ser | ACC<br>Thr | TTG<br>Leu | TAC<br>Tyr | CGC<br>Arg | CGC<br>Arg | CCA<br>Pro | ATC<br>Ile | AAC<br>Asn | ATT<br>Ile | GGC<br>Gly | CAG<br>Gln | AAC<br>Asn | CAA<br>Gln | CAG CTT GTG TCT CTT GGT GAC CTT GAG TAC GCT TAC<br>Gln Leu Val Ser Leu Ser Leu Gly Asp Leu Glu Tyr Ala Tyr |

TABLE 22-continued

```
                                                            KpaI
1171  GGC ACC TCT AGC AAC TTG CCA AGC GCT GTG TAC CGC AAG TCT GGT ACC GTG GAC AGC TTG GAC AGC ATC CCT CCA CAG AAC AAC GTG
 361  Gly Thr Ser Ser Asn Leu Pro Ser Ala Val Tyr Arg Lys Ser Gly Thr Val Asp Ser Leu Asp Ser Ile Pro Pro Gln Asn Asn Val

1261  CCA CCT CGC CAA GGC TTC TCT CAC CGC TTG CGC AGC CAC GTT GTG CAC AGC TTC CGT ATG TTC GGT AAC AGC AGC TCT GTG AGG ATT ATC GCC
 421  Pro Pro Arg Gln Gly Phe Ser His Arg Leu Arg Ser His Val Val His Ser Phe Arg Met Phe Gly Asn Ser Ser Val Arg Ile Ile Ala

1351  CCA ATG TTC TCC TGG ATT CAC CGT TCT GCT GAG GCA GGT TTC GAT AGC ATC ACT CAA ATC CCT GCT GTT AAG GGC AAC
 451  Pro Met Phe Ser Trp Ile His Arg Ser Ala Glu Ala Gly Phe Asp Ser Ile Thr Gln Ile Pro Ala Val Lys Gly Asn

1441  TTC CTT TTC AAC GGC GTC ATC TCG GGT GTC GAC CTT GTG CGC TTG GAC TAC AGG GTC AGC TAC GCT TCT GTG ACC ATC CAC
 481  Phe Leu Phe Asn Gly Val Ile Ser Gly Val Asp Leu Val Arg Leu Asp Tyr Arg Val Ser Tyr Ala Ser Val Thr Pro Ile His
                                                                                                        PstI
1531  AGG GGT TAC ATC GAG GTG CCA ATC CAC TTC CCA TCC AGG GTC AGG GTC AGG GTC CGC TAC AGG CAG CTG AAC CTT GAC AAC
 511  Arg Gly Tyr Ile Glu Val Pro Ile His Phe Pro Ser Thr Arg Val Arg Val Arg Val Arg Tyr Arg Gln Leu Asn Leu Asp Asn

1621  TTG AAC TGG AAC GCC AAC AGC AGC TCC ATC TTC AGC ACC ACG GCC ACC CTT GAC AAC CTG CAG TCC TCG GAC TTC
 541  Leu Asn Trp Asn Gly Asn Ser Ser Ile Phe Ser Thr Thr Ala Thr Leu Asp Asn Leu Gln Ser Ser Asp Phe

1711  GGC TAC TTC GAA TCG GCC AAC GCT GCT AAC GCT TTC ACC AGC TCT TCT CTT GGC GTG ATC GGT GAC TTC TCT GGC ACG GCT ATC ATC
 571  Gly Tyr Phe Glu Ser Ala Asn Ala Phe Thr Ser Ser Ser Leu Gly Val Ile Gly Asp Phe Ser Gly Thr Ala Gly Val Ile Ile
       EcoRI
1801  GAC CGC GAA TTC ATC CCA GTG ACG GCT ACC CTG GAG GCT CCA TAG
 601  Asp Arg Glu Phe Ile Pro Val Thr Ala Thr Leu Glu Ala Glu Pro Pro ***
```

What is claimed is:

1. A plant optimized nucleotide sequence that encodes an insecticidal crystal protein (ICP), wherein the plant optimized nucleotide sequence is SEQ ID NO: 1.

2. A purified ICP gene having a nucleotide sequence according to SEQ ID NO:1.

3. The purified ICP gene according to claim 2, wherein the ICP gene is inserted into the vector pDAB 917 and has accession number NRRL B-30042.

4. A synthetic genetic construct that expresses in plant cells comprising in sequence 5' to 3':

a promoter sequence that initiates transcription in plant cells;

a translational enhancer sequence;

a plant optimized nucleotide gene sequence encoding an insecticidal crystal protein (ICP) wherein the gene sequence is SEQ ID NO: 1; and a polyadenylation sequence, wherein said promoter sequence, translational enhancer sequence, plant optimized nucleotide sequence and polyadenylation sequence are operably linked.

5. A synthetic gene construct according to claim 4, wherein the promoter is selected from the group consisting of inducible promoters, constitutive promoters, temporal-regulated promoters, developmentally-regulated promoters, tissue-preferred promoters, and tissue-specific promoters.

6. A synthetic genetic construct according to claim 4, wherein the promoter is CaMV 35S.

7. A synthetic genetic construct according to claim 4, wherein the translational enhancer sequence is a maize intron.

8. A synthetic genetic construct according to claim 7, wherein the maize intron is intron 1 or intron 6 of Adh1.S.

9. A trangenic maize plant wherein cells of the plant have been transformed with a plant optimized nucleotide sequence encoding an insecticidal crystal protein (ICP), wherein the plant optimized nucleotide sequence is SEQ ID NO:1.

10. A plant seed having in its genome an inheritable synthetic gene, wherein the synthetic gene comprises a plant optimized nucleotide sequence encoding an insecticidal crystal protein (ICP), wherein the plant optimized nucleotide sequence is SEQ ID NO: 1.

* * * * *